(12) United States Patent
Chung et al.

(10) Patent No.: US 11,162,104 B2
(45) Date of Patent: Nov. 2, 2021

(54) SCN9A ANTISENSE PAIN KILLER

(71) Applicant: OliPass Corporation, Yongin-si (KR)

(72) Inventors: Shin Chung, Yongin-si (KR); Daram Jung, Hwaseong-Si (KR); Bongjun Cho, Yongin-Si (KR); Kangwon Jang, Yongin-Si (KR); Hyun Ju Jeon, Yongin-Si (KR); Jinyoung Bae, Yongin-Si (KR); Taeyeon Bae, Yongin-Si (KR); Yeasel Jeon, Yongin-Si (KR); Jun Yeon Lee, Yongin-Si (KR); Sun Hwa Park, Siheung-Si (KR); Dan Bi An, Yongin-Si (KR)

(73) Assignee: OliPass Corporation, Yongin-si (KR)

(*) Notice: Subject to any disclaimer, the term of this patent is extended or adjusted under 35 U.S.C. 154(b) by 26 days.

(21) Appl. No.: 16/480,147

(22) PCT Filed: Jan. 23, 2018

(86) PCT No.: PCT/IB2018/000160
§ 371 (c)(1),
(2) Date: Jul. 23, 2019

(87) PCT Pub. No.: WO2018/138585
PCT Pub. Date: Aug. 2, 2018

(65) Prior Publication Data
US 2019/0338292 A1 Nov. 7, 2019

Related U.S. Application Data

(60) Provisional application No. 62/449,738, filed on Jan. 24, 2017.

(51) Int. Cl.
| | | |
|---|---|---|
| *C07H 21/02* | (2006.01) | |
| *C07H 21/04* | (2006.01) | |
| *C12N 15/113* | (2010.01) | |
| *C07K 14/00* | (2006.01) | |

(52) U.S. Cl.
CPC ........ *C12N 15/1138* (2013.01); *C07K 14/003* (2013.01); *C12N 15/113* (2013.01); *C12N 2310/11* (2013.01); *C12N 2310/3181* (2013.01); *C12N 2310/333* (2013.01); *C12N 2310/334* (2013.01); *C12N 2310/335* (2013.01); *C12N 2310/336* (2013.01); *C12N 2320/33* (2013.01)

(58) Field of Classification Search
CPC .............. C12N 15/113; C12N 2310/11; C12N 2310/3181
See application file for complete search history.

(56) References Cited

U.S. PATENT DOCUMENTS

| | | |
|---|---|---|
| 6,617,422 B1 | 9/2003 | Nielsen et al. |
| 8,183,221 B2 | 5/2012 | Thakker et al. |
| 2006/0106112 A1* | 5/2006 | Ehring ................. A61K 31/235 514/641 |
| 2013/0210884 A1 | 8/2013 | MacDonald et al. |

FOREIGN PATENT DOCUMENTS

| | | |
|---|---|---|
| KR | 2011/0087436 A | 8/2011 |
| WO | WO-2007/109324 A2 | 9/2007 |
| WO | WO-2009/033027 A2 | 3/2009 |
| WO | WO-2009113828 A2 | 9/2009 |
| WO | WO-2018/029517 A1 | 2/2018 |
| WO | WO-2018/051175 A1 | 3/2018 |
| WO | WO-2018/122610 A1 | 7/2018 |

OTHER PUBLICATIONS

Chatelier et al., "Biophysical Properties of Human Nav1.7 Splice Variants and Their Regulation by Protein Kinase A," Journal of Neurophysiology, 99(5): 2241-2250 (2008).
Choi et al., "Alternative splicing may contribute to time-dependent manifestation of inherited erythromelalgia," Brain, 133(Pt 6):1823-1835 (2010).
Drenth et al., "Mutations in sodium-channel gene SCN9A cause a spectrum of human genetic pain disorders," The Journal Of Clinical Investigation, 117(12): 3603-3609 (2007).
Emery et al., "Nav1.7 and other voltage-gated sodium channels as drug targets for pain relief," Expert Opinion on Therapeutic Targets, 20(8): 975-983 (2016).
Extended European Search Report and Written Opinion for EP Application No. 18744379.1 dated Nov. 13, 2020.
Extended European Search Report for EP Application No. 17850354.6 dated Mar. 30, 2020.
International Search Report and Written Opinion for International Application No. PCT/IB2017/000751 dated Sep. 29, 2017.
Karras et al., "Peptide nucleic acids are potent modulators of endogenous pre-mRNA splicing of the murine interleukin-5 receptor-α chain," Biochemistry, 40(26):7853-7859 (2001).
Muroi et al., "Selective silencing of NaV1.7 decreases excitability and conduction in vagal sensory neurons," The Journal Of Physiology, 589(23): 5663-5676 (2011).
Pan et al., "Effect of down-regulation of voltage-gated sodium channel Nav1.7 on activation of astrocytes and microglia in DRG in rats with cancer pain," Asian Pacific Journal of Tropical Medicine, 8(5): 405-411 (2015).
Singapore Search Report for Application No. 11201905601V dated Apr. 15, 2020.

(Continued)

*Primary Examiner* — Amy H Bowman
(74) *Attorney, Agent, or Firm* — David P. Halstead; Mi Cai; Foley Hoag LLP

(57) ABSTRACT

The current invention provides peptide nucleic acid derivatives targeting the 3' splice site of exon 4 in the human SCN9A pre-mRNA. The peptide nucleic acid derivatives potently induce SCN9A mRNA splice variant(s) lacking the SCN9A exon 4 in cells, and are useful to safely treat pains or conditions involving $Na_v1.7$ activity.

24 Claims, 30 Drawing Sheets
Specification includes a Sequence Listing.

(56) References Cited

OTHER PUBLICATIONS

International Search Report and Written Opinion for International Application No. PCT/IB2018/000160 dated Jun. 22, 2018.
Kerr et al., "Novel mRNA Isoforms of the Sodium Channels Nav1.2, Nav1.3 and Nav1.7 Encode Predicted Two-Domain, Truncated Proteins," Neuroscience, 155: 797-808 (2008).
Peacey et al., "Targeting a Pre-mRNA Structure with Dipartite Antisense Molecules Modulates Tau Alternative Splicing," Nucleic Acids Res, 40(19): 9836-9849 (2012).
Siwkowski et al., "Identification and Functional Validation of PNAs that Inhabit Murine CD40 Expression by Redirection of Splicing," Nucleic Acids Res, 32(9): 2695-2706 (2004).
U.S. Appl. No. 16/333,855, Published.

\* cited by examiner

Lidocaine

Tetrodotoxin hNav1.7 IC$_{50}$ = 0.55 µM hNav1.5 IC$_{50}$ = 4.30 µM

Funapide

Raxatrigine

PF-05089771

Figure 4 (continued from previous page)
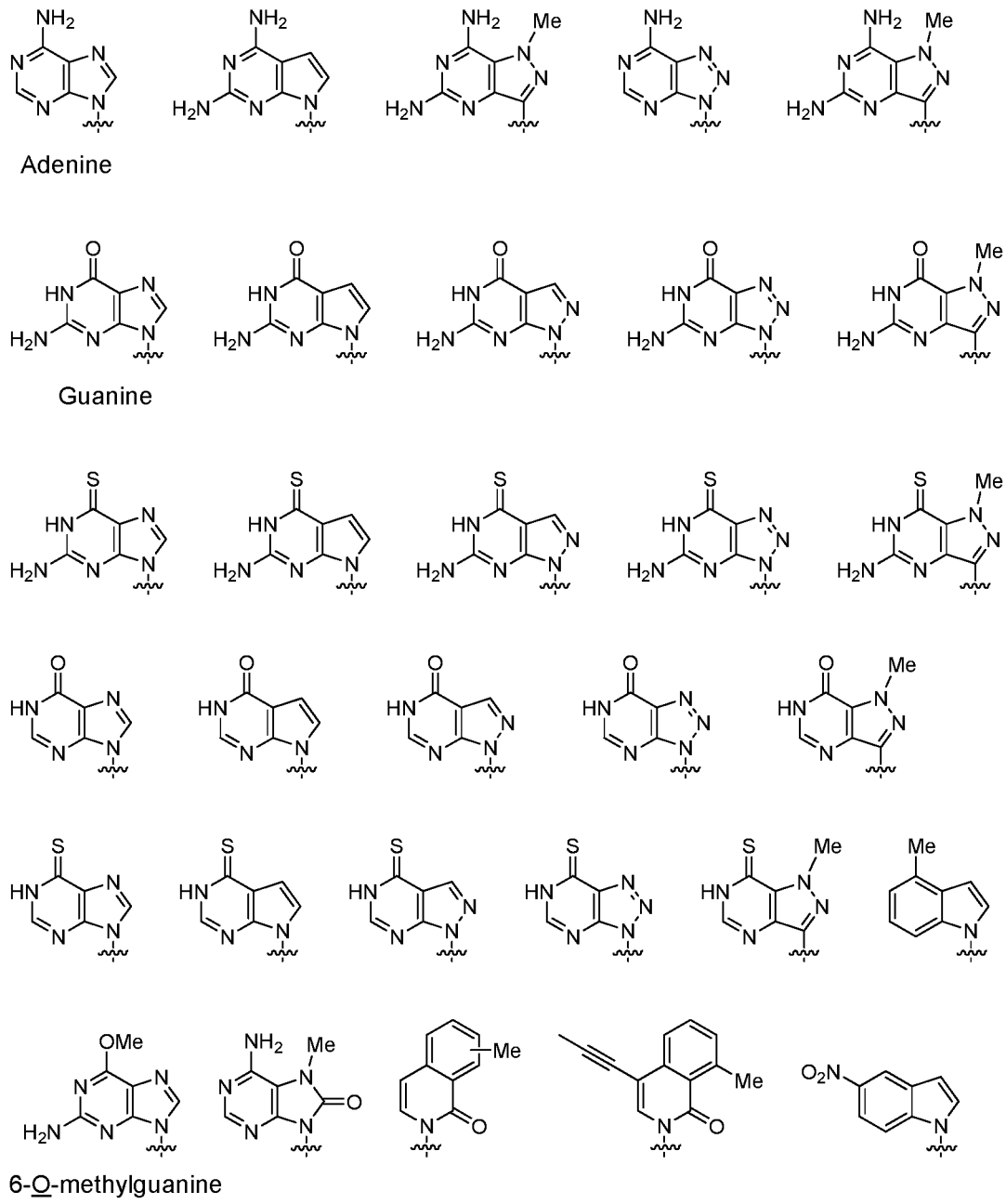

Figure 4 (continued from previous page)
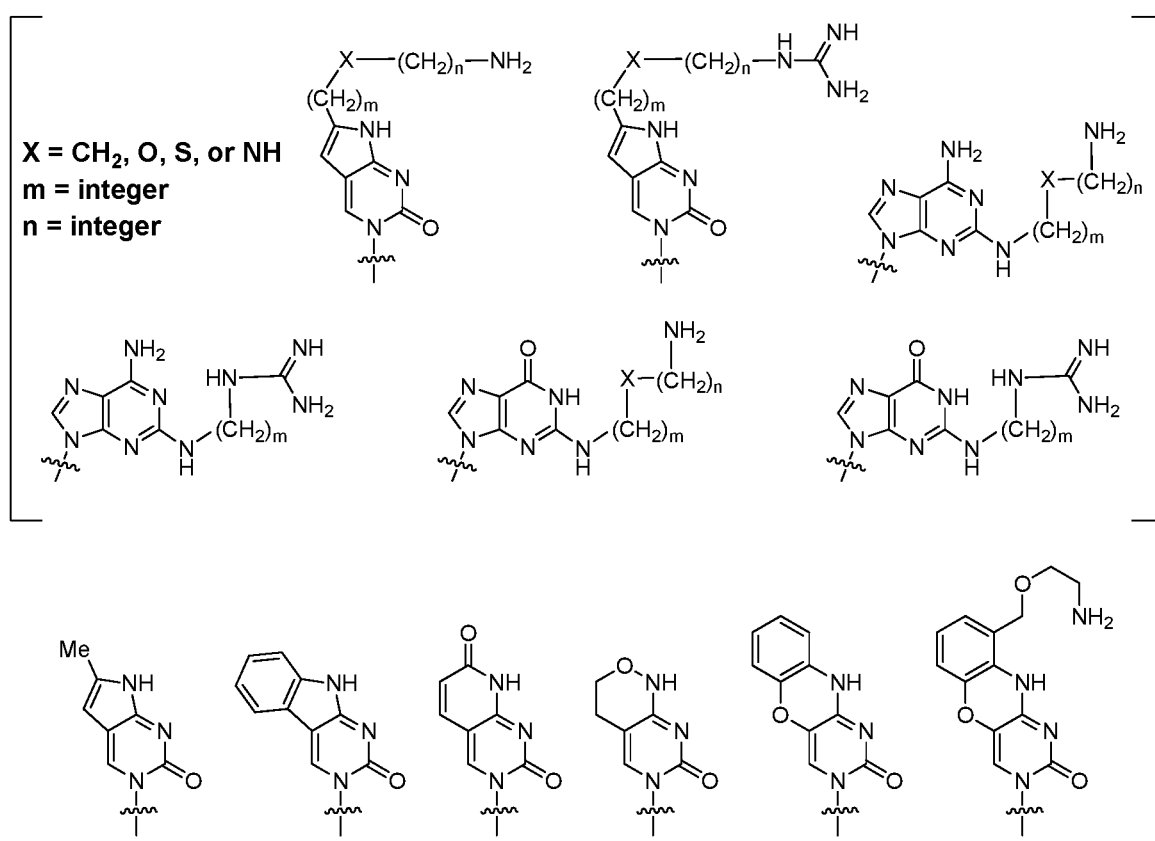

Examples of Non-substituted Alkyl Radical

Examples of Substituted Alkyl Radical

Examples of Non-substituted Alkylacyl Radical

Examples of Substituted Alkylacyl Radical

Examples of Substituted or Non-substituted Arylacyl Radical

Examples of Substituted Alkylamino or Arylamino Radical

Examples of Substituted or Non-substituted Aryl Radical

Examples of Substituted or Non-substituted Alkylsulfonyl or Arylsulfonyl Radical Examples of Substituted or Non-substituted Alkyl- or Aryl-phosphonyl Radical

Examples of Substituted or Non-substituted Alkyloxycarbonyl Radical

Examples of Substituted or Non-substituted Aryloxycarbonyl Radical

Examples of Substituted or Non-substituted Alkylaminocarbonyl Radical

Examples of Substituted or Non-substituted Arylaminocarbonyl Radical

Examples of Substituted or Non-substituted Alkyloxythiocarbonyl Radical

Examples of Substituted or Non-substituted Alkylaminothiocarbonyl Radical

Examples of Substituted or Non-substituted Arylaminothiocarbonyl Radical

Examples of Substituted or Non-substituted Aryloxythiocarbonyl Radical

PNA Monomer

B : Nucleobase
X : O (oxygen atom)
p : Integer
q : Integer

Adenine

B =

Guanine

B =

Thymine

B =

Cytosine

B =

Modified Cytosine

C(pXq) : B =

Modified Adenine

A(p) : B =

A(pXp) :

B =

Modified Guanine

G(p) : B =

G(pXq) :

B =

Fmoc-PNA Monomer

B : Nucleobase with protecting group(s)
X : methylene, oxygen, sulfur, or Boc-protected amino
m : Integer
n : Integer

Boc-

Modified Cytosine

C(mXn) : B =

Modified Adenine

A(mXn) :

B =

Modified Guanine

G(mXn) :

B =

SEQUENCE LISTING

<160> NUMBER OF SEQ ID NOS: 23

<210> SEQ ID NO 1
<211> LENGTH: 19
<212> TYPE: RNA
<213> ORGANISM: Homo sapiens

-continued

<400> SEQUENCE: 1
gauuauggcu acacgagcu                                                19

<210> SEQ ID NO 2
<211> LENGTH: 14
<212> TYPE: RNA
<213> ORGANISM: Homo sapiens

<400> SEQUENCE: 2
uguuuaggua cacu                                                     14

<210> SEQ ID NO 3
<211> LENGTH: 30
<212> TYPE: RNA
<213> ORGANISM: Homo sapiens

<400> SEQUENCE: 3
gaaucuugug uuuagguaca cuuuuacugg                                     30

<210> SEQ ID NO 4
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
aagtgtacct aaac                                                     14

<210> SEQ ID NO 5
<211> LENGTH: 20
<212> TYPE: RNA
<213> ORGANISM: Homo sapiens

<400> SEQUENCE: 5
uuguguuuag guacacuuuu                                                20

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
aagtgtacct aaacacaa                                                 18

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
aagtctacct aaacacta                                                 18

<210> SEQ ID NO 8
<211> LENGTH: 14
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 8
aagtgtacct aaag                                                           14

<210> SEQ ID NO 9
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
aggtacactt                                                                10

<210> SEQ ID NO 10
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gtttaggtac                                                                10

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ctttctcctt tcagtcctct                                                     20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
cgtctgttgg taaaggtttt                                                     20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ccaccggact ggaccaaaaa                                                     20

<210> SEQ ID NO 14
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 14
gctaagaagg cccagctgaa                                                20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ggaccaaaaa tgtcgagcct                                                20

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tgaccatgaa taacccac                                                  18

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gcaaggattt ttacaagt                                                  18

<210> SEQ ID NO 18
<211> LENGTH: 13
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 18
atgtcgagta cac                                                       13

<210> SEQ ID NO 19
<211> LENGTH: 20
<212> TYPE: RNA
<213> ORGANISM: Rattus sp.

<400> SEQUENCE: 19
uuuccuuuag guacacuuuu                                                20

<210> SEQ ID NO 20
<211> LENGTH: 25
<212> TYPE: RNA
<213> ORGANISM: Homo sapiens

<400> SEQUENCE: 20
uuguguuuag guacacuuuu acugg                                          25
```

```
<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
caatcttccg tttcaacgcc                                              20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
accacagcca ggatcaagtt                                              20

<210> SEQ ID NO 23
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
ggaccaaaaa tgtcgagcct gaaga                                        25
```

SCN9A ANTISENSE PAIN KILLER

This application is a national-stage filing under 35 U.S.C. § 371 of International Application No. PCT/IB2018/000160, filed Jan. 23, 2018, which claims the benefit of priority to U.S. Provisional Application No. 62/449,738 filed Jan. 24, 2017, each of which is incorporated by reference herein in its entirety.

SEQUENCE LISTING

The instant application contains a Sequence Listing which has been submitted electronically in ASCII format and is hereby incorporated by reference in its entirety. Said ASCII copy, created on Jul. 15, 2019, is named OSH-00701_ (32567-00701)_SL.txt and is 5,038 bytes in size.

BACKGROUND OF INVENTION

Voltage-gated sodium channels (VGSCs) are trans-membrane proteins composed of α and β subunits. VGSCs function as a gateway for sodium ions to cross the cell membrane. Sodium channel activity is produced by α-subunit. VGSC subtype is defined according to the subtype of α-subunit. To date, there are at least 10 subtypes of VGSC, i.e. $Na_v1.1$, $Na_v1.2$, ..., $Na_v1.9$, and $Na_x$.

Each VGSC subtype has a distinct α subunit, and is destined to show characteristic physiological roles depending on the tissue of expression. For example, $Na_v1.2$ subtype is expressed in central neurons and appears to be linked to epilepsy. [*Human Mol. Genet.* vol 24(5), 1459-1468 (2015)] $Na_v1.5$ subtype is abundantly expressed in cardiomyocytes. Inhibition of $Na_v1.5$ may cause long QT syndrome and sudden death. [*Handbook Exp. Pharmacol.* vol 221, 137-168 (2014)] $Na_v1.7$ subtype is abundantly expressed in dorsal root ganglia. Upregulation of the $Na_v1.7$ activity causes erythromelalgia. [*J. Med. Genet.* vol 41, 171-174 (2004)] In the meantime, people genetically lacking the $Na_v1.7$ activity (i.e., SCN9A channelopathy) do not feel severe pains, although those individuals were found to be normal in other sensory functions. [*Nature* vol 444, 894-898 (2006)]

Tetrodotoxin (TTX) is a neurotoxin found in pufferfish. TTX is extremely toxic and its intra-peritoneal $LD_{50}$ is 10 µg/Kg in mice. [*Toxins* vol 6, 693-755 (2014)]. Oral ingestion of TTX can cause paresthesia of the lips and tongue, hypersalivation, sweating, headache, tremor, paralysis, cyanosis, seizures, incoordination, diarrhea, abdominal pain, hypotension, respiratory distress, cardiac arrhythmias, coma, and so on. TTX is known to induce such adverse effects by non-specifically binding to the active sites of VGSC subtypes. Thus nonspecific inhibition of VGSC subtypes would incur serious adverse events.

Lidocaine is a non-specific VGSC inhibitor, and has been widely used as a local anesthetic agent. Upon intravenous administration, lidocaine may induce undesirable side effects such as muscle twitching, vomiting, irregular heartbeat, sleepiness, and so on. Such side effects are considered to be due to nonspecific inhibition of VGSC subtypes. However, the inhibition of $Na_v1.5$ with lidocaine would be useful to treat ventricular tachycardia. Nevertheless, systemic administration of lidocaine is considered to be undesirable to treat chronic pains due to adverse events arising from non-specific inhibition of sodium channel subtypes.

SCN9A Channelopathy: SCN9A (sodium channel subtype 9A) gene encodes the α-subunit of VGSC subtype $Na_v1.7$. There are an extremely small number of individuals who do not feel severe pains but are normal in other sensory functions. Such individuals were found to have the SCN9A gene mutated to encode nonfunctional $Na_v1.7$ subtype. [*Nature* vol 444, 894-898 (2006)] This has been termed as SCN9A channelopathy. The behavioral phenotypes of the human SCN9A channelopathy are reproduced fairly much in SCN9A knockout mice. [*PLoS One* 9(9): e105895 (2014)] Therefore selective inhibition of $Na_v1.7$ subtype would be useful to safely treat chronic pains in human patients.

$Na_v1.7$ Selective Small Molecule Inhibitors: Reflecting the physiological function of VGSC, the active sites of VGSC subtypes are similar in their 3D structure. By directly targeting the active site with small molecule inhibitors, selective inhibition of $Na_v1.7$ subtype would be highly challenging. Lidocaine and tetrodotoxin are good examples for such non-selective inhibitors of VGSC subtypes. (cf. FIG. 1A)

$Na_v1.7$ inhibitors with a modest selectivity over $Na_v1.5$ (ca. 8-fold) were identified through a high throughput screen campaign with a library of 200,000 compounds to identify $Na_v1.8$ selective inhibitors. [*J. Gen. Physiol.* vol 131(5), 399-405 (2008)] A 1-benzazepin-2one derivative was found to selectively inhibit $Na_v1.7$ over $Na_v1.5$ with a modest $Na_v1.7$ selectivity (ca 8-fold) by electrophysiology assay. (cf. FIG. 1B)

To date, a number of $Na_v1.7$ selective small molecule inhibitors have been disclosed, and several were evaluated in human patients. (cf. FIG. 1C) For example, funapide (XEN-402/TV-45070) was evaluated in a small number of erythromelalgia patients. [*Pain* vol 153, 80-85 (2012)] Although funapide showed analgesic activity, funapide showed treatment related and dose limiting adverse events including dizziness and somnolence in a relatively large portion of the enrolled patients. The CNS adverse events suggest that the $Na_v1.7$ selectivity of funapide would not be high enough to safely treat chronic pains.

Raxatrigine (CNV1014802/GSK-1014802) inhibits $Na_v1.7$ as well as other VGSC subtypes. However, raxatrigine has been claimed to inhibit the functional activity of sodium channel by stabilizing selectively the inactive state of sodium channel Although raxatrigine inhibits sodium channel subtypes in the CNS, it was well tolerated at therapeutic dose. [*The Pharmaceutical J.* 11 Mar. 2016. $Na_v1.7$: a new channel for pain treatment] Raxatrigene showed good analgesic activity in patients with trigeminal neuralgia, although the patients were enrolled for clinical evaluation based on strict cardiologic criteria due to potential cardiotoxicity from the relatively poor $Na_v1.7$ selectivity.

PF-05089771 is a $Na_v1.7$ selective inhibitor with an $IC_{50}$ of 11 nM. PF-05089771 was claimed to stabilize the inactive form of $Na_v1.7$. [*Biophysical J.* vol 108(2) Suppl., 1573a-1574a (2015)] The therapeutic potential PF-05089771 was evaluated in patients of erythromelalgia or dental pain following a wisdom tooth extraction. A pharmacokinetic analysis of PF-05089771 suggested that the low drug concentration in the target tissue responsible for neuropathic pain could be a possible explanation for its poor analgesic activity in human patients. [*Clin. Pharmacokinet.* vol 55(7), 875-87 (2016)] Although PF-05089771 has been claimed to possess an excellent $Na_v1.7$ selectivity over $Na_v1.5$, its molecular size appears to be too big to show good distribution to CNS tissues of therapeutic concern for chronic neuropathic pains.

$Na_v1.7$ selective small molecule inhibitors were reviewed from structural aspects. [*Bioorg. Med. Chem. Lett.* vol 24, 3690-3699 (2014)] The molecular size of such $Na_v1.7$ selective inhibitors tends to be considerably larger than lidocaine, a non-selective inhibitor of VGSC subtypes. $Na_v1.7$ selectivity was improved by making the molecular size large. Each $Na_v1.7$ selective inhibitor is considered to bind to a distinct domain within the $Na_v1.7$ protein, and the binding domain varies depending on the chemical structure of the inhibitor. Ironically, the analgesic efficacy of $Na_v1.7$ selective inhibitors was not strong and failed to meet the expectation suggested from the findings in people with SCN9A channelopathy. [*Expert Opin. Ther. Targets* vol 20(8), 975-983 (2016)]

Other Types of $Na_v1.7$ Selective Inhibitors: Tarantula venom peptide ProTx-II was found to selectively inhibit $Na_v1.7$ over other VGSC subtypes. However, the venom showed weak analgesic activity in animal models of acute inflammatory pain. [*Mol. Pharmacol.* vol 74, 1476-1484 (2008)] Given that the electrophysiology of the venom peptide was evaluated in HEK-293 cells engineered to abundantly express each subtype of VGSC, ProTx-II might not bind to the active site of $Na_v1.7$ in primary neuronal cells. Primary neuronal cells express Nav1.7 consisting of the α- and β-chain, whilst HEK-293 cells are usually engineered to stably express only the α-chain of each VGSC subtype.

Ssm6a, a 46-mer peptide isolated from centipede venom, was found to selectively inhibit $Na_v1.7$ over other VGSC subtypes. The observed $Na_v1.7$ $IC_{50}$ was 0.3 nM in HEK-293 cells engineered to overexpress $Na_v1.7$. The centipede venom peptide showed an analgesic efficacy comparable to morphine by formalin test in mice, an acute inflammatory pain model. The 46-mer peptide also suppressed the sodium current in rat DRG cells. Although the venom peptide showed robust stability in serum, the analgesic activity lasted only a few hours. [*Proc. Nat. Acad. Sci. USA* vol 110(43), 17534-17539 (2013)]

SVmab1 is a monoclonal antibody selectively targeting $Na_v1.7$ over other VGSC subtypes in HEK-293 cells overexpressing each VGSC subtype. SVmab1 selectively inhibited the sodium current evoked by $Na_v1.7$ with an $IC_{50}$ of 30 nM in HEK-293 cells. The monoclonal antibody showed a marked analgesic activity upon an intravenous (at 50 mg/Kg) or intrathecal (10 µg, i.e. ca 0.5 mg/Kg) administration against formalin test in mice. Based on the difference in the analgesic potency of the two administration routes, the inhibition of $Na_v1.7$ in the spinal cord or CNS should be the major contributor to the analgesic activity against the formalin test. [*Cell* vol 157(6), 1393-1404 (2014)]

Species Difference in $Na_v1.7$ Contribution to Pain Sensation: Recently human DRGs from healthy volunteers were evaluated by qPCR for the relative expression levels of VGSC subtypes. *Neurosci. Bull.* DOI 10.1007/s12264-017-0132-3, published online 19 Apr. 2017] In human DRGs, the expression of the $Na_v1.7$ subtype was ca 50% of the total VGSC expression. $Na_v1.8$ contributed to ca 12%. A 24 hours incubation of human DRG neuronal cells with paclitaxel upregulated $Na_v1.7$ but not $Na_v1.8$, indicating that $Na_v1.7$ should be the overriding subtype for neuropathy over $Na_v1.8$ in humans. These findings strongly support the phenotypes observed in the human SCN9A channelopathy. [*Nature* vol 444, 894-898 (2006)]

In the meantime, the contribution of $Na_v1.8$ was overriding to occupy 48% of the whole VGSC expression in the mouse DRG. The $Na_v1.7$ contribution was 18% in the DRG from naïve CD mice (8 to 10 weeks old). Thus discretion should be taken in extrapolating animal pain data to the therapeutic dose in human subjects. Likewise animal pain models need to be carefully assessed with the $Na_v1.7$ expression level in target tissue into account.

Pre-mRNA: Genetic information is carried on DNA (2-deoxyribose nucleic acid). DNA is transcribed to produce pre-mRNA (pre-messenger ribonucleic acid) in the nucleus. Mammalian pre-mRNA usually consists of exons and introns, and exon and intron are inter-connected to each other. Exons and introns are numbered as illustrated in FIG. 1D.

Splicing of Pre-mRNA: Pre-mRNA is processed into mRNA following deletion of introns by a series of complex reactions collectively called "splicing" as schematically illustrated in FIG. 2A. [*Ann. Rev. Biochem.* 72(1), 291-336 (2003); *Nature Rev. Mol. Cell Biol.* 6(5), 386-398 (2005); *Nature Rev. Mol. Cell Biol.* 15(2), 108-121 (2014)]

Splicing is initiated by forming "splicesome E complex" (i.e. "early splicesome complex") between pre-mRNA and splicing adapter factors. In "splicesome E complex", U1 binds to the junction of exon N and intron N, and $U2AF^{35}$ binds to the junction of intron N and exon (N+1). Thus the junctions of exon/intron or intron/exon are critical to the formation of the early splicesome complex. "Splicesome E complex" evolves into "splicesome A complex" upon additional complexation with U2. The "splicesome A complex" undergoes a series of complex reactions to delete or splice out the intron to adjoin the neighboring exons.

Ribosomal Protein Synthesis: Proteins are encoded by mRNA (messenger ribonucleic acid). In response to cellular stimulation or spontaneously, DNA is transcribed to produce pre-mRNA (pre-messenger ribonucleic acid) in the nucleus. The introns of pre-mRNA are enzymatically spliced out to yield mRNA, which is then translocated into the cytoplasm. In the cytoplasm, a complex of translational machinery called ribosome binds to mRNA and carries out the protein synthesis as it scans the genetic information encoded along the mRNA. [*Biochemistry* vol 41, 4503-4510 (2002); *Cancer Res.* vol 48, 2659-2668 (1988)]

Antisense Oligonucleotide (ASO): An oligonucleotide binding to nucleic acid including DNA, mRNA and pre-mRNA in a sequence specific manner (i.e. complementarily) is called antisense oligonucleotide (ASO).

If an ASO tightly binds to an mRNA in the cytoplasm, for example, the ASO may be able to inhibit the ribosomal protein synthesis along the mRNA. ASO needs to be present within the cytoplasm in order to inhibit the ribosomal protein synthesis of its target protein.

If an ASO tightly binds to a pre-mRNA in the nucleus, the ASO may be able to inhibit or modulate the splicing of pre-mRNA into mRNA. ASO needs to be present within the nucleus in order to inhibit or modulate the splicing of pre-mRNA into mRNA. Such antisense inhibition of splicing produces an mRNA or mRNAs lacking the exon targeted by the ASO. Such mRNA(s) is called "splice variant(s)", and encodes protein(s) smaller than the protein encoded by the full-length mRNA.

In principle, splicing can be interrupted by inhibiting the formation of "splicesome E complex". If an ASO tightly binds to a junction of (5'→3') exon-intron, i.e. "5' splice site", the ASO blocks the complex formation between pre-mRNA and factor U1, and therefore the formation of "splicesome E complex". Likewise, "splicesome E complex" cannot be formed if an ASO tightly binds to a junction of (5'→3') intron-exon, i.e. "3' splice site". 3' splice site and 5' splice site are schematically illustrated in FIG. 2B.

Unnatural Oligonucleotides: DNA or RNA oligonucleotides are susceptible to degradation by endogenous nucleases, limiting their therapeutic utility. To date, many types of unnatural (i.e., naturally non-occurring) oligonucleotides have been developed and studied intensively. [*Clip. Exp. Pharmacol. Physiol.* vol 33, 533-540 (2006)] Some of them show extended metabolic stability compared to DNA and RNA. Provided in FIG. 3A are the chemical structures for some of representative unnatural oligonucleotides. Such oligonucleotides predictably bind to a complementary nucleic acid as DNA or RNA does.

Phosphorothioate Oligonucleotide: Phosphorothioate oligonucleotide (PTO) is a DNA analog with one of the backbone phosphate oxygen atoms replaced with a sulfur atom per monomer. Such a small structural change made PTO comparatively resistant to degradation by nucleases. [*Ann. Rev. Biochem.* vol 54, 367-402 (1985)]

Reflecting the structural similarity in the backbone of PTO and DNA, they both poorly penetrate the cell membrane in most mammalian cell types. For some types of cells abundantly expressing transporter(s) of DNA, however, DNA and PTO show good cell permeability. Systemically administered PTOs are known to readily distribute to the liver and kidney. [*Nucleic Acids Res.* vol 25, 3290-3296 (1997)]

In order to facilitate PTO's cell penetration in vitro, lipofection has been popularly applied. However, lipofection physically alters the cell membrane, causes cytotoxicity, and therefore would not be ideal for long term in vivo therapeutic use.

Over the past 30 years, antisense PTOs and variants of PTOs have been clinically evaluated to treat cancers, immunological disorders, metabolic diseases, and so on. [*Biochemistry* vol 41, 4503-4510 (2002); *Clin. Exp. Pharmacol. Physiol.* vol 33, 533-540 (2006)] Many of such antisense drug candidates have not been successfully developed partly due to PTO's poor cell permeability. In order to overcome the poor cell permeability, PTO needs to be administered at high dose for therapeutic activity. However, PTOs are known to be associated with dose-limiting toxicity including increased coagulation time, complement activation, tubular nephropathy, Kupffer cell activation, and immune stimulation including splenomegaly, lymphoid hyperplasia, mononuclear cell infiltration. [*Clip. Exp. Pharmacol. Physiol.* vol 33, 533-540 (2006)]

Many antisense PTOs have been found to show due clinical activity for diseases with a significant contribution from the liver or kidney. Mipomersen is a PTO analog which inhibits the synthesis of apoB-100, a protein involved in LDL cholesterol transport. Mipomersen manifested due clinical activity in a population of atherosclerosis patients most likely due to its preferential distribution to the liver. [*Circulation* vol 118(7), 743-753 (2008)] ISIS-113715 is a PTO antisense analog inhibiting the synthesis of protein tyrosine phosphatase 1B (PTP1B), and was found to show therapeutic activity in patients with type II diabetes. [*Curr. Opin. Mol. Ther.* vol 6, 331-336 (2004)]

Locked Nucleic Acid: In locked nucleic acid (LNA), the backbone ribose ring of RNA is structurally constrained to increase the binding affinity for RNA or DNA. Thus, LNA may be regarded as a high affinity DNA or RNA analog. [*Biochemistry* vol 45, 7347-7355 (2006)] LNA also shows poor cell permeability.

Phosphorodiamidate Morpholino Oligonucleotide: In phosphorodiamidate morpholino oligonucleotide (PMO), the backbone phosphate and 2-deoxyribose of DNA are replaced with phosphoramidate and morpholine, respectively. [*Appl. Microbiol. Biotechnol.* vol 71, 575-586 (2006)] Whilst the DNA backbone is negatively charged, the PMO backbone is not charged. Thus the binding between PMO and mRNA is free of electrostatic repulsion between the backbones, and tends to be stronger than the binding between DNA and mRNA. Since PMO is markedly different from DNA in the chemical structure, PMO wouldn't be recognized by the hepatic transporter(s) recognizing DNA or RNA. Nevertheless, PMO doesn't readily penetrate the cell membrane.

Peptide Nucleic Acid: Peptide nucleic acid (PNA) is a polypeptide with N-(2-aminoethyl)glycine as the unit backbone, and was discovered by Peter Nielsen and colleagues. [*Science* vol 254, 1497-1500 (1991)] The chemical structure and abbreviated nomenclature of PNA are illustrated in FIG. 3B. Like DNA and RNA, PNA also selectively binds to complementary nucleic acid. [*Nature (London)* vol 365, 566-568 (1992)] In binding to the complementary nucleic acid, the N-terminus of PNA is regarded as equivalent to the "5'-end" of DNA or RNA, and the C-terminus of PNA as equivalent to the "3'-end" of DNA or RNA.

Like PMO, the PNA backbone is not charged. Thus the binding between PNA and RNA tends to be stronger than the binding between DNA and RNA. Since PNA is markedly different from DNA in the chemical structure, PNA wouldn't be recognized by the hepatic transporter(s) recognizing DNA, and would show a tissue distribution profile different from that of DNA or PTO. However, PNA also poorly penetrates the mammalian cell membrane. (*Adv. Drug Delivery Rev.* vol 55, 267-280, 2003)

Modified Nucleobases to Improve Membrane Permeability of PNA: PNA was made highly permeable to the mammalian cell membrane by introducing modified nucleobases with a cationic lipid or its equivalent covalently attached thereto. The chemical structures of such modified nucleobases are provided in FIG. 3C. Such modified nucleobases of cytosine, adenine, and guanine were found to predictably and complementarily hybridize with guanine, thymine, and cytosine, respectively. [PCT Appl. No. PCT/KR2009/001256; EP2268607; US8680253]

Incorporation of such modified nucleobases onto PNA simulates situations of lipofection. By lipofection, oligonucleotide molecules with phosphate backbone are wrapped with cationic lipid molecules such as lipofectamine, and such lipofectamine/oligonucleotide complexes tend to penetrate the cell membrane rather easily as compared to naked oligonucleotide molecules.

In addition to the good membrane permeability, those modified PNA derivatives were found to show ultra-strong affinity for the complementary nucleic acid. For example, introduction of 4 to 5 modified nucleobases onto 11-mer to 13-mer PNA derivatives readily yielded a $T_m$ gain of 20° C. or higher in duplex formation with the complementary DNA. Such PNA derivatives are highly sensitive to a single base mismatch. A single base mismatch resulted in a $T_m$ loss of 11 to 22° C. depending on the type of modified base as well as PNA sequence.

Small Interfering RNA (siRNA): Small interfering RNA (siRNA) refers to a double stranded RNA of 20-25 base pairs. [*Microbiol. Mol. Biol. Rev.* vol 67(4), 657-685 (2003)] The antisense strand of siRNA somehow interacts with proteins to form an "RNA-induced Silencing Complex" (RISC). Then the RISC binds to a certain portion of mRNA complementary to the antisense strand of siRNA. The mRNA complexed with the RISC undergoes cleavage. Thus siRNA catalytically induces the cleavage of its target mRNA, and consequently inhibits the protein expression by the mRNA. The RISC does not always bind to the full complementary sequence within its target mRNA, which raises concerns relating to off-target effects of an siRNA therapy. Like other classes of oligonucleotide with DNA or RNA backbone, siRNA possesses poor cell permeability and therefore tends to show poor in vitro or in vivo therapeutic activity unless properly formulated or chemically modified to have good membrane permeability.

SCN9A siRNA: A prior art disclosed siRNAs targeting a 19-mer sequence [(5'→3') GAUUAUGGCUACACGAGCU (SEQ ID NO: 1)] within exon 8 of the human SCN9A mRNA. [U.S. Pat. No. 8,183,221] Upon an intrathecal infusion, the siRNAs were claimed to show therapeutic activity in animal models of neuropathic pain and inflammatory pain. The siRNAs were said to down-regulate $Na_v1.7$ expression in rat DRG cells.

SCN9A ASO: 2'-O-methoxyethyl PTO ASOs complementarily targeting the rat SCN9A mRNA were evaluated for their ability to inhibit the expression of the $Na_v1.7$ protein in DRG in rats upon a single subcutaneous injection of 30 mg ASO per subject. An ASO inhibited the expression of the $Na_v1.7$ protein in DRG by more than 80% in week 4 post dose. These SCN9A ASOs inhibited mechanical pain by Randall-Selitto test. The efficacy largely correlated with the expression level of the $Na_v1.7$ protein in DRG. [*Pain*, Mohan and Fitzsimmons et al. in press]

Antisense Inhibition of SCN9A Pre-mRNA Splicing: To date, there are no reported cases of SCN9A ASOs inducing alternative splicing of SCN9A pre-mRNA.

BRIEF DESCRIPTION OF DRAWINGS

FIG. 14B discloses from top to bottom three nucleic acid sequences which are identical and set forth in SEQ ID NO: 23.

SUMMARY OF INVENTION

Figure 1A:
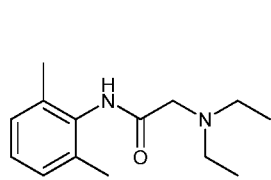
FIG. 1A. The chemical structures of lidocaine and tetrodotoxin, non-selective small molecule inhibitors of voltage-gated sodium channels.
Figure 1A:
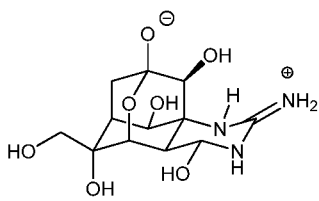
Figure 1B:
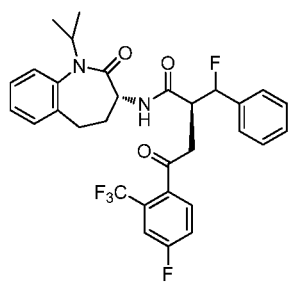
FIG. 1B. A 1-benzazepin-2one inhibitor of $Na_v1.7$ showing a modest selectivity for $Na_v1.7$ over $Na_v1.5$.
Figure 1C:
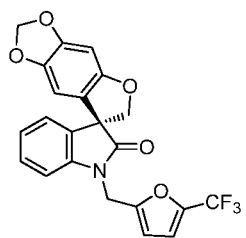
FIG. 1C. The chemical structures of funapide, raxatrigene and PF-05089771, selective small molecule inhibitors of voltage-gated sodium channels.
Figure 1C:
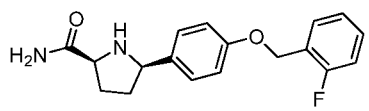
Figure 1C:
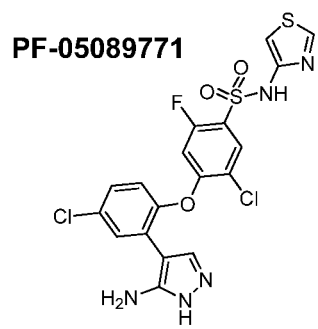
Figure 2A:
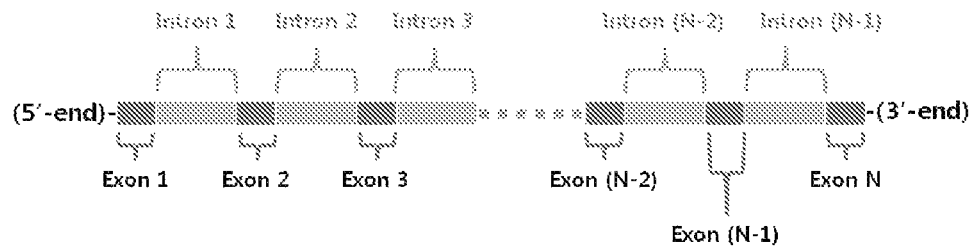
FIG. 2A. Schematic illustration of the numbering of exons and introns within a pre-mRNA.
Figure 2B:
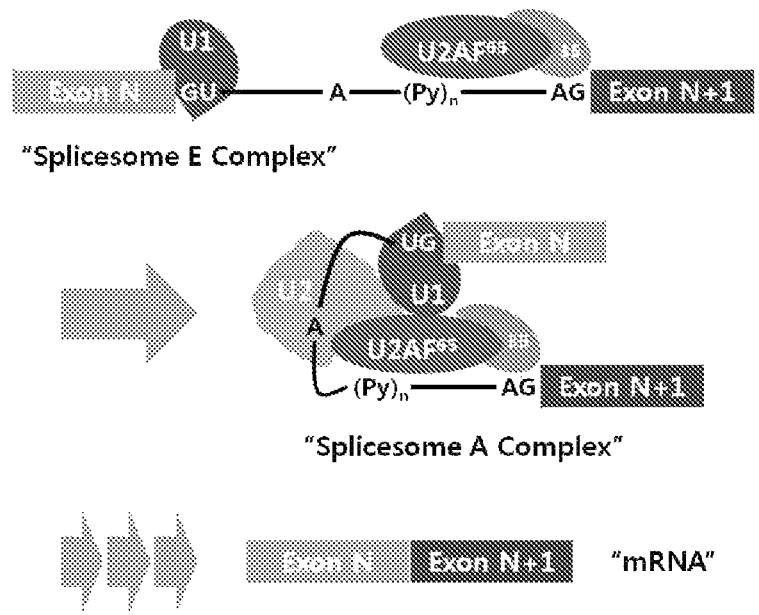
FIG. 2B. Schematic illustration of the splicing process leading to the deletion of intron N.
Figure 2C:
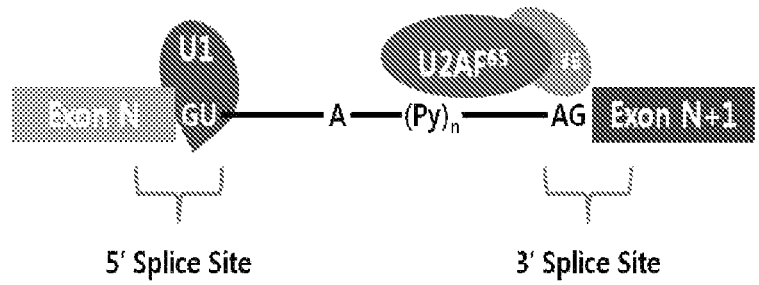
FIG. 2C. Schematic illustration of the 3' splice site and the 5' splice site in relation to splicesome E complex.
Figure 3A:
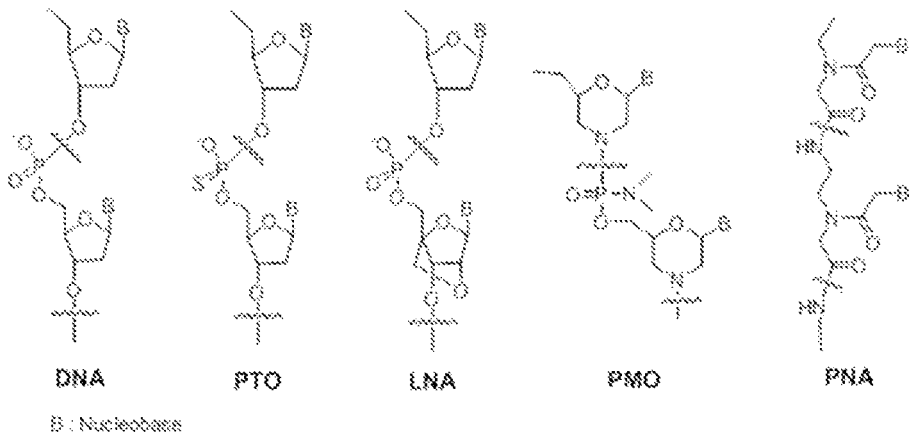
FIG. 3A. Representative chemical structures for DNA and unnatural nucleic acids.
Figure 3B:
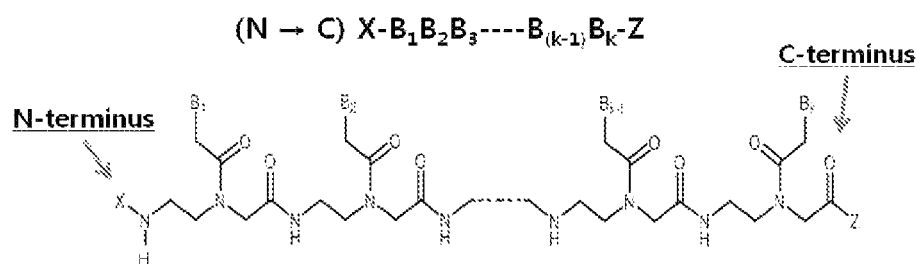
FIG. 3B. Illustration for the chemical structure and abbreviated nomenclature of PNA.
Figure 3C:
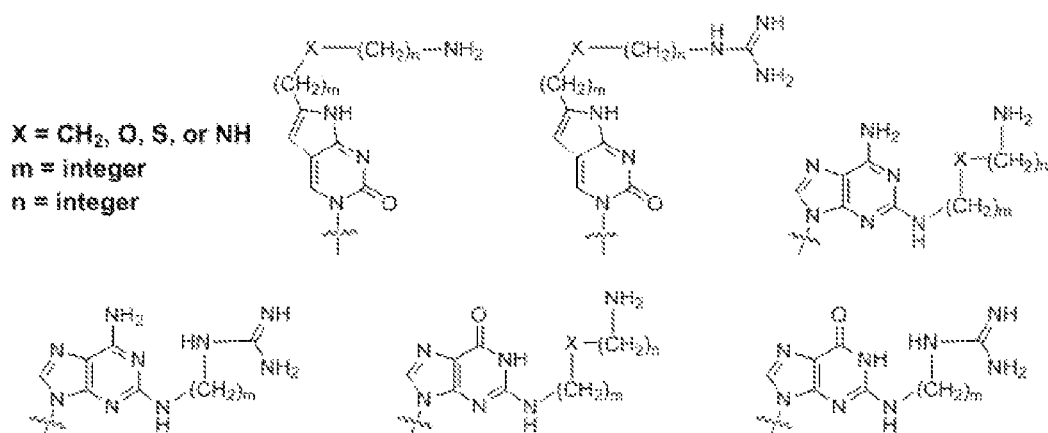
FIG. 3C. Examples of modified nucleobases employed to improve the cell permeability of peptide nucleic acid.

The present invention provides a peptide nucleic acid derivative represented by Formula I, or a pharmaceutically acceptable salt thereof:

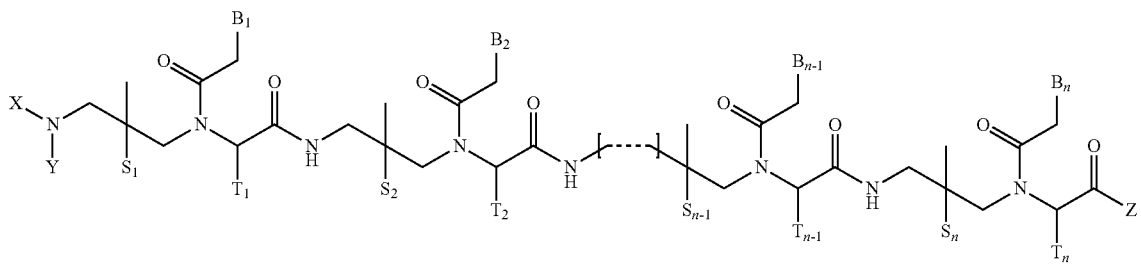

Formula I wherein, n is an integer between 10 and 25;

the compound of Formula I possesses at least a 10-mer complementary overlap with a 14-mer pre-mRNA sequence of [(5'→3') UGUUUAGGUACACU (SEQ ID NO: 2)] within the human SCN9A pre-mRNA;

the compound of Formula I is fully complementary to the human SCN9A pre-mRNA, or partially complementary to the human SCN9A pre-mRNA with one or two mismatches;

$S_1, S_2, \ldots, S_{n-1}, S_n, T_1, T_2, \ldots, T_{n-1}$, and $T_n$ independently represent deuterido [D], hydrido [H], substituted or non-substituted alkyl, or substituted or non-substituted aryl radical;

X and Y independently represent hydrido, formyl [H—C(=O)—], aminocarbonyl [NH$_2$—C(=O)—], aminothiocarbonyl [NH$_2$—C(=S)—], substituted or non-substituted alkyl, substituted or non-substituted aryl, substituted or non-substituted alkylacyl, substituted or non-substituted arylacyl, substituted or non-substituted alkyloxycarbonyl, substituted or non-substituted aryloxycarbonyl, substituted or non-substituted alkylaminocarbonyl, substituted or non-substituted arylaminocarbonyl, substituted or non-substituted alkylaminothiocarbonyl, substituted or non-substituted arylaminothiocarbonyl, substituted or non-substituted alkyloxythiocarbonyl, substituted or non-substituted aryloxythiocarbonyl, substituted or non-substituted alkylsulfonyl, substituted or non-substituted arylsulfonyl, substituted or non-substituted alkylphosphonyl radical, or substituted or non-substituted arylphosphonyl radical;

Z represents hydrido, hydroxy, substituted or non-substituted alkyloxy, substituted or non-substituted aryloxy, substituted or non-substituted amino, substituted or non-substituted alkyl, or substituted or non-substituted aryl radical;

B$_1$, B$_2$, ..., B$_{n-1}$, and B$_n$ are independently selected from natural nucleobases including adenine, thymine, guanine, cytosine and uracil, and unnatural nucleobases; and, at least four of B$_1$, B$_2$, ..., B$_{n-1}$, and B$_n$ are independently selected from unnatural nucleobases with a substituted or non-substituted amino radical covalently linked to the nucleobase moiety.

The compound of Formula I induces the skipping of "exon 4" in the human SCN9A pre-mRNA, yields the human SCN9A mRNA splice variant(s) lacking "exon 4", and therefore is useful to treat pains, or conditions involving Na$_v$1.7 activity.

In some embodiments, of the compound of Formula I, n is an integer selected from 11, 12, 13, 14, 15, 16, 17, 18, 19, 20, 21, 22, 23, and 24.

The compound of Formula I complementarily binds to the 3' splice site spanning the junction of intron 3 and exon 4 within the human SCN9A pre-mRNA read out form the genomic DNA [NCBI Reference Sequence: NC_000002.12]. The 14-mer sequence of [(5'→3') UGUUUAGGUACACU (SEQ ID NO: 2)] within the human SCN9A pre-mRNA is a 3' splice site sequence consisting of 7-mer from "intron 3" and 7-mer from "exon 4". Thus the 14-mer pre-mRNA sequence may be conventionally expressed as [(5'→3') uguuuag|GUACACU (SEQ ID NO: 2)], wherein the intron and exon sequences are denoted with "small" and "capital" letters, respectively, and the junction between "intron 3" and "exon 4" is marked with "|".

The conventional denotation for pre-mRNA is further illustrated by a 30-mer sequence of [(5'→3') gaaucuugu-

DESCRIPTION OF INVENTION

The present invention provides a peptide nucleic acid derivative represented by Formula I, or a pharmaceutically acceptable salt thereof:

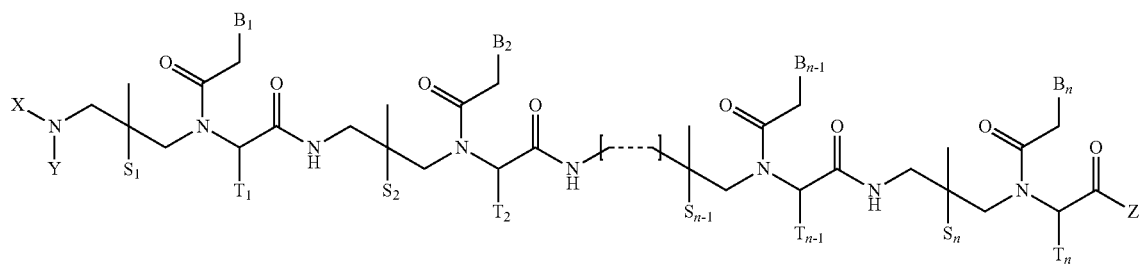

Formula I wherein, n is an integer between 10 and 25;

the compound of Formula I possesses at least a 10-mer complementary overlap with a 14-mer pre-mRNA sequence of [(5'→3') UGUUUAGGUACACU (SEQ ID NO: 2)] within the human SCN9A pre-mRNA;

the compound of Formula I is fully complementary to the human SCN9A pre-mRNA, or partially complementary to the human SCN9A pre-mRNA with one or two mismatches;

S$_1$, S$_2$, ..., S$_{n-1}$, S$_n$, T$_1$, T$_2$, ..., T$_{n-1}$, and T$_n$ independently represent deuterido [D], hydrido [H], substituted or non-substituted alkyl, or substituted or non-substituted aryl radical;

guuuag|GUACACUUUUACUGG (SEQ ID NO: 3)] spanning the junction of "intron 3" and "exon 4" within the human SCN9A pre-mRNA. The exon numbering may vary depending on reported SCN9A mRNA transcripts. Provision of the 30-mer SCN9A sequence is to unequivocally identify the target splice site of the compound of Formula I regardless of the reported exon numbering of the SCN9A mRNA.

Figure 4:
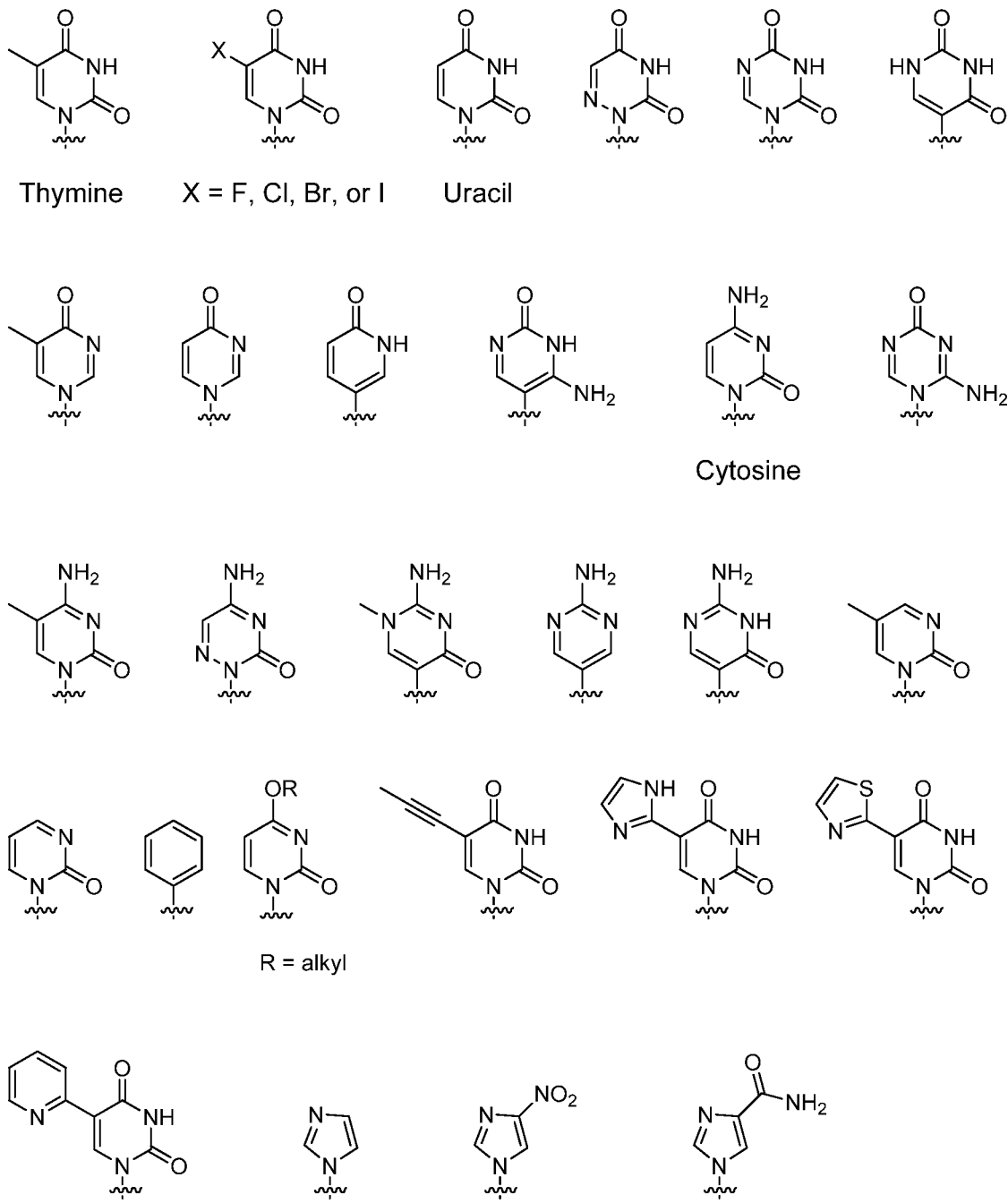
FIG. 4. Examples of natural or unnatural (modified) nucleobases selectable for the peptide nucleic acid derivative of Formula I.

The chemical structures of natural (i.e., naturally occurring) or unnatural (i.e., non-naturally occurring) nucleobases in the PNA derivative of Formula I are exemplified in FIG. 4. Natural or unnatural nucleobases of this invention comprise but are not limited to the nucleobases provided in FIG. 4. Provision of such natural and unnatural nucleobases as examples is to illustrate the diversity of allowable nucleobases, and therefore should not be interpreted to limit the scope of the present invention.

Figure 5A:
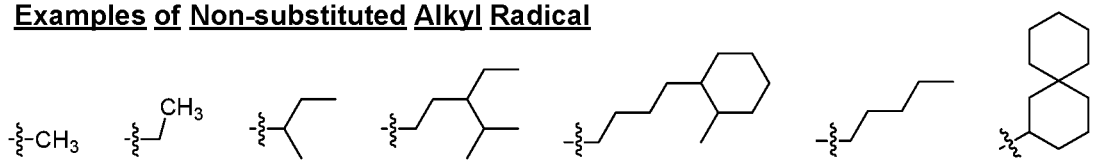
FIG. 5A. Examples for substituted or non-substituted alkyl radicals, which are selectable for the peptide nucleic acid derivative of Formula I.
Figure 5A:
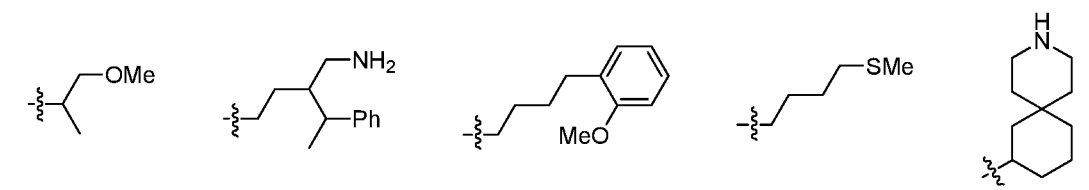
Figure 5A:
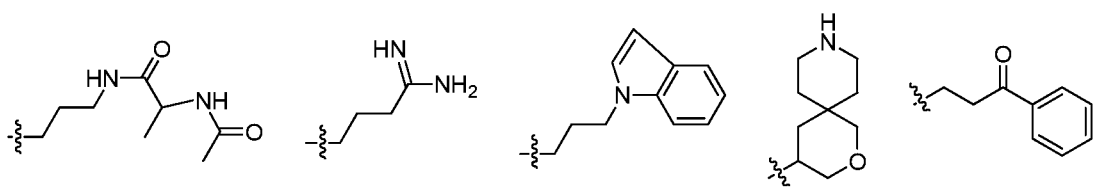
Figure 5A:
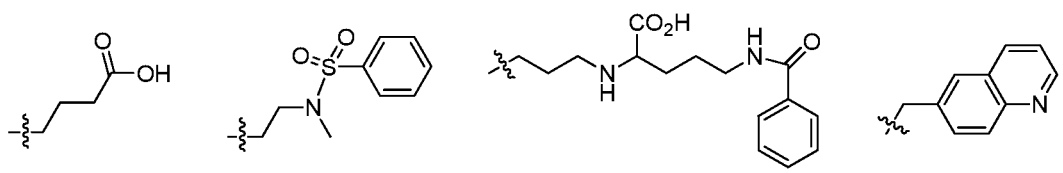
Figure 5A:
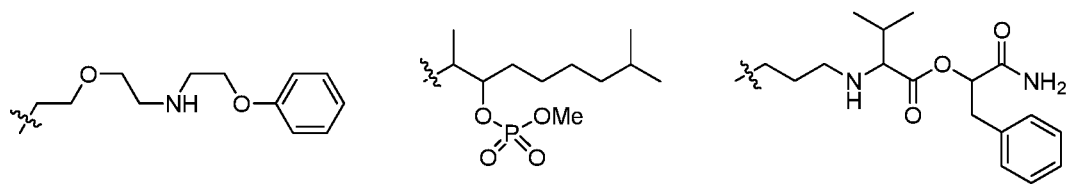
Figure 5B:
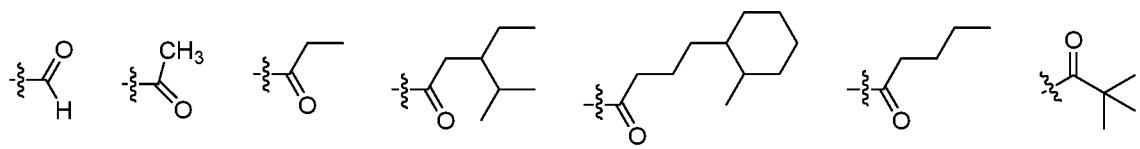
FIG. 5B. Examples for substituted or non-substituted alkylacyl, and substituted or non-substituted arylacyl radicals, which are selectable for the peptide nucleic acid derivative of Formula I.
Figure 5B:
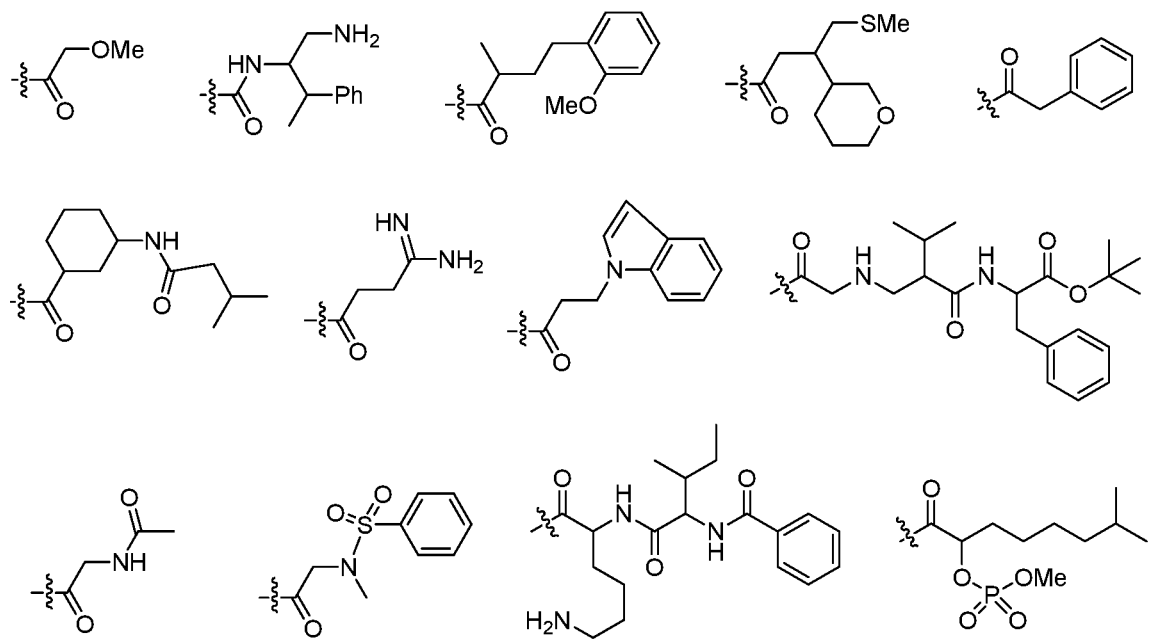
Figure 5B:
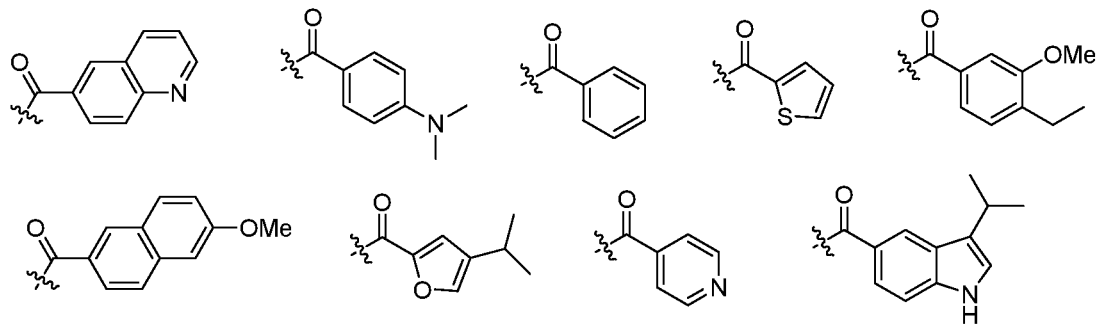
Figure 5C:
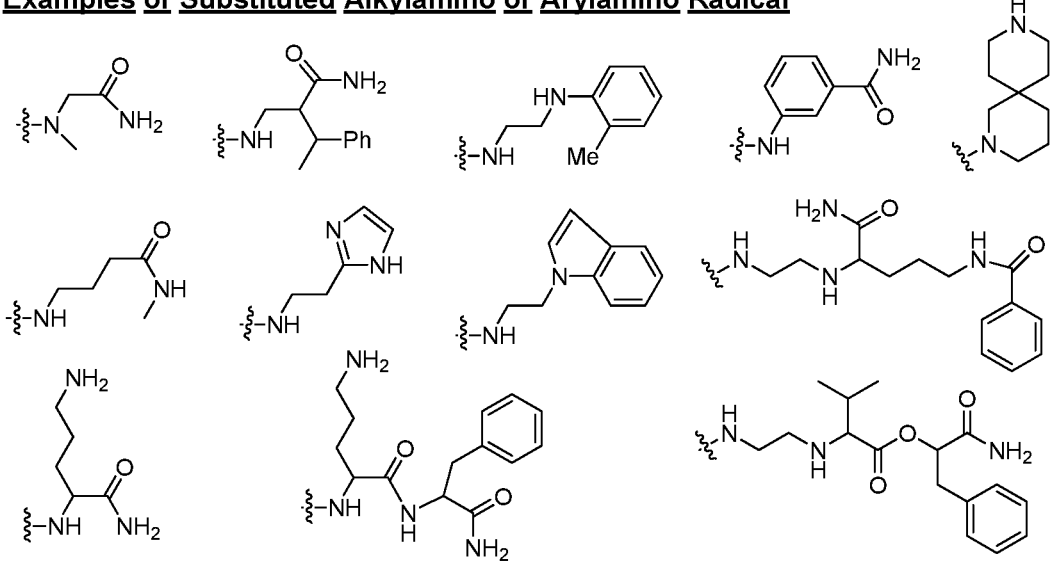
FIG. 5C. Examples for substituted alkylamino, substituted arylamino, substituted or non-substituted aryl, substituted or non-substituted alkylsulfonyl, substituted or non-substituted arylsulfonyl, substituted or non-substituted alkylphosphonyl, and substituted or non-substituted arylphosphonyl radicals, which are selectable for the peptide nucleic acid derivative of Formula I.
Figure 5C:
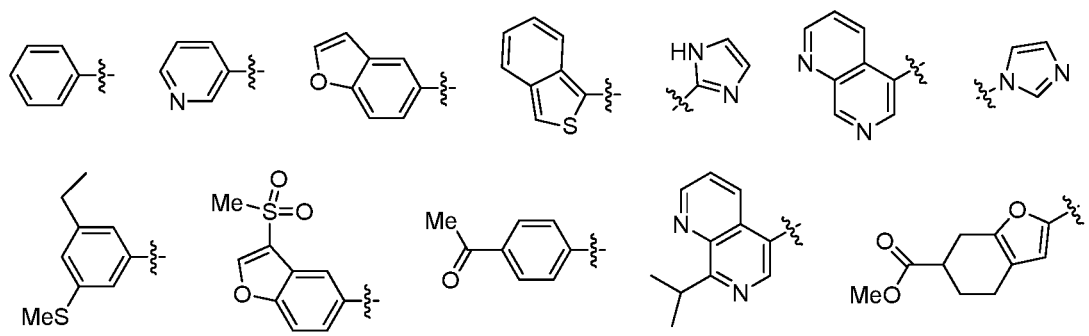
Figure 5C:
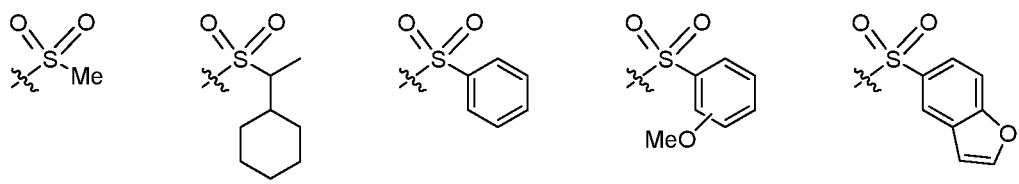
Figure 5C:
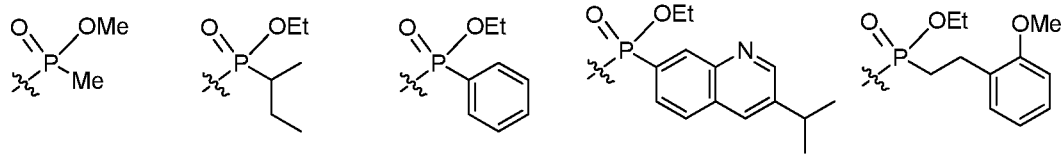
Figure 5D:
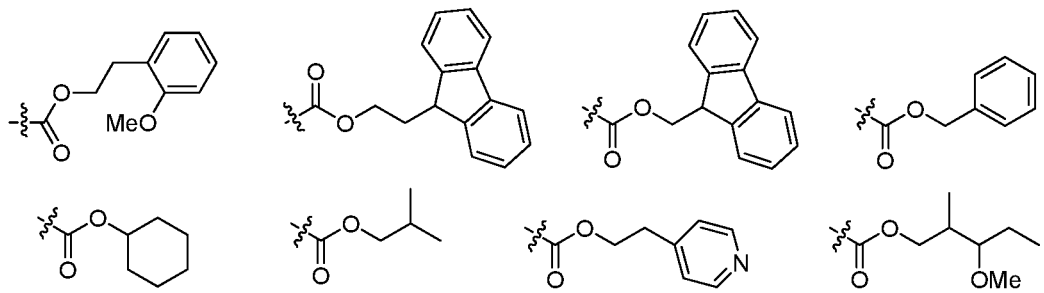
FIG. 5D. Examples for substituted or non-substituted alkyloxycarbonyl, substituted or non-substituted aryloxycarbonyl, substituted or non-substituted alkylaminocarbonyl, and substituted or non-substituted arylaminocarbonyl radicals, which are selectable for the peptide nucleic acid derivative of Formula I.
Figure 5D:
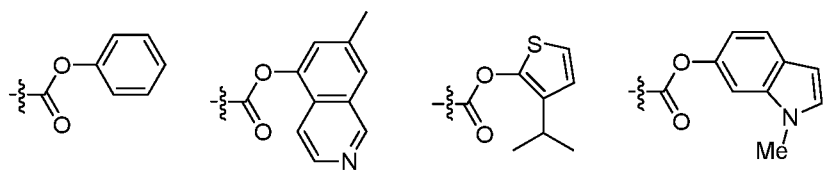
Figure 5D:
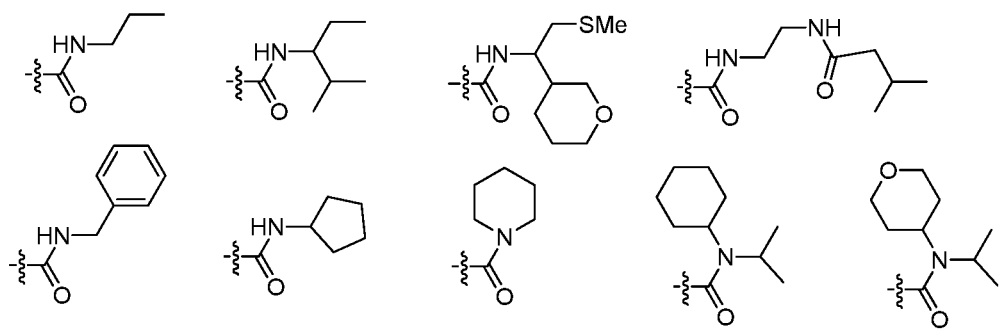
Figure 5D:
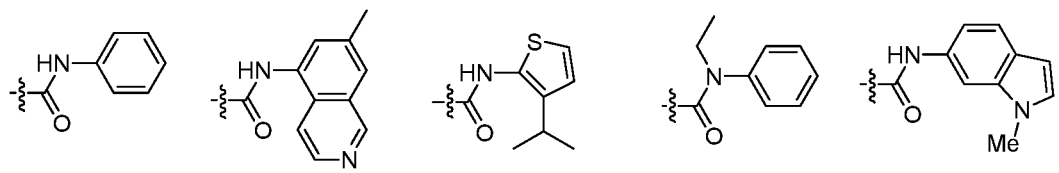
Figure 5E:
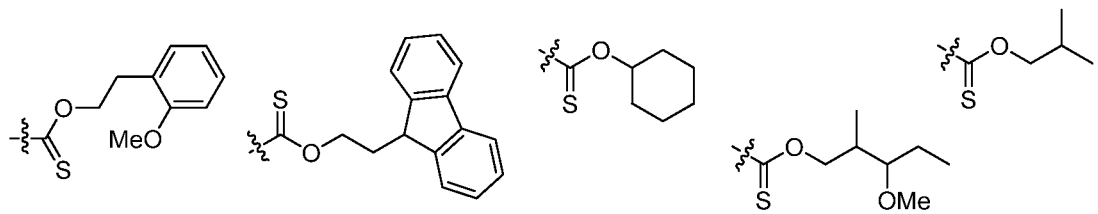
FIG. 5E. Examples for substituted or non-substituted alkyloxythiocarbonyl, substituted or non-substituted alkylaminothiocarbonyl, substituted or non-substituted arylaminothiocarbonyl, and substituted or non-substituted alkyloxythiocarbonyl radicals, which are selectable for the peptide nucleic acid derivative of Formula I.
Figure 5E:
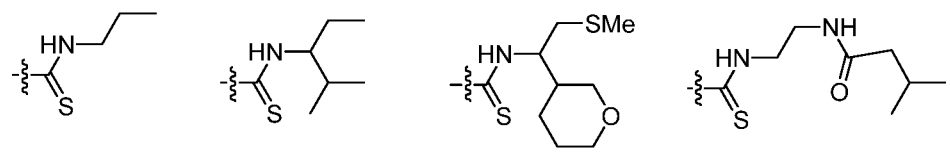
Figure 5E:
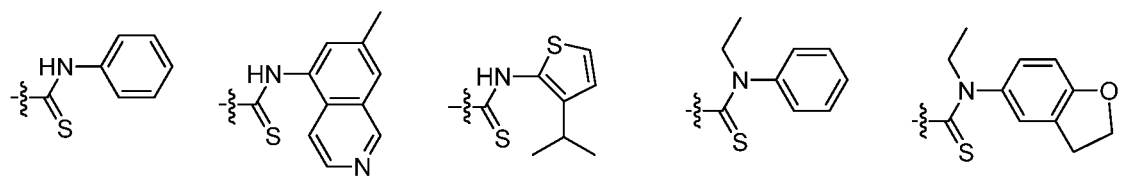
Figure 5E:
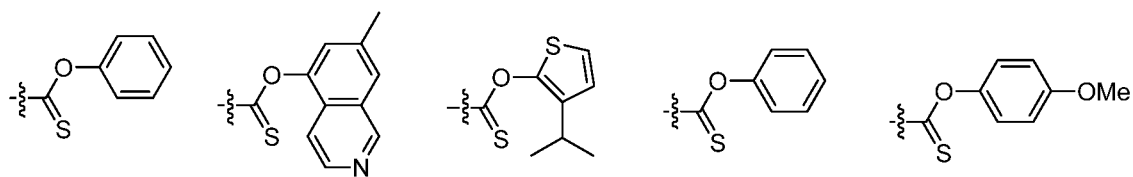

The substituents adopted to describe the PNA derivative of Formula I are exemplified in FIGS. 5A to 5E. FIG. 5A provides examples for substituted or non-substituted alkyl radicals. Substituted or non-substituted alkylacyl and substituted or non-substituted arylacyl radicals are exemplified in FIG. 5B. FIG. 5C illustrates examples for substituted alkylamino, substituted arylamino, substituted or non-substituted aryl, substituted or non-substituted alkylsulfonyl, substituted or non-substituted arylsulfonyl, substituted or non-substituted alkylphosphonyl, and substituted or non-substituted arylphosphonyl radicals. FIG. 5D provides examples for substituted or non-substituted alkyloxycarbonyl, substituted or non-substituted aryloxycarbonyl, substituted or non-substituted alkylaminocarbonyl, and substituted or non-substituted arylaminocarbonyl radicals. In FIG. 5E, are provided examples for substituted or non-substituted alkyloxythiocarbonyl, substituted or non-substituted alkylaminothiocarbonyl, substituted or non-substituted arylaminothiocarbonyl, and substituted or non-substituted alkyloxythiocarbonyl radicals. Provision of such substituents as examples is to illustrate the diversity of allowable substituents, and therefore should not be interpreted to limit the scope of the present invention. A skilled person in the field may readily figure out that the oligonucleotide sequence is the overriding factor for sequence specific binding of oligonucleotide to the target pre-mRNA sequence over substituents in the N-terminus or C-terminus.

The compound of Formula I tightly binds to the complementary DNA as exemplified in the prior art [PCT/KR2009/001256]. The duplex between the PNA derivative of Formula I and its full-length complementary DNA or RNA possesses a $T_m$ value too high to be reliably determined in aqueous buffer. The PNA compound of Formula I yields high $T_m$ values with complementary DNAs of shorter length.

The compound of Formula I tightly binds to the target 3' splice site of the human SCN9A pre-mRNA transcribed from the human SCN9A gene, and interferes with the formation of "splicesome early complex" involving the compound's target exon. Since the compound of this invention sterically inhibits the formation of "splicesome early complex", the SCN9A "exon 4" is spliced out to yield SCN9A mRNA splice variant(s) lacking "exon 4". Consequently the compound of this invention induces the skipping of "exon 4" in the SCN9A mRNA.

Owing to the said compound's strong affinity for the complementary pre-mRNA sequence, the compound of this invention may also tightly bind to a partially complementary pre-mRNA sequence with one or two mismatches, and induce the skipping of the target exon within the SCN9A pre-mRNA. For example even if a 14-mer PNA derivative of Formula I possesses a single mismatch with the SCN9A pre-mRNA, the 14-mer SCN9A ASO still induces the skipping of "exon 4" in the SCN9A mRNA.

The compound of Formula I possesses good cell permeability and can be readily delivered into cell as "naked" oligonucleotide as exemplified in the prior art [PCT/KR2009/001256]. Thus the compound of this invention induces the skipping of "exon 4" in the SCN9A pre-mRNA to yield SCN9A mRNA splice variant(s) lacking SCN9A "exon 4" in cells treated with the compound of Formula I as "naked" oligonucleotide. The said compound does not require any means or formulations for delivery into cell to potently induce the skipping of the target exon in cells. The compound of Formula I readily induces the skipping of the SCN9A "exon 4" in cells treated with the compound of this invention as "naked" oligonucleotide at sub-femtomolar concentration.

Cells treated with the compound of Formula I as "naked oligonucleotide" express a lower level of the full-length SCN9A mRNA, and therefore show weaker $Na_v1.7$ functional activity than cells without the compound treatment. The compound of Formula I inhibits $Na_v1.7$ expression in neuronal cells or tissues upon systemic administration as "naked oligonucleotide". Thus the said compound is useful to treat pains, or disorders involving excessive expression of $Na_v1.7$.

The PNA derivative of Formula I can be systemically administered as "naked" oligonucleotide to induce the skipping of the SCN9A "exon 4" in target tissues, and therefore inhibit the expression of the full-length SCN9A mRNA. The compound of Formula I does not require a particular formulation to increase the systemic delivery to target tissues for the intended therapeutic or biological activity. Usually the compound of Formula I is dissolved in PBS or saline, and systemically administered to elicit the desired therapeutic activity in target tissues. The compound of this invention does not need to be heavily or invasively formulated to elicit the systemic therapeutic activity.

The compound of Formula I may be used as combined with a pharmaceutically acceptable acid or base including but not limited to sodium hydroxide, potassium hydroxide, hydrochloric acid, methanesulfonic acid, citric acid, trifluoroacetic acid, and so on.

The PNA derivative of Formula I or a pharmaceutically acceptable salt thereof can be administered to a subject in combination with a pharmaceutically acceptable adjuvant including but not limited to citric acid, hydrochloric acid, tartaric acid, stearic acid, polyethyleneglycol, polypropyleneglycol, ethanol, isopropanol, sodium bicarbonate, distilled water, preservative(s), and so on.

The compound of the present invention can be systemically administered to a subject at a therapeutic dose of 1 fmole/Kg to higher than 1 nmole/Kg, which would vary depending on the dosing schedule, conditions or situations of the subject, and so on.

Preferred is a PNA derivative of Formula I, or a pharmaceutically acceptable salt thereof:
wherein,
n is an integer between 10 and 25;
the compound of Formula I possesses at least a 10-mer complementary overlap with the 14-mer pre-mRNA sequence of [(5'→3') UGUUUAGGUACACU (SEQ ID NO: 2)] within the human SCN9A pre-mRNA;
the compound of Formula I is fully complementary to the human SCN9A pre-mRNA, or partially complementary to the human SCN9A pre-mRNA with one or two mismatches;

$S_1, S_2, \ldots, S_{n-1}, S_n, T_1, T_2, \ldots, T_{n-1},$ and $T_n$ independently represent deuterido, hydrido, substituted or non-substituted alkyl, or substituted or non-substituted aryl radical;

X and Y independently represent hydrido, formyl, aminocarbonyl, aminothiocarbonyl, substituted or non-substituted alkyl, substituted or non-substituted aryl, substituted or non-substituted alkylacyl, substituted or non-substituted arylacyl, substituted or non-substituted alkyloxycarbonyl, substituted or non-substituted aryloxycarbonyl, substituted or non-substituted alkylaminocarbonyl, substituted or non-substituted arylaminocarbonyl, substituted or non-substituted alkylaminothiocarbonyl, substituted or non-substituted arylaminothiocarbonyl, substituted or non-substituted alkyloxythiocarbonyl, substituted or non-substituted aryloxythiocarbonyl, substituted or non-substituted alkylsulfonyl, substituted or non-substituted arylsulfonyl, substituted or non-substituted alkylphosphonyl radical, or substituted or non-substituted arylphosphonyl radical;

Z represents hydrido, hydroxy, substituted or non-substituted alkyloxy, substituted or non-substituted aryloxy, substituted or non-substituted amino, substituted or non-substituted alkyl, or substituted or non-substituted aryl radical;

$B_1, B_2, \ldots, B_{n-1},$ and $B_n$ are independently selected from natural nucleobases including adenine, thymine, guanine, cytosine and uracil, and unnatural nucleobases; and, at least four of $B_1, B_2, \ldots, B_{n-1},$ and $B_n$ are independently selected from unnatural nucleobases represented by Formula II, Formula III, or Formula IV:

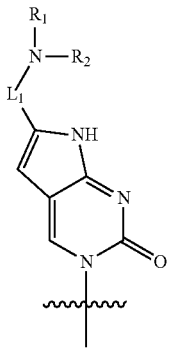

Formula II

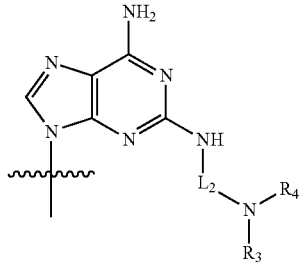

Formula III

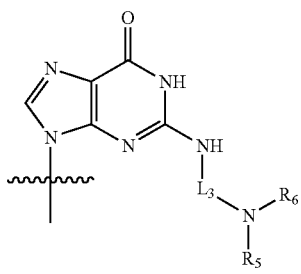

Formula IV wherein, $R_1, R_2, R_3, R_4, R_5$ and $R_6$ are independently selected from hydrido, and substituted or non-substituted alkyl radical;

$L_1, L_2$ and $L_3$ are a covalent linker represented by Formula V covalently linking the basic amino group to the nucleobase moiety:

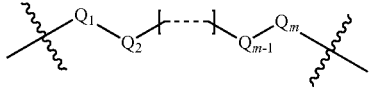

Formula V wherein, $Q_1$ and $Q_m$ are substituted or non-substituted methylene (—CH$_2$—) radical, and $Q_m$ is directly linked to the basic amino group;

$Q_2, Q_3, \ldots,$ and $Q_{m-1}$ are independently selected from substituted or non-substituted methylene, oxygen (—O—), sulfur (—S—), and substituted or non-substituted amino radical [—N(H)—, or —N(substituent)-]; and, m is an integer between 1 and 15.

In certain such embodiments, $S_1, S_2, \ldots, S_{n-1}, S_n, T_1, T_2, \ldots, T_{n-1},$ and $T_n$ independently represent deuterido or hydrido radical and Z represents hydrido, hydroxy, substituted or non-substituted alkyloxy, substituted or non-substituted aryloxy, or substituted or non-substituted amino radical. In other such embodiments, at least one of $S_1, S_2, \ldots, S_{n-1}, S_n, T_1, T_2, \ldots, T_{n-1},$ and $T_n$ independently represents substituted or non-substituted alkyl, or substituted or non-substituted aryl radical, and/or Z represents substituted or non-substituted alkyl or substituted or non-substituted aryl radical.

In some embodiments, m in Formula V an integer selected from 2, 3, 4, 5, 6, 7, 8, 9, 10, 11, 12, 13, and 14.

Of interest is a PNA oligomer of Formula I, or a pharmaceutically acceptable salt thereof:

wherein, n is an integer between 11 and 21;

the compound of Formula I possesses at least a 10-mer complementary overlap with the 14-mer pre-mRNA sequence of [(5'→3') UGUUUAGGUACACU (SEQ ID NO: 2)] within the human SCN9A pre-mRNA;

the compound of Formula I is fully complementary to the human SCN9A pre-mRNA, or partially complementary to the human SCN9A pre-mRNA with one or two mismatches;

$S_1, S_2, \ldots, S_{n-1}, S_n, T_1, T_2, \ldots, T_{n-1},$ and $T_n$ are hydrido radical;

X and Y independently represent hydrido, substituted or non-substituted alkyl, substituted or non-substituted aryl, substituted or non-substituted alkylacyl, substituted or non-substituted arylacyl, substituted or non-substituted alkyloxycarbonyl, substituted or non-substituted aryloxycarbonyl, substituted or non-substituted alkylaminocarbonyl, substituted or non-substituted arylaminocarbonyl, substituted or non-substituted alkylsulfonyl, or substituted or non-substituted arylsulfonyl radical;

Z represents substituted or non-substituted amino radical;

$B_1, B_2, \ldots, B_{n-1},$ and $B_n$ are independently selected from natural nucleobases including adenine, thymine, guanine, cytosine and uracil, and unnatural nucleobases;

at least four of $B_1, B_2, \ldots, B_{n-1},$ and $B_n$ are independently selected from unnatural nucleobases represented by Formula II, Formula III, or Formula IV;

$R_1, R_2, R_3, R_4, R_5$ and $R_6$ are independently selected from hydrido, and substituted or non-substituted alkyl radical;

$Q_1$ and $Q_m$ are substituted or non-substituted methylene radical, and $Q_m$ is directly linked to the basic amino group;

$Q_2, Q_3, \ldots,$ and $Q_{m-1}$ are independently selected from substituted or non-substituted methylene, oxygen, and amino radical; and, m is an integer between 1 and 11.

In one embodiment of the PNA oligomer of Formula I, or a pharmaceutically acceptable salt thereof, X and Y independently represent hydrido, substituted or non-substituted alkyl, substituted or non-substituted aryl, substituted or non-substituted alkylacyl, substituted or non-substituted arylacyl, substituted or non-substituted alkyloxycarbonyl, or substituted or non-substituted aryloxycarbonyl radical.

In another embodiment of the PNA oligomer of Formula I, or a pharmaceutically acceptable salt thereof, at least one of X and Y independently represents substituted or non-substituted alkylaminocarbonyl, substituted or non-substituted arylaminocarbonyl, substituted or non-substituted alkylsulfonyl, or substituted or non-substituted arylsulfonyl radical.

Of particular interest is a PNA derivative of Formula I, or a pharmaceutically acceptable salt thereof:

wherein, n is an integer between 11 and 19;

the compound of Formula I possesses at least a 10-mer complementary overlap with the 14-mer pre-mRNA sequence of [(5'→3') UGUUUAGGUACACU (SEQ ID NO: 2)] within the human SCN9A pre-mRNA;

the compound of Formula I is fully complementary to the human SCN9A pre-mRNA;

$S_1, S_2, \ldots, S_{n-1}, S_n, T_1, T_2, \ldots, T_{n-1},$ and $T_n$ are hydrido radical;

X and Y independently represent hydrido, substituted or non-substituted alkyl, substituted or non-substituted aryl, substituted or non-substituted alkylacyl, substituted or non-substituted arylacyl, substituted or non-substituted alkyloxycarbonyl, substituted or non-substituted alkylaminocarbonyl, substituted or non-substituted alkylsulfonyl, or substituted or non-substituted arylsulfonyl radical;

Z represents substituted or non-substituted amino radical;

$B_1, B_2, \ldots, B_{n-1},$ and $B_n$ are independently selected from natural nucleobases including adenine, thymine, guanine, cytosine and uracil, and unnatural nucleobases;

at least four of $B_1, B_2, \ldots, B_{n-1},$ and $B_n$ are independently selected from unnatural nucleobases represented by Formula II, Formula III, or Formula IV;

$R_1, R_2, R_3, R_4, R_5$ and $R_6$ are independently selected from hydrido, and substituted or non-substituted alkyl radical;

$Q_1$ and $Q_m$ are methylene radical, and $Q_m$ is directly linked to the basic amino group;

$Q_2, Q_3, \ldots,$ and $Q_{m-1}$ are independently selected from methylene, oxygen, and amino radical; and, m is an integer between 1 and 9.

In one embodiment of the PNA oligomer of Formula I, or a pharmaceutically acceptable salt thereof, X and Y independently represent hydrido, substituted or non-substituted alkylacyl, or substituted or non-substituted alkyloxycarbonyl radical.

In another embodiment of the PNA oligomer of Formula I, or a pharmaceutically acceptable salt thereof, at least one of X and Y independently represents substituted or non-substituted alkyl, substituted or non-substituted aryl, substituted or non-substituted arylacyl, substituted or non-substituted alkylaminocarbonyl, substituted or non-substituted alkylsulfonyl, or substituted or non-substituted arylsulfonyl radical.

Of high interest is a PNA oligomer of Formula I, or a pharmaceutically acceptable salt thereof:

wherein, n is an integer between 11 and 19;

the compound of Formula I possesses at least a 10-mer complementary overlap with the 14-mer pre-mRNA sequence of [(5'→3') UGUUUAGGUACACU (SEQ ID NO: 2)] within the human SCN9A pre-mRNA;

the compound of Formula I is fully complementary to the human SCN9A pre-mRNA;

$S_1, S_2, \ldots, S_{n-1}, S_n, T_1, T_2, \ldots, T_{n-1},$ and $T_n$ are hydrido radical;

X and Y independently represent hydrido, substituted or non-substituted alkyl, substituted or non-substituted aryl, substituted or non-substituted alkylacyl, substituted or non-substituted arylacyl, or substituted or non-substituted alkyloxycarbonyl radical;

Z represents substituted or non-substituted amino radical;

$B_1, B_2, \ldots, B_{n-1},$ and $B_n$ are independently selected from natural nucleobases including adenine, thymine, guanine, cytosine and uracil, and unnatural nucleobases;

at least four of $B_1, B_2, \ldots, B_{n-1},$ and $B_n$ are independently selected from unnatural nucleobases represented by Formula II, Formula III, or Formula IV;

$R_1, R_3,$ and $R_5$ are hydrido radical, and $R_2, R_4,$ and $R_6$ independently represent hydrido, or substituted or non-substituted alkyl radical;

$Q_1$ and $Q_m$ are methylene radical, and $Q_m$ is directly linked to the basic amino group;

$Q_2, Q_3, \ldots,$ and $Q_{m-1}$ are independently selected from methylene, oxygen radical; and, m is an integer between 1 and 8.

In one embodiment of the PNA oligomer of Formula I, or a pharmaceutically acceptable salt thereof, X and Y independently represent hydrido, substituted or non-substituted alkylacyl, or substituted or non-substituted alkyloxycarbonyl radical.

In another embodiment of the PNA oligomer of Formula I, or a pharmaceutically acceptable salt thereof, at least one of X and Y independently represents substituted or non-substituted alkyl, substituted or non-substituted aryl, or substituted or non-substituted arylacyl.

Of higher interest is a PNA derivative of Formula I, or a pharmaceutically acceptable salt thereof:

wherein, n is an integer between 11 and 19;

the compound of Formula I possesses at least a 10-mer complementary overlap with the 14-mer pre-mRNA sequence of [(5'→3') UGUUUAGGUACACU (SEQ ID NO: 2)] within the human SCN9A pre-mRNA;

the compound of Formula I is fully complementary to the human SCN9A pre-mRNA;

$S_1, S_2, \ldots, S_{n-1}, S_n, T_1, T_2, \ldots, T_{n-1},$ and $T_n$ are hydrido radical;

X and Y independently represent hydrido, substituted or non-substituted alkylacyl, substituted or non-substituted arylacyl, or substituted or non-substituted alkyloxycarbonyl radical;

Z represents substituted or non-substituted amino radical;

$B_1, B_2, \ldots, B_{n-1},$ and $B_n$ are independently selected from adenine, thymine, guanine, cytosine, and unnatural nucleobases;

at least five of $B_1, B_2, \ldots, B_{n-1},$ and $B_n$ are independently selected from unnatural nucleobases represented by Formula II, Formula III, or Formula IV;

$R_1, R_2, R_3, R_4, R_5,$ and $R_6$ are hydrido radical;

$Q_1$ and $Q_m$ are methylene radical, and $Q_m$ is directly linked to the basic amino group;

$Q_2, Q_3, \ldots$, and $Q_{m-1}$ are independently selected from methylene, and oxygen radical; and, m is an integer between 1 and 8.

In one embodiment of the PNA oligomer of Formula I, or a pharmaceutically acceptable salt thereof, X and Y independently represent hydrido, substituted or non-substituted alkylacyl, or substituted or non-substituted alkyloxycarbonyl radical.

In one embodiment of the PNA oligomer of Formula I, or a pharmaceutically acceptable salt thereof, at least one of X and Y independently represents substituted or non-substituted arylacyl radical.

Of highest interest is a PNA derivative of Formula I, or a pharmaceutically acceptable salt thereof:

wherein, n is an integer between 11 and 19;

the compound of Formula I possesses at least a 10-mer complementary overlap with the 14-mer pre-mRNA sequence of [(5'→3') UGUUUAGGUACACU (SEQ ID NO: 2)] within the human SCN9A pre-mRNA;

the compound of Formula I is fully complementary to the human SCN9A pre-mRNA;

$S_1, S_2, \ldots, S_{n-1}, S_n, T_1, T_2, \ldots, T_{n-1}$, and $T_n$ are hydrido radical;

X is hydrido radical;

Y represents substituted or non-substituted alkylacyl, substituted or non-substituted arylacyl, or substituted or non-substituted alkyloxycarbonyl radical;

Z represents substituted or non-substituted amino radical;

$B_1, B_2, \ldots, B_{n-1}$, and $B_n$ are independently selected from adenine, thymine, guanine, cytosine, and unnatural nucleobases;

at least five of $B_1, B_2, \ldots, B_{n-1}$, and $B_n$ are independently selected from unnatural nucleobases represented by Formula II, Formula III, or Formula IV;

$R_1, R_2, R_3, R_4, R_5$, and $R_6$ are hydrido radical;

$L_1$ represents —$(CH_2)_2$—O—$(CH_2)_2$—, —$CH_2$—O—$(CH_2)_2$—, —$CH_2$—O—$(CH_2)_3$—, —$CH_2$—O—$(CH_2)_4$—, or —$CH_2$—O—$(CH_2)_5$— with the right end is directly linked to the basic amino group; and, $L_2$ and $L_3$ are independently selected from —$(CH_2)_2$—, —$(CH_2)_3$—, —$(CH_2)_4$—, —$(CH_2)_5$—, —$(CH_2)_6$—, —$(CH_2)_7$—, —$(CH_2)_8$—, —$(CH_2)_2$—O—$(CH_2)_2$—, —$(CH_2)_3$—O—$(CH_2)_2$—, and —$(CH_2)_2$—O—$(CH_2)_3$— with the right end is directly linked to the basic amino group.

In one embodiment of the PNA oligomer of Formula I, or a pharmaceutically acceptable salt thereof, Y represents substituted or non-substituted alkylacyl or substituted or non-substituted alkyloxycarbonyl radical.

In another embodiment of the PNA oligomer of Formula I, or a pharmaceutically acceptable salt thereof, Y represents substituted or non-substituted arylacyl.

Of specific interest is a PNA derivative of Formula I which is selected from the group of compounds provided below, or a pharmaceutically acceptable salt thereof:

(N → C) Fethoc-TA(5)A-A(5)AG(6)-TG(6)T-A(5)CC(102)-TA(5)A-A(5)-NH$_2$;

(N → C) Fethoc-TA(5)A-A(4)AG(6)-TG(6)T-A(5)CC(103)-TA(5)A-A-NH$_2$;

(N → C) Fmoc-TA(5)A-A(4)AG(6)-TG(6)T-A(5)CC(103)-TA(5)A-A-NH$_2$;

(N → C) Piv-Leu-TA(5)A-A(5)AG(302)-TG(6)T-A(5)CC(102)-TA(5)A-A(5)-NH$_2$;

(N → C) Fethoc-TA(5)T-A(5)AG(6)-TG(6)T-A(5)CC(102)-TA(5)A-A(5)-NH$_2$;

(N → C) Benzoyl-Gly-TA(202)A-A(5)AG(6)-TG(6)T-A(5)CT-TA(5)A-Lys-NH$_2$;

(N → C) Fethoc-AA(5)G-TG(6)T-A(5)CC(102)-TAA(5)-A-NH$_2$;

(N → C) Fethoc-AA(5)G-CG(6)T-A(5)CC(102)-TAA(5)-A-NH$_2$;

(N → C) Fmoc-AA(5)G-TG(6)T-A(5)CC(102)-TAA(5)-A-NH$_2$;

(N → C) Benzenesulfonyl-AA(5)G-TG(6)T-A(5)CC(102)-TAA(5)-A-NH$_2$;

(N → C) Ac-AA(5)G-TG(6)T-A(5)CC(102)-TAA(5)-A-NH$_2$;

(N → C) Fethoc-AA(5)G-TG(5)T-A(5)CC(102)-TA(3)A-A(5)-NH$_2$;

(N → C) Fmoc-AA(5)G-TG(6)T-AC(102)C-TAA(5)-A-NH$_2$;

(N → C) Methyl-AA(5)G-TG(5)T-A(5)CC(102)-TA(3)A-A(5)-Gly-Arg-NH$_2$;

(N → C) Fethoc-A(5)AG-TG(6)T-A(5)CC(102)-TAA-A(5)-NH$_2$;

(N → C) Ac-Val-A(5)AG-TG(6)T-A(5)CC(102)-TAA-A(5)-NH$_2$;

(N → C) Fethoc-AAG(6)-TG(6)T-A(5)CC(102)-TA(5)A-A-NH$_2$;

(N → C) Fethoc-AA(5)G-TG(5)T-A(5)CC(102)-TA(5)A-A(5)-NH$_2$, (N → C) Fethoc-AA(5)G-TG(5)T-A(5)CC(102)-TA(5)A-A(5)C-NH$_2$;

(N → C) Fethoc-AA(5)G-TG(5)T-A(5)AC(102)-TA(5)T-A(5)C-NH$_2$;

(N → C) H-AA(5)G-TG(202)T-A(5)CC(102)-TA(5)A-A(5)C-NH$_2$;

(N → C) Fethoc-Lys-Leu-AA(5)G-TG(5)T-A(5)CC(102)-TA(202)A-A(5)C-Lys-NH$_2$;

(N → C) [N-(2-Phenylethyl)amino]carbonyl-AA(3)G-TG(5)T-A(5)CC(105)-TA(5)A-A(5)C-NH$_2$;

(N → C) N,N-Phenyl-Me-AA(5)G-TG(5)T-A(5)CC(102)-TA(5)A-A(4)C-NH$_2$;

(N → C) Fethoc-AA(5)G-TA(5)T-A(5)CC(102)-TG(5)A-A(5)C-NH$_2$;

(N → C) p-Toluenesulfonyl-AA(5)G-TG(5)T-A(5)CC(102)-TA(5)A-A(5)C-NH$_2$;

(N → C) p-Toluenesulfonyl-AA(5)G-TG(203)T-A(5)CC(102)-TA(5)A-A(5)C-Lys-NH$_2$;

(N → C) Fethoc-AA(5)G-TG(203)T-A(5)CC(103)-TA(7)A-A(5)C-NH$_2$;

(N → C) n-Propyl-AA(5)G-TG(5)T-A(5)CC(103)-TA(5)A-A(5)C-NH$_2$;

(N → C) Benzoyl-AA(5)G-TG(5)T-A(5)CC(102)-TA(5)A-A(5)C-NH$_2$;

(N → C) Benzyl-AA(5)G-TG(5)T-A(5)CC(103)-TA(5)A-A(5)C-NH$_2$;

(N → C) Benzoyl-AA(5)G-TG(3)T-A(5)CC(202)-TA(5)A-A(5)C-NH$_2$;

(N → C) Fethoc-AA(5)G-TG(5)T-A(5)CC(102)-TA(5)A-A(5)C-Leu-Lys-NH$_2$;

(N → C) Piv-AA(5)G-TG(5)T-A(5)CC(102)-TA(5)A-A(5)C-NH$_2$;

(N → C) Fethoc-TA(5)G-TG(5)T-A(5)CC(102)-TA(5)A-A(5)C-NH$_2$;

(N → C) Fethoc-AA(5)C-TG(5)T-A(5)CC(102)-TA(5)A-A(5)C-NH$_2$;

(N → C) Methylsulfonyl-AA(5)G-TG(5)T-A(5)CC(102)-TA(5)A-A(5)C-NH$_2$;

(N → C) n-Hexyl-AA(5)G-TG(5)T-A(5)CC(102)-TA(5)A-A(5)C-NH$_2$;

(N → C) n-Hexanoyl-AA(5)G-TG(5)T-A(5)CC(102)-TA(5)A-A(5)C-NH$_2$;

(N → C) n-Hexanoyl-AA(5)G-TG(5)T-A(5)CC(102)-TA(8)A-A(5)C-NH$_2$;

(N → C) Fethoc-AA(3)G-TG(202)T-A(5)CC(102)-TA(5)A-A(5)C-NH$_2$;

(N → C) Fethoc-AA(3)G-TG(202)T-A(5)CC(103)-TA(5)A-A(5)C-NH$_2$;

(N → C) Fethoc-AA(3)G-TG(202)T-A(5)CC(202)-TA(5)A-A(5)C-NH$_2$;

(N → C) FAM-HEX-HEX-AA(3)G-TG(202)T-A(5)CC(202)-TA(5)A-A(5)C-NH$_2$;

(N → C) Fethoc-A(5)GT-G(5)TA(5)-CC(102)T-A(5)AA(5)-C-NH$_2$;

(N → C) Fethoc-AG(5)T-G(7)TA-CC(102)T-AA(6)A-C-NH$_2$;

(N → C) Fethoc-AA(6)G-TG(5)T-A(6)CC(102)-TA(6)A-A(6)C-NH$_2$;

(N → C) Fethoc-AA(5)G-TG(5)T-A(5)CC(102)-TA(5)A-A(3)CA-C(105)AA-NH$_2$;

(N → C) Fethoc-AA(5)G-TCT-A(5)CC(102)-TA(5)A-A(3)CA-C(105)AA-NH$_2$;

(N → C) Fethoc-AA(5)G-TCT-A(5)CC(102)-TA(5)A-A(3)CA(3)-CTA-NH$_2$;

(N → C) Fethoc-TG(5)T-A(5)CC(102)-TA(5)A-A(3)CA-CA(7)A-NH$_2$;

(N → C) Fethoc-AA(5)G-TG(5)T-A(5)CC(102)-TA(5)A-A(3)CA(5)-C-NH$_2$;

(N → C) Fethoc-TG(5)T-A(5)CC(102)-TA(5)A-A(3)CA(5)-C-NH$_2$;

(N → C) p-Toluenesulfonyl-TG(203)T-A(5)CC(102)-TA(5)A-A(3)CA-C-Lys-NH$_2$;

(N → C) Fethoc-TG(5)T-A(5)CC(202)-TA(5)A-A(3)CA-CA(5)A-NH$_2$;

(N → C) Piv-TG(5)T-A(5)CC(202)-TA(5)A-A(3)CA-CA(5)A-NH$_2$;

(N → C) Benzoyl-TG(5)T-A(5)CC(202)-TA(5)A-A(3)CA-CA(5)A-NH$_2$;

(N → C) Propionyl-TG(5)T-A(5)CC(202)-TA(5)A-A(3)CA-CA(5)A-NH$_2$;

(N → C) Fethoc-TG(5)T-A(5)CC(202)-TA(5)A-A(3)CA-CA(5)A-Arg-Val-NH$_2$;

(N → C) Fethoc-AA(5)G-TG(5)T-A(5)CC(102)-TA(5)A-A(5)G-NH$_2$;

(N → C) Fethoc-AG(5)-TG(5)T-A(5)CC(102)-TA(5)A-A(5)G-NH$_2$;

(N → C) Fethoc-AA(5)G-TG(5)T-A(5)CC(102)-TA(5)A-A(5)CA-NH$_2$;

(N → C) Fethoc-AA(5)G-TG(5)T-A(5)CC(102)-TA(5)A-A(5)GG-NH$_2$;

and,

-continued (N → C) Fethoc-AA(5)G-TG(5)T-ACC(1O2)-TA(5)A-A(5)CA(5)-C-NH$_2$:

wherein,

A, G, T, and C are PNA monomers with a natural nucleobase of adenine, guanine, thymine, and cytosine, respectively;

C(pOq), A(p), A(pOq), G(p), and G(pOq) are PNA monomers with an unnatural nucleobase represented by Formula VI, Formula VII, Formula VIII, Formula IX, and Formula X, respectively;

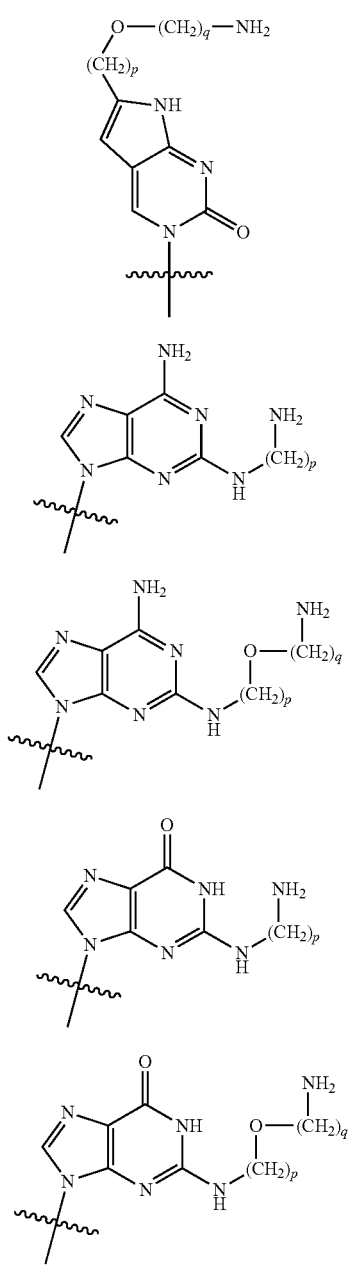

Formula VI

Formula VII

Formula VIII

Formula IX

Formula X wherein,
p and q are integers; and,
the abbreviations for the N- and C-terminus substituents are specifically defined as follows: "Fmoc-" is the abbreviation for "[(9-fluorenyl)methyloxy]carbonyl-"; "Fethoc-" for "[2-(9-fluorenyl)ethyl-1-oxy]carbonyl"; "Ac-" for "acetyl-"; "n-Hexanoyl-" for "1-(n-hexanoyl-"; "Benzoyl-" for "benzenecabonyl-"; "Piv-" for "pivalyl-"; "n-Propyl-" for "1-(n-propyl)-"; "n-Hexyl-" for "1-(n-hexyl)-"; "H-" for "hydrido-"; "p-Toluenesulfonyl" for "(4-methylbenzene)-1-sulfonyl-"; "Benzenesulfonyl" for "benzene-1-sulfonyl-"; "Methylsulfonyl" for "methyl-1-sulfonyl-"; "-Lys-" for amino acid residue "lysine"; "-Val-" for amino acid residue "valine"; "-Leu-" for amino acid residue "leucine"; "-Arg-" for amino acid residue "arginine"; "-Gly-" for amino acid residue "glycine"; "[N-(2-Phenylethyl)amino]carbonyl-" for "[N-1-(2-phenylethyl)-amino]carbonyl-"; "Benzyl-" for "1-(phenyl)methyl-"; "Phenyl-" for "phenyl-"; "Me-" for "methyl-"; "-HEX-" for "6-amino-1-hexanoyl-", "FAM-" for "5, or 6-fluorescein-carbonyl-" (isomeric mixture), and "—NH$_2$" for non-substituted "-amino" group.

Figure 6:
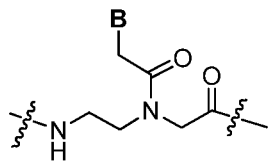
FIG. 6. Chemical structures for the PNA monomers abbreviated as A (adenine), G (guanine), T (thymine), C (cytosine), C(pOq), A(p), A(pOq), G(p), and G(pOq).
Figure 6:
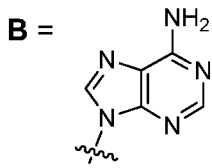
Figure 6:
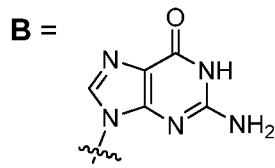
Figure 6:
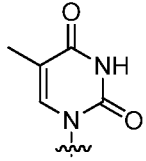
Figure 6:
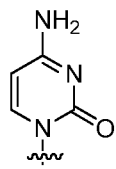
Figure 6:
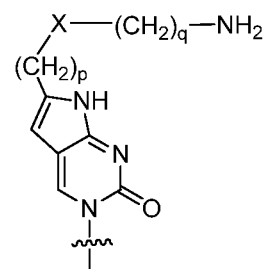
Figure 6:
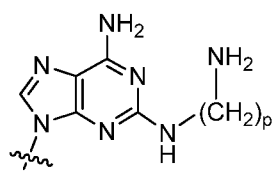
Figure 6:
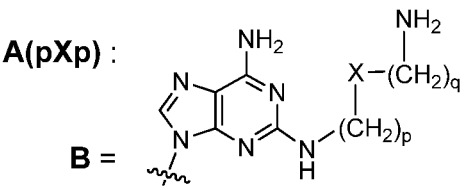
Figure 6:
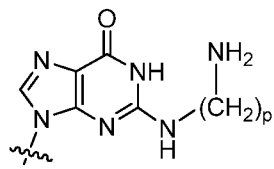
Figure 6:
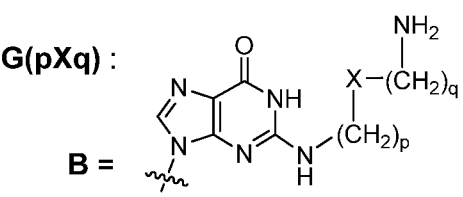

FIG. 6 collectively provides the chemical structures for the PNA monomers abbreviated as A, G, T, C, C(pOq), A(p), A(pOq), G(p), and G(pOq). As discussed in the prior art [PCT/KR2009/001256], C(pOq) is regarded as a modified PNA monomer corresponding to "cytosine" due to its preferred hybridization to "guanine". A(p) and A(pOq) are taken as modified PNA monomers acting as "adenine" for their tight affinity for "thymine". Likewise G(p) and G(pOq) are considered to be modified PNA monomers equivalent to "guanine" owing to their complementary base pairing with "cytosine".

Figure 7:
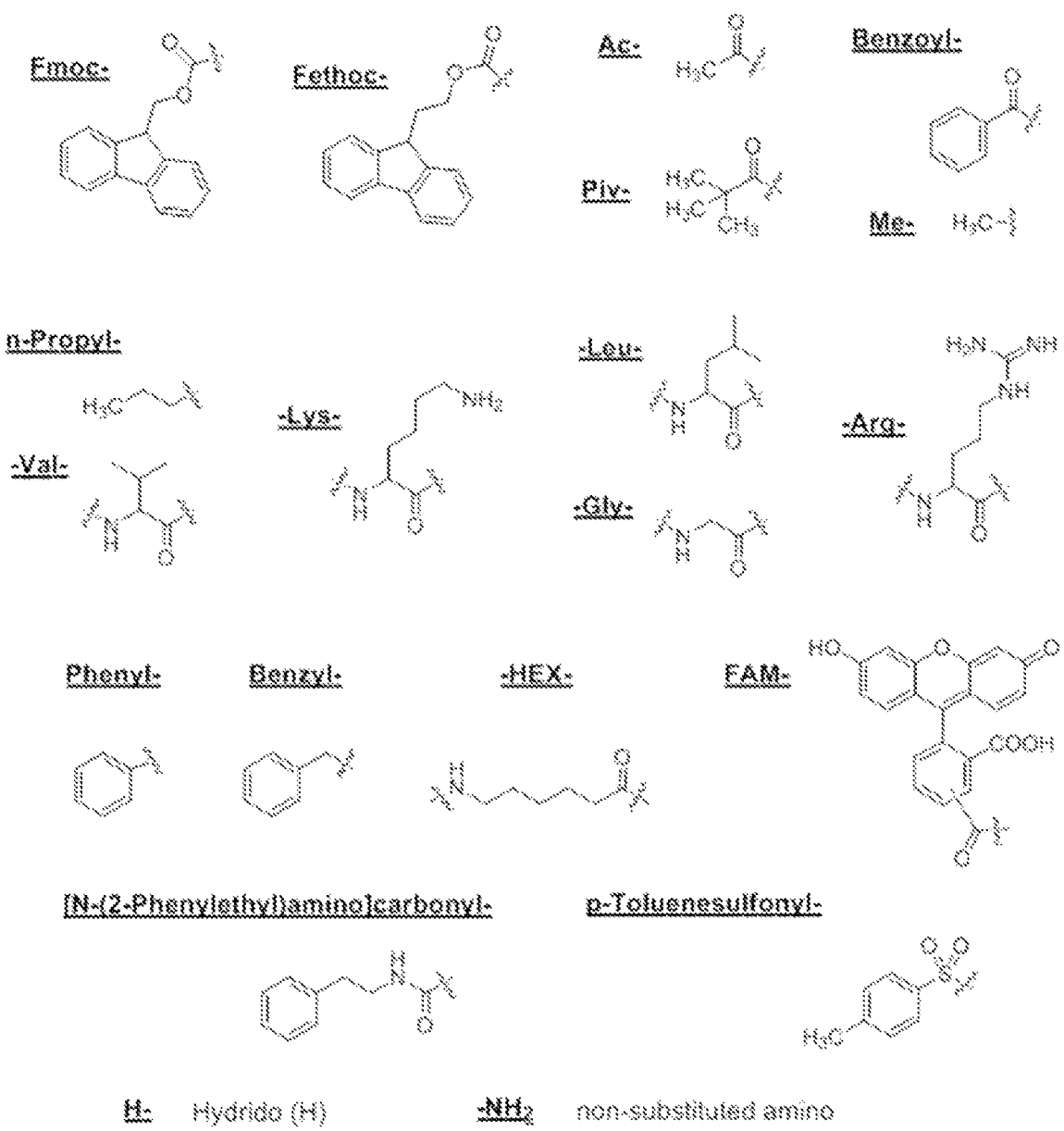
FIG. 7. Chemical structures for the abbreviations used to describe substituents for the N-terminal or C-terminal in the compound of Formula I.

FIG. 7 unequivocally provides the chemical structures for a variety of abbreviations for substituents used to introduce diversities in the N-terminus or C-terminus of the PNA derivative of Formula I.

Figure 8:
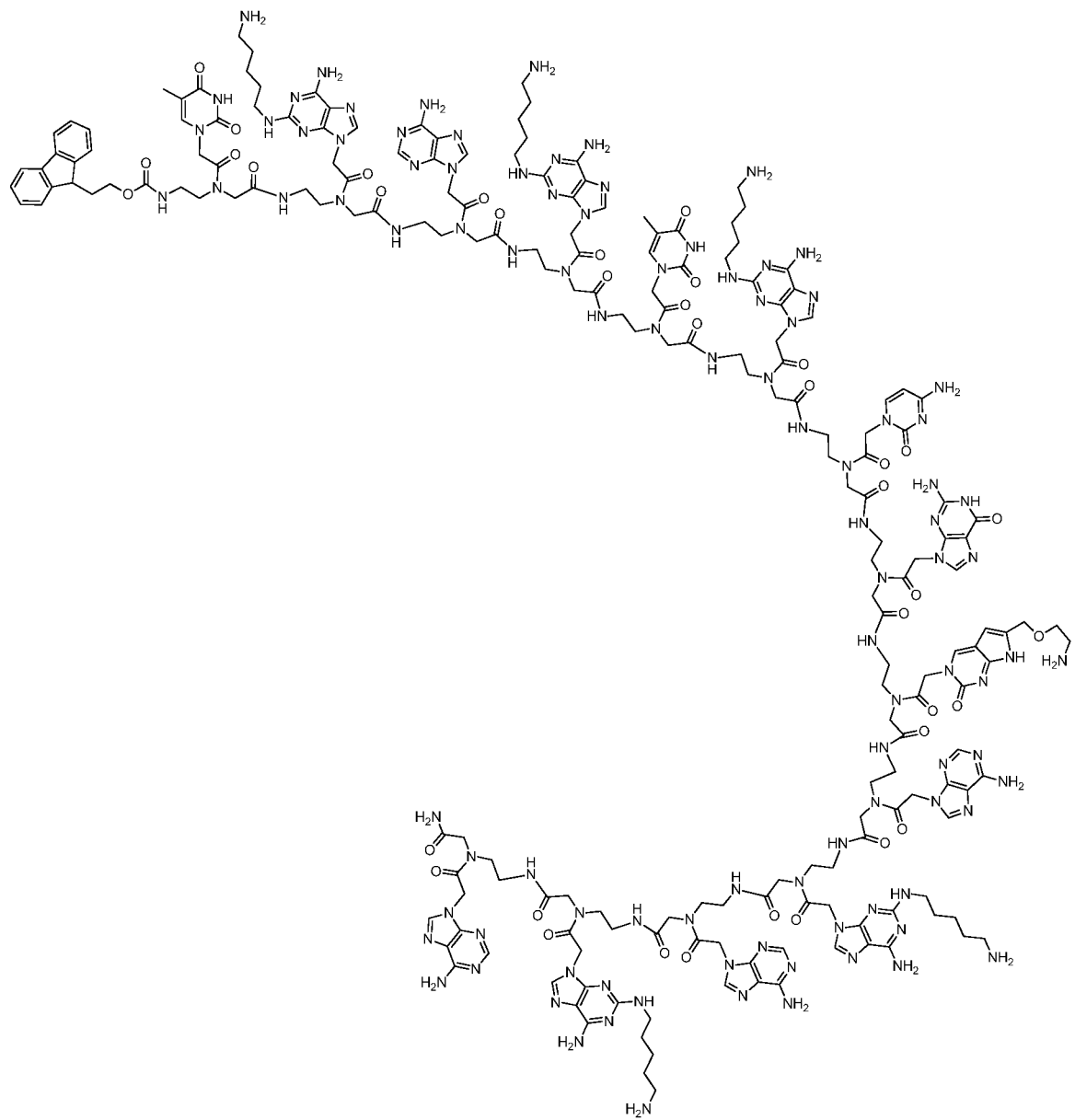
FIG. 8. Chemical structure for the 14-mer PNA derivative expressed as "(N→C) Fethoc-TA(5)A-A(5)TA(5)-CGC(1O2)-AA(5)A-A(5)A-NH₂"
Figure 9:
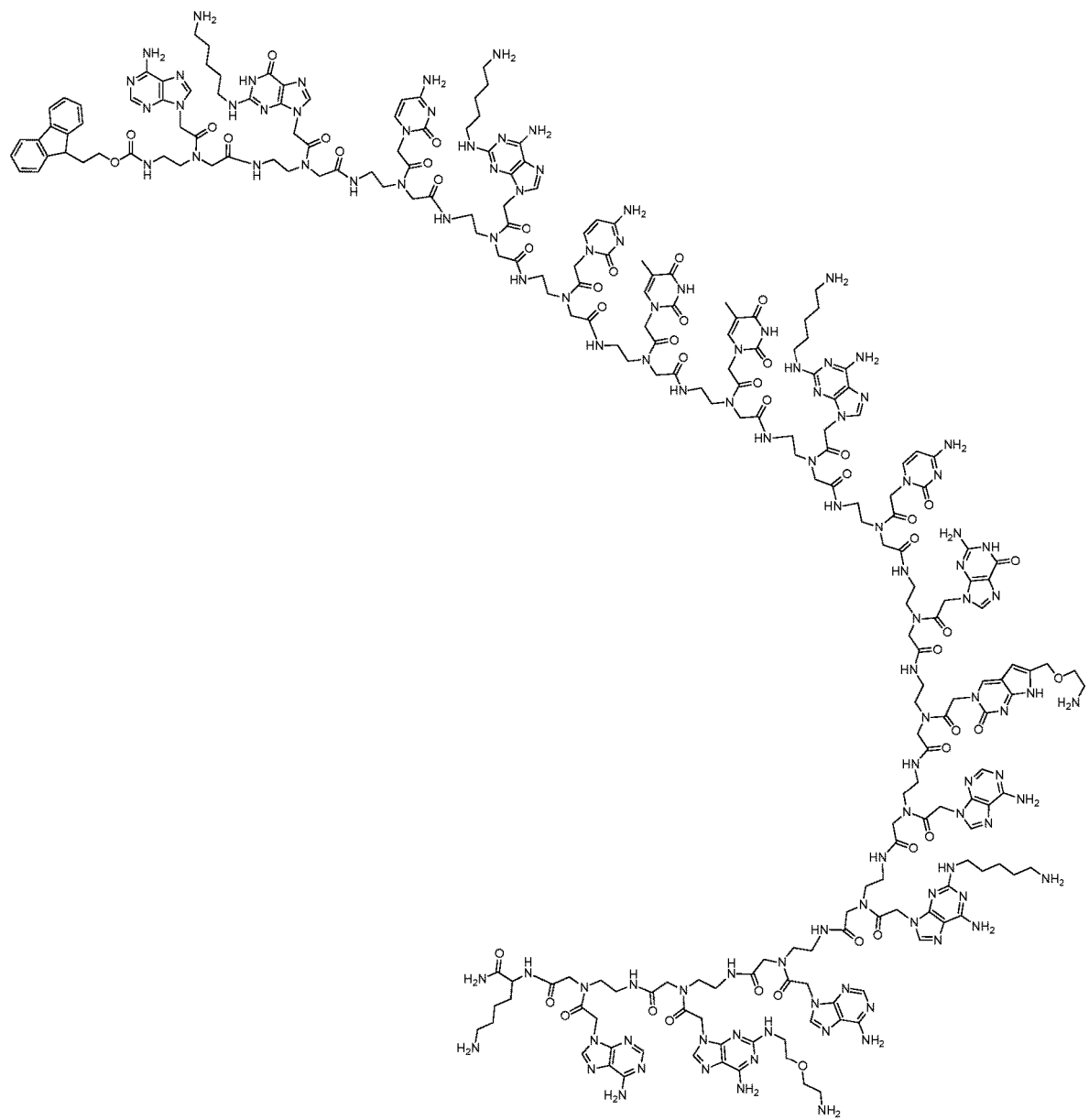
FIG. 9. Chemical structure for the 16-mer PNA derivative abbreviated as "(N→C) Fethoc-AG(5)C-A(5)CT-TA(5)C-GC(1O2)A-A(5)AA(2O2)-A-Lys-NH₂".

In order to illustrate the abbreviations for PNA derivatives, the chemical structure for a 14-mer PNA derivative denoted as "(N→C) Fethoc-TA(5)A-A(5)TA(5)-CGC(1O2)-AA(5)A-A(5)A-NH$_2$" is provided in FIG. 8. As another illustration, the chemical structure for a 16-mer PNA derivative abbreviated as "(N→C) Fethoc-AG(5)C-A(5)CT-TA(5)C-GC(1O2)A-A(5)AA(2O2)-A-Lys-NH$_2$" is provided in FIG. 9.

A 14-mer PNA sequence of "(N→C) Fethoc-AA(3)G-TG(2O2)T-A(5)CC(1O2)-TA(5)A-A(5)C-NH$_2$" is equivalent to the DNA sequence of "(5'→3') AAG-TGT-ACC-TAA-AC (SEQ ID NO: 4)", which has a 14-mer complementary overlap with a 20-mer pre-mRNA sequence as marked "bold" and "underlined" in

[(5' → 3') uuguguuuag | GUACACUUUU (SEQ ID NO: 5)]

spanning the junction of intron 3 and exon 4 within the human SCN9A pre-mRNA.

A 18-mer PNA sequence of (N→C) Fethoc-AA(5)G-TG(5)T-A(5)CC(1O2)-TA(5)A-A(3)CA-C(1O5)AA-NH$_2$" is equivalent to the DNA sequence of "(5'→3') AAG-TGT-ACC-TAA-ACA-CAA (SEQ ID NO: 6)", which has a 18-mer complementary overlap with the 20-mer SCN9A pre-mRNA sequence as marked "bold" and "underlined" in

[(5' → 3') uuguauuuag | GUACACUUUU (SEQ ID NO: 5)]

A 18-mer PNA sequence of "(N→C) Fethoc-AA(5)G-TCT-A(5)CC(1O2)-TA(5)A-A(3)CA(3)-CTA-NH$_2$" is equivalent to the DNA sequence of "(5'→3') AAG-TCT-ACC-TAA-ACA-CTA (SEQ ID NO: 7)", which has a 16-mer complementary overlap with the 20-mer SCN9A pre-mRNA sequence as marked "bold" and "underlined" in

[(5'→3') u"u"guguuuag|GUA"C"ACUUUU (SEQ ID NO: 5)]. Thus the 18-mer PNA has two single mismatches with the 3' splice site of exon 4 in the human SCN9A pre-mRNA. The two single mismatches are found in intron 3 and in exon 4 as marked with quote sign (" ").

A 14-mer PNA sequence of "(N→C) Fethoc-AA(5)G-TG (5)T-A(5)CC(1O2)-TA(5)A-A(5)G-NH$_2$" is equivalent to the DNA sequence of "(5'→3') AAG-TGT-ACC-TAA-AG (SEQ ID NO: 8)", which has a 13-mer complementary overlap with the 20-mer SCN9A pre-mRNA sequence as marked "bold" and "underlined" in

[(5' → 3') uugu"g"uuuag | GUACACUUUU (SEQ ID NO: 5)]

Thus the 14-mer PNA has a single mismatch with the 3' splice site of exon 4 in the human SCN9A pre-mRNA. The single mismatch is found in intron 3 as marked with quote sign (" ").

DETAILED DESCRIPTION OF INVENTION

General Procedures for Preparation of PNA Oligomers

Figure 10:
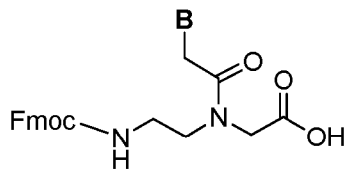
FIG. 10. Chemical structures of Fmoc-PNA monomers used to synthesize the PNA derivatives of this invention.
Figure 10:
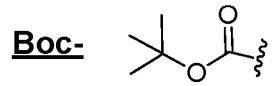
Figure 10:
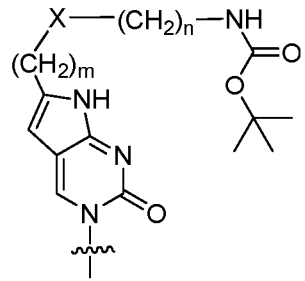
Figure 10:
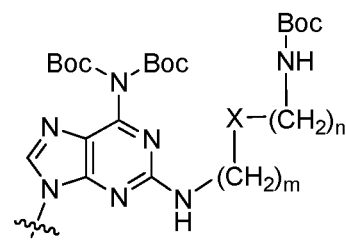
Figure 10:
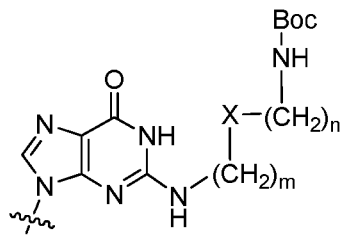

PNA oligomers were synthesized by solid phase peptide synthesis (SPPS) based on Fmoc-chemistry according to the method disclosed in the prior art [U.S. Pat. No. 6,133,444; WO 96/40685] with minor modifications if needed. The solid support employed in this study was H-Rink Amide-ChemMatrix purchased from PCAS BioMatrix Inc. (Quebec, Canada). Fmoc-PNA monomers with a modified nucleobase were synthesized as described in the prior art [PCT/KR 2009/001256] or with minor modifications. Such Fmoc-PNA monomers with a modified nucleobase and Fmoc-PNA monomers with a natural nucleobase were used to synthesize the PNA derivatives of the present invention. The Fmoc-PNA monomers with a modified nucleobase are provided in FIG. 10. To a skilled person in the field, however, there are lots of minor variations obviously possible for the protecting groups on such PNA monomers. Thus the Fmoc-PNA monomers in FIG. 10 should be taken as examples, and therefore should not be taken to limit the scope of the present invention. PNA oligomers were purified by C$_{18}$-reverse phase HPLC (water/acetonitrile or water/methanol with 0.1% TFA) and characterized by mass spectrometry including ESI/TOF/MS.

Figure 11:
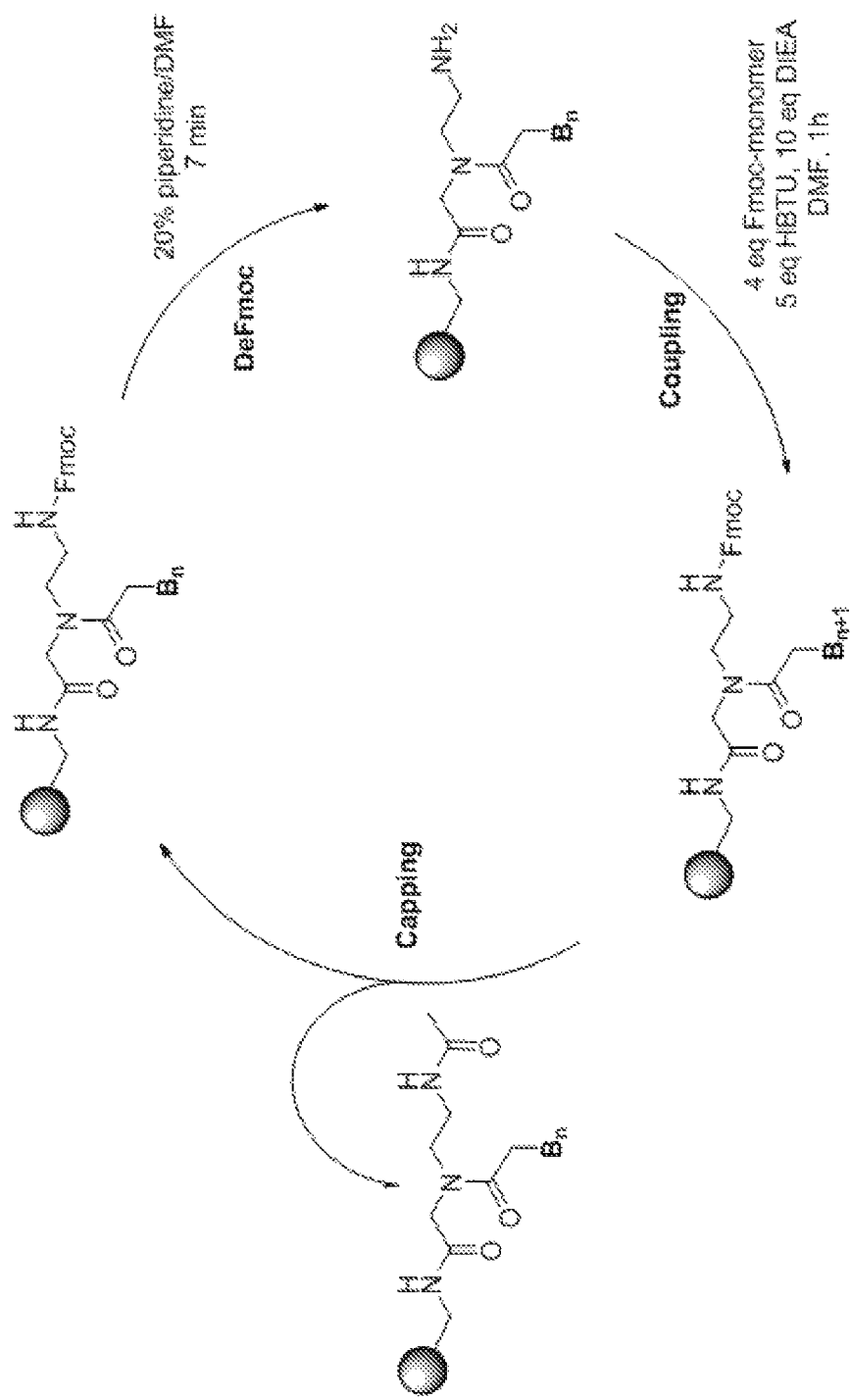
FIG. 11. Schematic illustration of a typical monomer elongation cycle adopted in SPPS of this invention.

FIG. 11 schematically illustrates a typical monomer elongation cycle adopted in the SPPS of this study, and the synthetic details are provided as below. To a skilled person in the field, however, there are lots of minor variations obviously possible in effectively running such SPPS reactions on an automatic peptide synthesizer or manual peptide synthesizer. Each reaction step is briefly provided as follows.

[Activation of H-Rink-ChemMatrix Resin] 0.01 mmol (ca 20 mg resin) of the ChemMatrix resin in 1.5 mL 20% piperidine/DMF was vortexed in a libra tube for 20 min, and the DeFmoc solution was filtered off. The resin was washed for 30 sec each in series with 1.5 mL methylene chloride (MC), 1.5 mL dimethylformamide (DMF), 1.5 mL MC, 1.5 mL DMF, and 1.5 mL MC. The resulting free amines on the solid support were subjected to coupling either with an Fmoc-PNA monomer or with an Fmoc-protected amino acid derivative.

[DeFmoc] The resin was vortexed in 1.5 mL 20% piperidine/DMF for 7 min, and the DeFmoc solution was filtered off. The resin was washed for 30 sec each in series with 1.5 mL MC, 1.5 mL DMF, 1.5 mL MC, 1.5 mL DMF, and 1.5 mL MC. The resulting free amines on the solid support were immediately subjected to coupling with an Fmoc-PNA monomer.

[Coupling with Fmoc-PNA Monomer] The free amines on the solid support were coupled with an Fmoc-PNA monomer as follows. 0.04 mmol of an Fmoc-PNA monomer, 0.05 mmol HBTU [2-(1H-benzotriazol-1-yl)-1,1,3,3-tetramethyluronium hexafluorophosphate], and 10 mmol DIEA (N,N-diisopropylethylamine) were incubated for 2 min in 1 mL anhydrous DMF, and added to the resin with free amines. The resin solution was vortexed for 1 hour and the reaction medium was filtered off. Then the resin was washed for 30 sec each in series with 1.5 mL MC, 1.5 mL DMF, and 1.5 mL MC.

[Capping] Following the coupling reaction, the unreacted free amines were capped by shaking for 5 min in 1.5 mL capping solution (5% acetic anhydride and 6% 2,6-leutidine in DMF). Then the capping solution was filtered off and washed for 30 sec each in series with 1.5 mL MC, 1.5 mL DMF, and 1.5 mL MC.

[Introduction of "Fethoc-" Radical in N-Terminus] "Fethoc-" radical was introduced to the N-terminus by reacting the free amines on the resin with "Fethoc-OSu" under usual basic coupling conditions. The chemical structure of "Fethoc-OSu" [CAS No. 179337-69-0, C$_{20}$H$_{17}$NO$_5$, MW 351.36] is provided as follows.

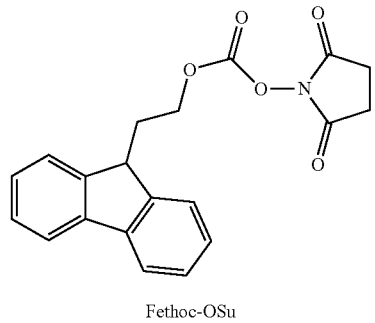 [SMILES: O=C(OCCC1c2ccccc2-c2ccccc21)ON1C(=O)CCC1=O]

Fethoc-OSu

[Cleavage from Resin] PNA oligomers bound to the resin were cleaved from the resin by shaking for 3 hours in 1.5 mL cleavage solution (2.5% tri-isopropylsilane and 2.5% water in trifluoroacetic acid). The resin was filtered off and the filtrate was concentrated under reduced pressure. The resulting residue was triturated with diethylether and the resulting precipitate was collected by filtration for purification by reverse phase HPLC.

Figure 12A:
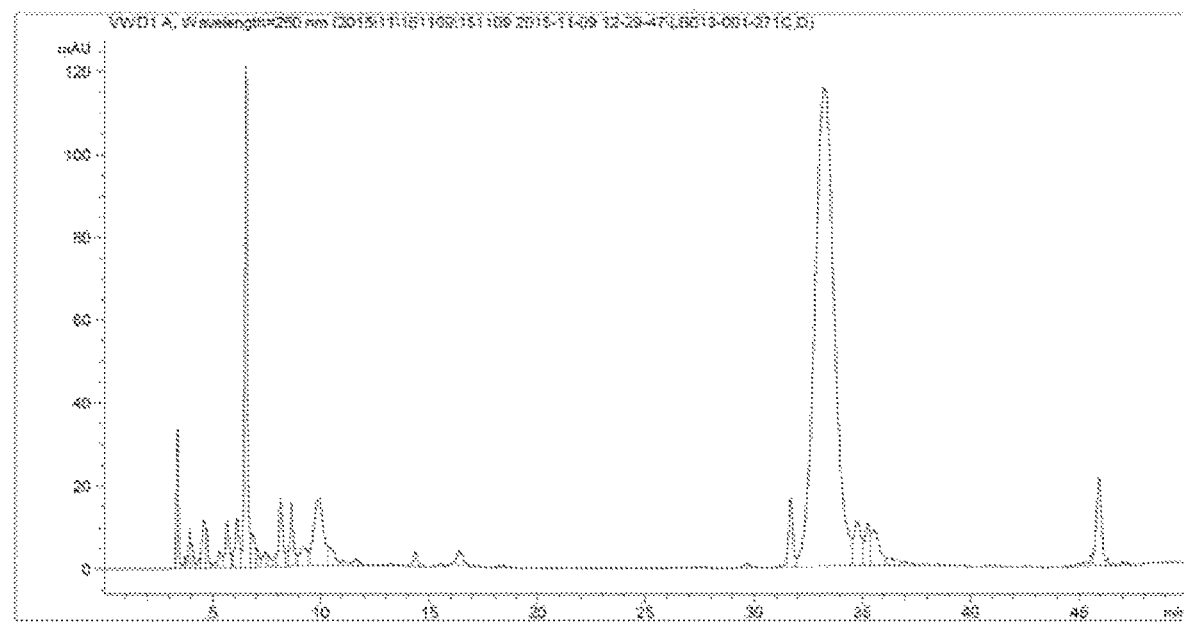
FIG. 12A. $C_{18}$-reverse phase HPLC chromatogram for "ASO 2" before HPLC purification.
Figure 12B:
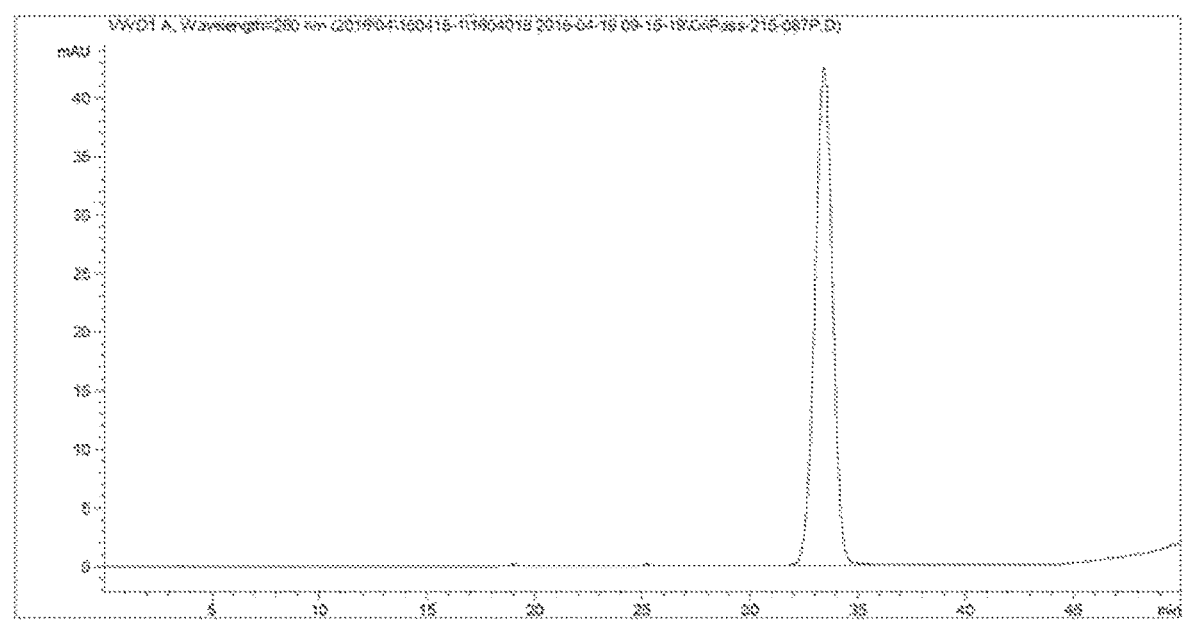
FIG. 12B. $C_{18}$-reverse phase HPLC chromatogram for "ASO 2" after HPLC purification.

[HPLC Analysis and Purification] Following a cleavage from resin, the crude product of each PNA derivative was purified by C$_{18}$-reverse phase HPLC eluting water/acetonitrile or water/methanol (gradient method) containing 0.1% TFA. FIGS. 12A and 12B are exemplary HPLC chromatograms for "ASO 2" before and after HPLC purification, respectively. The oligomer sequence of "ASO 2" is as provided in Table 1.

Synthetic Examples for PNA Derivative of Formula I

In order to complementarily target the 3' splice site spanning the junction of intron 3 and exon 4 within the human SCN9A pre-mRNA, PNA derivatives of this invention were prepared according to the synthetic procedures provided above or with minor modifications. Provision of such PNA derivatives targeting the human SCN9A premRNA is to exemplify the PNA derivatives of Formula I, and should not be interpreted to limit the scope of the present invention.

Table 1 provides PNA derivatives complementarily targeting the 3' splice site of "exon 4" in the human SCN9A pre-mRNA along with structural characterization data by mass spectrometry. Provision of the SCN9A ASOs in Table 1 is to exemplify the PNA derivatives of Formula I, and should not be interpreted to limit the scope of the present invention.

TABLE 1

PNA derivatives complementarily targeting the 3; splice site spanning the junction of intron 3 and exon 4 within the human SCN9A pre-mRNA along with structural characterization data by mass spectrometry.

| PNA Example | PNA Sequence (N → C) | Exact Mass, m/z theor.[a] | obs.[b] |
|---|---|---|---|
| ASO 1 | Fethoc-TA(5)A-A(5)AG(6)-TG(6)T-A(5)CC(102)-TA(5)A-A(5)-NH₂ | 5398.60 | 5398.58 |
| ASO 2 | Fethoc-AA(5)G-TG(6)T-A(5)CC(102)-TAA(5)-A-NH₂ | 4282.97 | 4284.99 |
| ASO 3 | Fethoc-AA(5)G-TG(6)T-AC(102)C-TAA(5)-A-NH₂ | 4182.87 | 4182.89 |
| ASO 4 | Fethoc-A(5)AG-TG(6)T-A(5)CC(102)-TAA-A(5)-NH₂ | 4282.97 | 4283.00 |
| ASO 5 | Fethoc-AAG(6)-TG(6)T-A(5)CC(102)-TA(5)A-A-NH₂ | 4281.98 | 4282.05 |
| ASO 6 | Fethoc-AA(5)G-TG(5)T-A(5)CC(102)-TA(5)A-A(5)-NH₂ | 4369.06 | 4369.08 |
| ASO 7 | Fethoc-AA(5)G-TG(5)T-A(5)CC(102)-TA(5)A-A(5)C-NH₂ | 4620.16 | 4620.14 |
| ASO 8 | Fethoc-A(5)GT-G(5)TA(5)-CC(102)T-A(5)AA(5)-C-NH₂ | 4345.04 | 4345.08 |
| ASO 9 | Fethoc-AA(6)G-TG(5)T-A(6)CC(102)-TA(6)A-A(6)C-NH₂ | 4676.22 | 4676.25 |
| ASO 10 | Fethoc-AA(5)G-TG(5)T-A(5)CC(102)-TA(5)A-A(5)G-NH₂ | 4660.16 | 4660.15 |
| ASO 11 | Fethoc-AA(5)G-TG(5)T-A(5)CC(102)-TA(5)A-A(5)CA-NH₂ | 4895.27 | 4895.20 |
| ASO 12 | Fethoc-AA(5)G-TG(5)T-A(5)CC(102)-TA(5)A-A(5)GG-NH₂ | 4951.27 | 4951.26 |
| ASO 13 | Fethoc-AA(5)G-TG(5)T-ACC(102)-TA(5)A-A(5)CA(5)-C-NH₂ | 5146.37 | 5146.35 |
| ASO 14 | Benzoyl-AA(5)G-TG(5)T-A(5)CC(102)-TA(5)A-A(5)C-NH₂ | 4488.10 | 4488.06 |
| ASO 15 | Piv-AA(5)G-TG(5)T-A(5)CC(102)-TA(5)A-A(5)C-NH₂ | 4468.13 | 4468.04 |
| ASO 16 | Fethoc-AA(5)G-TA(5)T-A(5)CC(102)-TG(5)A-A(5)C-NH₂ | 4620.16 | 4620.14 |
| ASO 17 | p-Toluenesulfonyl-AA(5)G-TG(203)T-A(5)CC(102)-TA(5)A-A(5)C-Lys-NH₂ | 4682.17 | 4682.15 |
| ASO 18 | n-Hexanoyl-AA(5)G-TG(5)T-A(5)CC(102)-TA(8)A-A(5)C-NH₂ | 4524.19 | 4524.20 |
| ASO 19 | Fethoc-Lys-Leu-AA(5)G-TG(5)T-A(5)CC(102)-TA(202)A-A(5)C-Lys-NH₂ | 4991.41 | 4991.37 |
| ASO 20 | [N-(2-Phenylethyl)amino]carbonyl-AA(3)G-TG(5)T-A(5)CC(105)-TA(5)A-A(5)C-NH₂ | 4545.16 | 4545.15 |
| ASO 21 | H-AA(5)G-TG(202)T-A(5)CC(102)-TA(5)A-A(5)C-NH₂ | 4386.05 | 4386.03 |
| ASO 22 | n-Propyl-AA(5)G-TG(5)T-A(5)CC(103)-TA(5)A-A(5)C-NH₂ | 4440.14 | 4440.06 |
| ASO 23 | N,N-Phenyl-Me-AA(5)G-TG(5)T-A(5)CC(102)-TA(5)A-A(4)C-NH₂ | 4460.10 | 4460.09 |

TABLE 1-continued

PNA derivatives complementarily targeting the 3; splice site spanning the junction of intron 3 and exon 4 within the human SCN9A pre-mRNA along with structural characterization data by mass spectrometry.

| PNA Example | PNA Sequence (N → C) | Exact Mass, m/z theor.[a] | obs.[b] |
|---|---|---|---|
| ASO 24 | Benzoyl-AA(5)G-TG(3)T-A(5)CC(202)-TA(5)A-A(5)C-NH$_2$ | 4474.08 | 4474.11 |
| ASO 25 | p-Toluenesulfonyl-TG(203)T-A(5)CC(102)-TA(5)A-A(3)CA-C-Lys-NH$_2$ | 4238.92 | 4238.95 |
| ASO 26 | Fethoc-AA(5)G-TG(5)T-A(5)AC(102)-TA(5)T-A(5)C-NH$_2$ | 4635.16 | 4635.14 |

[a]theoretical exact mass, [b]observed exact mass

Figure 13:
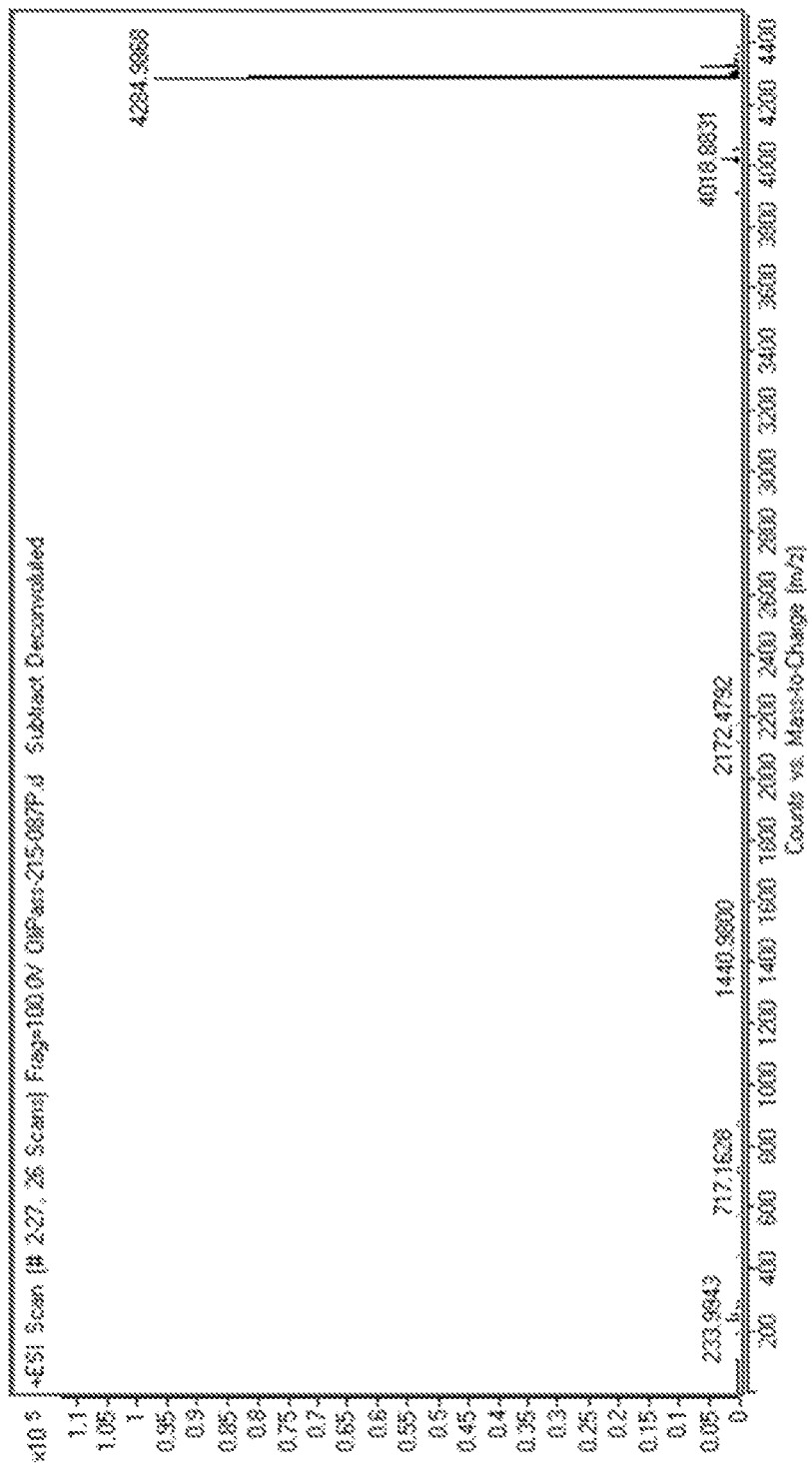
FIG. 13. ES-TOF mass spectral data obtained with "ASO 2" after HPLC purification.

FIG. 12A is a HPLC chromatogram obtained with a crude product of "ASO 2". The crude product was purified by $C_{18}$-reverse phase (RP) preparatory HPLC. FIG. 12B is a HPLC chromatogram for a purified product of "ASO 2". The purity of "ASO 2" improved markedly by the preparatory HPLC purification. FIG. 13 provides an ESI-TOF mass spectrum obtained with the purified product of "ASO 2". Provision of the analysis data for "ASO 2" is to illustrate how the PNA derivatives of Formula I were purified and identified in the present invention, and should not be interpreted to limit the scope of this invention.

Binding Affinity of PNA Derivatives for Complementary DNA

The PNA derivatives in Table 1 were evaluated for their binding affinity for 10-mer DNAs complementarily targeting either the N-terminal or C-terminal of PNA. The binding affinity was assessed by $T_m$ value for the duplex between PNA and 10-mer complementary DNA. The duplex between PNA derivatives in Table 1 and fully complementary DNAs show $T_m$ values too high to be reliably determined in aqueous buffer solution, since the buffer solution tended to boil during the $T_m$ measurement.

$T_m$ values were determined on a UV/V is spectrometer as follows. A mixed solution of 4 μM PNA oligomer and 4 μM complementary 10-mer DNA in 4 mL aqueous buffer (pH 7.16, 10 mM sodium phosphate, 100 mM NaCl) in 15 mL polypropylene falcon tube was incubated at 90° C. for a minute and slowly cooled down to ambient temperature. Then the solution was transferred into a 3 mL quartz UV cuvette equipped with an air-tight cap, and subjected to a $T_m$ measurement on a UV/Visible spectrophotometer at 260 nm as described in the prior art [PCT/KR2009/001256] or with minor modifications. The 10-mer complementary DNAs for $T_m$ measurement were purchased from Bioneer (www.bioneer.com, Dajeon, South Korea) and used without further purification.

The observed $T_m$ values of the PNA derivatives of Formula I were very high for a complementary binding to 10-mer DNA, and are provided in Table 2 as uncorrected. For example, "ASO 7" showed a $T_m$ value of 77.0° C. for the duplex with the 10-mer complementary DNA [i.e. (5'→3') AGG-TAC-ACT-T (SEQ ID NO: 9)] targeting the N-terminal 10-mer in the PNA as marked "bold" and "underlined" in

[(N → C) Fethoc-AA(5)G-TG(5)T-A(5)CC(102)-TA(5)A-A(5)C-NH$_2$].

In the meantime, "ASO 7" showed a $T_m$ of 69.0° C. for the duplex with the 10-mer complementary DNA [i.e. (5'→3') GTT-TAG-GTA-C (SEQ ID NO: 10)] targeting the C-terminal 10-mer in the PNA as marked "bold" and "underlined" in

[(N → C) Fethoc-AA(5)G-TG(5)T-A(5)CC(102)-TA(5)A-A(5)C-NH$_2$].

TABLE 2

$T_m$ values between PNAs in Table 1 and 10-mer complementary DNA targeting either the N-terminal or the C-terminal of PNA.

| | $T_m$ Value, ° C. | |
|---|---|---|
| PNA | 10-mer DNA against N-Terminal | 10-mer DNA against C-Terminal |
| ASO 2 | 74.0 | 65.0 |
| ASO 4 | 77.0 | 66.0 |
| ASO 5 | 78.0 | 66.0 |
| ASO 6 | 75.0 | 72.0 |
| ASO 7 | 77.0 | 69.0 |
| ASO 8 | 78.1 | 70.0 |
| ASO 10 | 79.0 | 74.0 |

Examples for Biological Activities of PNA Derivatives of Formula I

PNA derivatives of Formula I were evaluated for in vitro and in vivo biological activities. The biological examples provided below are to illustrate the antisense activity of PNA derivatives of Formula I in cells as well as in animals, and therefore should not be interpreted to limit the scope of the current invention to the compounds listed in Table 1.

Example 1. Exon Skipping Induced by "ASO 7" in PC3 Cells (A)

"ASO 7" specified in Table 1 is a 14-mer ASO complementarily binding to a 14-mer sequence of the 3' splice site spanning the junction of intron 3 and exon 4 within the human SCN9A pre-mRNA. The 14-mer target sequence within the 3' splice site is as marked "bold" and "underlined" in

[(5'→ 3') uuguguuuag | GUACACUUuu (SEQ ID NO: 5)].

"ASO 7" possesses a 6-mer complementary overlap with intron 3, and an 8-mer complementary overlap with exon 4.

Since PC3 cells (Cat. Number CRL1435, ATCC) are known to abundantly express the human SCN9A mRNA [*Br. J. Pharmacol.* vol 156, 420-431 (2009)], "ASO 7" was evaluated for its ability to induce the skipping of exon 4 in PC3 cells as follows.

[Cell Culture & ASO Treatment] PC3 cells grown in 60 mm culture dish containing 5 mL F-12K medium were treated with "ASO 7" at 0 (negative control), 1, 10 or 100 zM.

[RNA Extraction & cDNA Synthesis by One-step PCR] Following an incubation with "ASO 7" for 5 hours, total RNA was extracted using "Universal RNA Extraction Kit" (Cat. Number 9767, Takara) according to the manufacturer's instructions. 200 ng of RNA template was subjected to a 25 µL reverse transcription reaction using Super Script® One-Step RT-PCR kit with Platinum® Taq polymerase (Cat. No. 10928-042, Invitrogen) against a set of exon-specific primers of [exon 2_forward: (5'→3') CTTTCTCCTTTCAGTCCTCT (SEQ ID NO: 11); and exon 9_reverse: (5'→3') CGTCTGTTGGTAAAGGTTTT (SEQ ID NO: 12)] according to the following cycle conditions: 50° C. for 30 min and 94° C. for 2 min, which was followed by 15 cycles of 30 sec at 94° C., 30 sec at 55° C., and 2 min at 72° C.

[Nested PCR Amplification] 1 µL of cDNA was then subjected to a 20 µL nested PCR reaction (Cat. No. K2612, Bioneer) against a set of exon-specific primers of [exon 2n_forward: (5'→3') CCACCGGACTGGACCAAAAA (SEQ ID NO: 13); and exon 9n_reverse: (5'→3') GCTAAGAAGGC-CCAGCTGAA (SEQ ID NO: 14)] according to the following cycle conditions: 95° C. for 2 min followed by 34 cycles of 30 sec at 95° C., 30 sec at 55° C., and 1 min at 72° C.

[Identification of Exon Skipping Products] The PCR products were subjected to electrophoretic separation on a 2% agarose gel. The bands of target size were collected and analyzed by Sanger Sequencing.

Figure 14A:
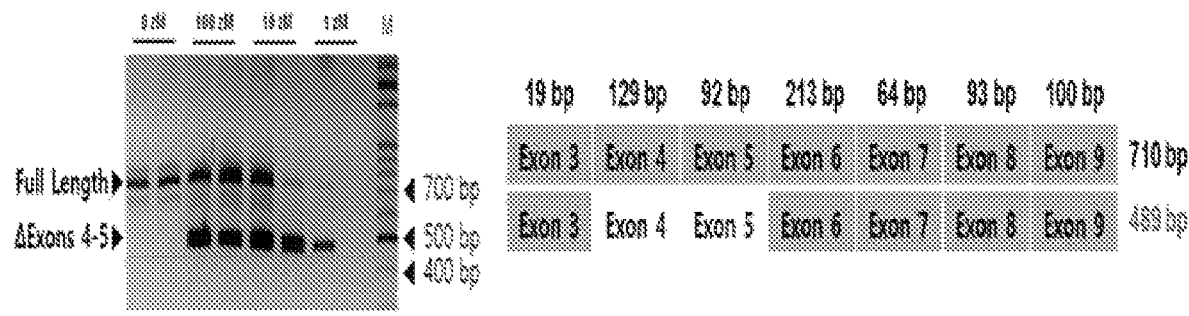
FIG. 14A. Electrophoresis data of SCN9A nested RT-PCR products in PC3 cells treated with "ASO 7" for 5 hours at 0 (negative control), 10, or 100 zM.
Figure 14B:
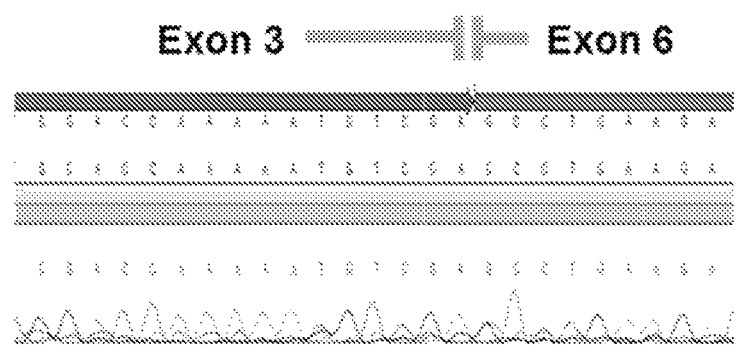
FIG. 14B. Sanger sequencing data for the PCR product band assigned to the skipping of exons 4-5.

FIG. 14A provides the electrophoresis data of the nested PCR products, in which the cells treated with "ASO 7" yielded a strong PCR band assignable to the skipping of exons 4-5. However, the PCR band for the full-length SCN9A mRNA tended to be stronger in the samples treated with 10 or 100 zM ASO than in the negative control sample. The strange dose response pattern in the nested PCR could be due to a transcription upregulation by the "exon intron circular RNA (EIciRNA)" accumulated during the exon skipping with "ASO 7". [*Nature Struc. Mol. Biol.* vol 22(3), 256-264 (2015)] The exon skipping PCR product was confirmed by Sanger sequencing to be the skipping of exons 4-5 as shown in FIG. 14B.

Example 2. Exon Skipping Induced by "ASO 7" in PC3 Cells (B)

"ASO 7" was evaluated for its ability to induce the skipping of "exon 4" in PC3 cells as in "Example 1", unless noted otherwise. In this experiment, PC3 cells were treated with "ASO 7" at 0 (negative control), 1, 10, 100 and 1,000 aM for 24 hours. The nested PCR reaction was carried out against a set of primers of [exon 3/6_forward: (5'→3') GGACCAAAAATGTCGAGCCT (SEQ ID NO: 15); and exon 9_reverse: (5'→3') GCTAAGAAGGCCCAGCTGAA (SEQ ID NO: 14)] designed to amplify the product possessing the junction sequence of exon 3 and exon 6.

The primer sequence of "exon 3/6_forward" recognizes "the junction of exon 3 and exon 6" more selectively than "the junction of exon 3 and exon 4" found in the full length SCN9A mRNA. The primer sequence was designed to detect the SCN9A splice variant lacking exons 4-5 more sensitively than the full length SCN9A mRNA. Such an exon skipping primer would be useful to detect mRNA splice variants with poor metabolic stability, since full-length mRNAs tend to show good metabolic stability gained through the evolution over billions years.

Figure 14C:
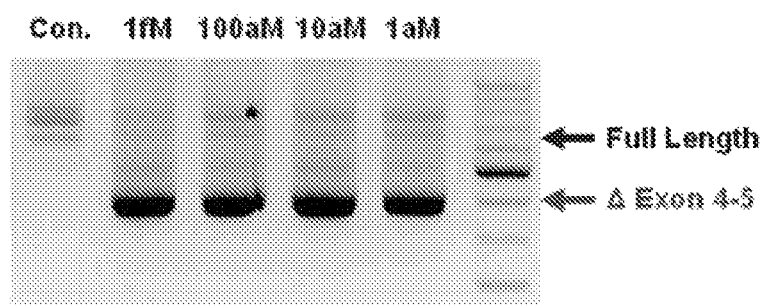
FIG. 14C. Electrophoresis data of SCN9A nested RT-PCR products in PC3 cells treated with "ASO 7" for 24 hours at 0 (negative control), 1, 10, 100 or 1,000 aM.

FIG. 14C provides the electrophoresis data of the nested PCR products, in which the cells treated with "ASO 7" yielded a strong PCR band assignable to the skipping of exons 4-5. The exon skipping PCR product was confirmed by Sanger sequencing to be the skipping of exons 4-5.

Example 3. qPCR for SCN9A mRNA in PC3 Cells Treated with "ASO 7" (A)

"ASO 7" was evaluated by SCN9A nested qPCR for its ability to induce changes in the human SCN9A mRNA level in PC3 cells as described below.

[ASO Treatment] PC3 cells were treated with "ASO 7" at 0 (negative control), 0.1, 1 or 10 aM. (2 culture dishes per each ASO concentration) [RNA Extraction & cDNA Synthesis by One-step PCR] Following an incubation with "ASO 7" for 24 hours, total RNA was extracted and subjected to one-step PCR amplification as described in "Example 1".

[Nested qPCR Amplification] The cDNA solutions were diluted by 100 times, and 1 µL of each diluted PCR product was subjected to a 20 µL Real-Time PCR reaction against a set of exon specific primers of [exon 3_forward: (5'→3') TGACCATGAATAACCCAC (SEQ ID NO: 16); and exon 4 reverse: (5'→3') GCAAGGATTTTTACAAGT (SEQ ID NO: 17)] according to the following cycle conditions: 95° C. for 30 sec followed by 40 cycles 5 sec at 95° C., and 30 sec at 60° C. The qPCR reaction was followed with a TaqMan probe of [(5'→3') 5,6-FAM-GGACCAAAA-Zen-ATGTCGAGTACAC-3IABkFQ] ("ATGTCGAGTACAC" disclosed as SEQ ID NO: 18) targeting the junction of exon 3 and exon 4 within the full-length SCN9A mRNA.

Figure 15A:
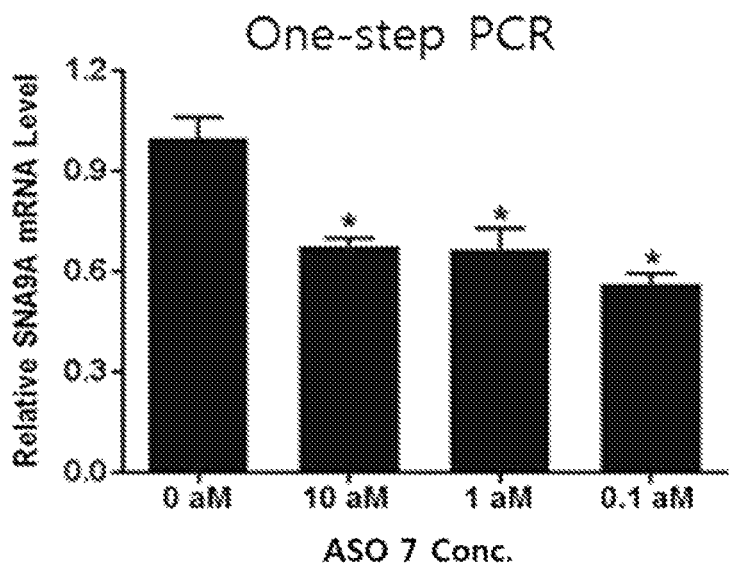
FIG. 15A. qPCR data for the full-length SCN9A mRNA in PC3 cells treated with "ASO 7" at 0 (negative control), 0.1, 1 or 10 aM for 24 hours. cDNA was synthesized by one-step PCR. (error bar by standard error; and * for p<0.05)

FIG. 15A summarizes the observed qPCR data, in which the full-length SCN9A mRNA level significantly decreased (student's t-test) in the cells treated with "ASO 7" by ca 35~45%.

Example 4. qPCR for SCN9A mRNA in PC3 Cells Treated with "ASO 7" (B)

"ASO 7" was evaluated by SCN9A nested qPCR for its ability to induce changes in the human SCN9A mRNA level in PC3 cells as in "Example 3", unless noted otherwise. cDNA was synthesized using random hexamers, and subjected to SCN9A qPCR reaction against the TaqMan probe.

Figure 15B:
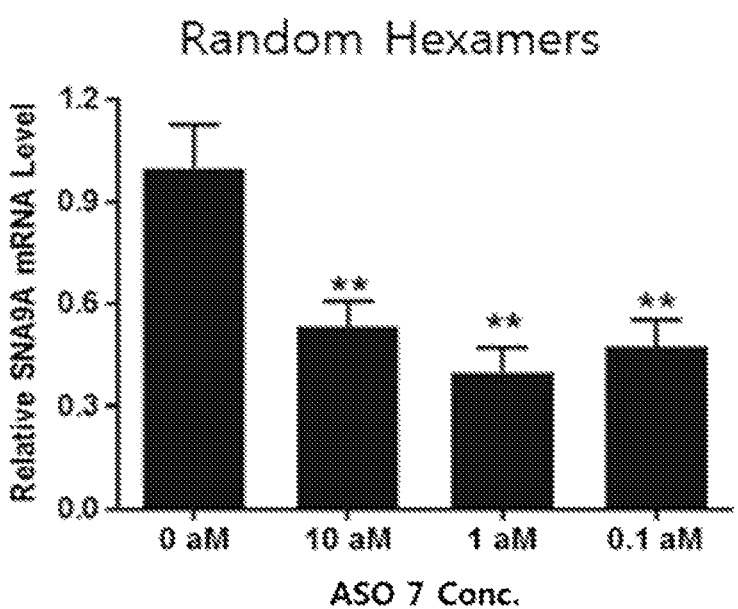
FIG. 15B. qPCR data for the full-length SCN9A mRNA in PC3 cells treated with "ASO 7" at 0 (negative control), 0.1, 1 or 10 aM for 24 hours. cDNA was synthesized using random hexamers. (error bar by standard error; and ** for p<0.05)

FIG. 15B provides the observed qPCR data, in which the full-length SCN9A mRNA level significantly decreased (student's t-test) in the cells treated with "ASO 7" by ca 50~60%.

Example 5. Induction of Spinal Neuropathy in Rats by L5/L6 Spinal Nerve Ligation Spinal nerve ligation (SNL) induces neuropathy in the dorsal root ganglia (DRG) and spinal cord, and has been widely used as a model for neuropathic pains. [*Pain* vol 50(3), 355-363 (1992)] Depending on how spinal nerve bundle(s) is ligated, however, there are several variations of SNL. The degree and duration of neuropathy in DRG appears to vary depending on how spinal nerve bundle(s) is ligated. [*Pain* vol 43(2), 205-218 (1990)] According to in-house experience, the dual ligation of the L5 and L6 spinal nerves (i.e., "L5/L6 ligation") induces neuropathy more severe and persisting longer than the single ligation of the L5 spinal nerve (i.e. "L5 ligation").

[SNL Surgery by L5/L6 Ligation] Male SD rats were anesthetized with zoletil/rompun. Then the L5 and L6 spinal nerve bundles (left side) were exposed and tightly ligated. Then the muscle and skin were closed and clipped according to due aseptic procedures.

[Induction of Neuropathic Pain] 6 to 7 days after the SNL operation, the paw of the ligated side was stimulated by von Frey scoring using an electronic von Frey anesthesiometer (Model Number 2390, IITC Inc. Life Science) as described below. Von Frey scoring was done on a daily basis until the grouping for pharmacologic evaluations.

[Electronic Von Frey Scoring] After stabilization for less than 30 minutes each animal in a plastic cage customized for von Frey scoring, the left hind paw of each animal was subjected to von Frey scoring 6 times with an interval of several minutes between scorings. The score from the first scoring was discarded since the animals were not stabilized during the first scoring. Of the five remaining scores, the highest and lowest scores were excluded. Then the average of the remaining three scores was taken as the von Frey score for the animal.

Example 6. Reversal of Allodynia by "ASO 7" in Rats with Spinal Neuropathy. (1)

"ASO 7" is a 14-mer SCN9A ASO partially complementary to the rat SCN9A pre-mRNA read out from the rat genomic DNA [NCBI Reference Sequence: NC_000002.12] with a single mismatch at the 3'-end of the target sequence. The target 13-mer sequence of "ASO 7" within the rat SCN9A pre-mRNA is specified "bold" and "underlined" as marked in the 20-mer SCN9A pre-mRNA sequence of

[(5'→ 3') uuuc"c"uuuag | GUACACUUuu (SEQ ID NO: 19)], wherein the single mismatch found in intron 3 was marked with quote sign (" ").

"ASO 7" was evaluated for its ability to reverse the allodynia in rats with spinal neuropathy induced by "L5/L6 ligation" as described below.

[SNL Surgery and Grouping] In Day –10, male SD rats (6 weeks old, Harlan Laboratories, Italy) were subjected to "L5/L6 ligation". Animals were stimulated by von Frey scoring from Day –4 on a daily basis. In Day 0, 30 animals were selected based on individual von Frey scores in Day 0, and assigned into 4 groups of the negative control group (i.e., no ASO treatment), and the three treatment groups of 1, 3 and 6 pmole/Kg "ASO 7". (6 or 9 animals per group)

[ASO Treatment and Von Frey Scoring] Rats subcutaneously received "ASO 7" at 0 (negative control), 1, 3 or 6 pmole/Kg in the afternoon in Days 0, 2, 4, 6, 8 and 10. Allodynia was scored by the electronic von Frey scoring method described in "Example 5" in the morning. The ASO was administered as "naked" oligonucleotide, i.e., as dissolved in PBS.

Figure 16A:
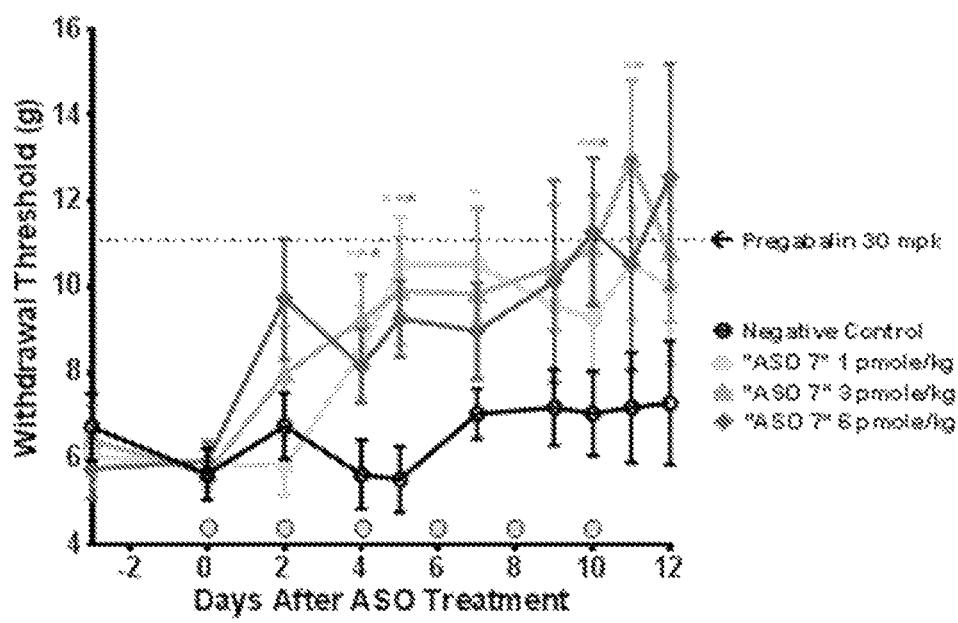
FIG. 16A. Reversal of the allodynia induced by L5/L6 ligation in SD rats subcutaneously administered with "ASO 7" at 0 (negative control), 1, 3 or 6 pmole/Kg, once per 2 days. The von Frey threshold for pregabalin 30 mpk was added by adopting the inhouse historical background. (* for p<0.05 by student's t-test)

[Reversal of Allodynia] FIG. 16A summarizes the observed outcomes of the von Frey scorings. The animals in the negative control group showed average von Frey scores (withdrawal threshold) stabilized between ca 6 and 7 g over the period of the 12 days post the grouping. "ASO 7" significantly reversed (student's t-test) the allodynia from Day 4 and afterwards. Even though the therapeutic activity was comparable in all the treatment groups, the 6 pmole/Kg group started showing the therapeutic activity from Day 2 post the first dosing.

Although there was no positive control comparator included in this specific evaluation, von Frey scores of 10 to 12 g were frequently observed according to in-house evaluations in rats (with "L5/L6 ligation") orally administered with pregabalin at 30 mg/Kg. Thus the efficacy of "ASO 7" at 1 to 6 pmole/Kg would be comparable to pregabalin 30 mg/Kg in this specific neuropathic pain model.

Example 7. Reversal of Allodynia by "ASO 2" in Rats with Spinal Neuropathy

"ASO 2" specified in Table 1 is a 13-mer ASO fully complementary to the 3' splice site spanning the junction of intron 3 and exon 4 in the human SCN9A pre-mRNA as marked "bold" and "underlined" in

[(5'→ 3') uuguguuuag | GUACACUUuu (SEQ ID NO: 5)].

"ASO 2" possesses a 5-mer overlap with intron 3, and an 8-mer overlap with exon 4. The target sequence of "ASO 2" is conserved in the rat SCN9A pre-mRNA.

"ASO 2" was evaluated for its ability to reverse the allodynia in rats with spinal neuropathy induced by "L5/L6 ligation" as described in "Example 6", unless noted otherwise.

[Grouping and ASO Treatment] Male SD rats (5 weeks old, Harlan Laboratories, Italy) were subjected to SNL operation in Day –16. In Day 0, 30 rats selected and assigned into 5 groups of the negative control group (i.e., no ASO treatment), and the four treatment groups of 20 pmole/Kg QD (i.e., daily once), 100 pmole/Kg QD, 500 pmole/Kg QD and 100 pmole/Kg Q2D (i.e., once per every two days) "ASO 2". (6 animals per group) The animals were subcutaneously administered with "ASO 2" during Days 0 to 13 according to the dosing schedules of QD and Q2D. The ASO was administered as "naked" oligonucleotide, i.e., as dissolved in PBS.

[Allodynia Scoring] Allodynia was scored during Days 0 to 14 according to the von Frey method described in "Example 5". In Day 7, the right paw (unligated side) was subjected to the von Frey scoring.

Figure 16B:
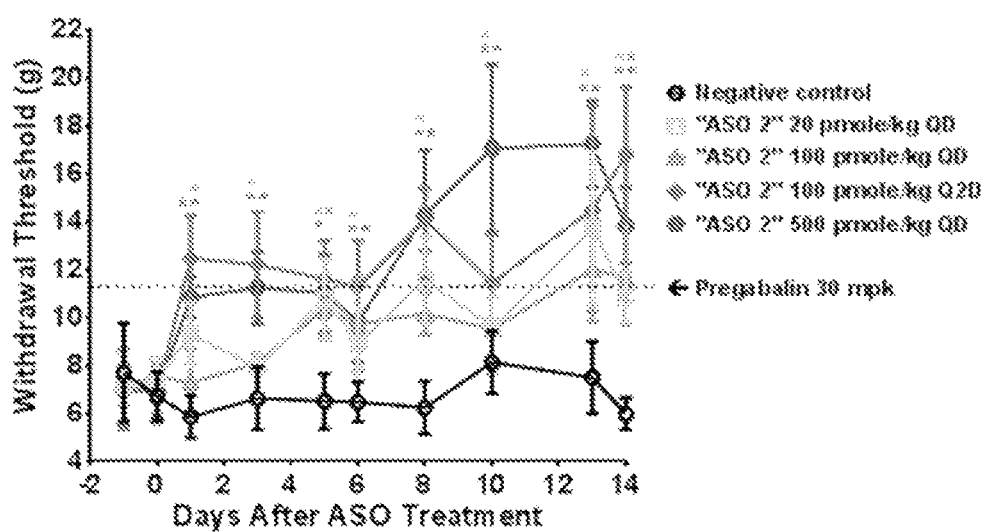
FIG. 16B. Reversal of the allodynia induced by SNL (L5/L6 ligation) in SD rats subcutaneously receiving "ASO 2" at 0 (negative control), 20 pmole/Kg QD, 100 pmole/Kg QD, 500 pmole/Kg QD and 100 pmole/Kg Q2D. The von Frey threshold for pregabalin 30 mpk was added by adopting the inhouse historical background. (* for p<0.05 by student's t-test)

[Reversal of Allodynia] FIG. 16B summarizes the observed outcomes of the von Frey scorings. The animals in the negative control group showed average von Frey threshold scores stabilized between ca 6 and 8 g over the period of the 14 days post the grouping.

In case of the paw of the ligated side, the allodynia was significantly reversed (student's t-test) in Day 1 and afterwards in the animals administered with the ASO at 20 pmole/Kg QD, 100 pmole/Kg Q2D and 500 pmole/Kg QD except for the 100 pmole/Kg QD group. In Day 14, however, the allodynia was also significantly reversed in the 100 pmole/Kg QD.

In case of the paw of the unligated side, the von Frey scores of the ASO treatment groups in Day 7 were higher than the score of the negative control group. The observed von Frey scores were 15.3 g (negative control), 17.6 g (20 pmole/Kg QD), 19.2 g (100 pmole/Kg QD), 20.1 g (100 pmole/Kg Q2D), and 19.5 g (500 pmole/Kg QD). However, there were no significant differences between the ASO treatment groups and the negative control group.

Example 8. Inhibition of Sodium Current by "ASO 7" in Rat L5 DRG Cells Activated with L5/L6 Spinal Nerve Ligation Cellular sodium current is usually measured by patch clamp. As sodium ions are taken up into cell, the intracellular sodium ion level increases. The intra-cellular sodium level can be evaluated using a sodium ion sensitive dye. "CoroNa Green" is a dye with a sodium ion specific chelator of crown ether type. Upon chelation of a sodium ion, "CoroNa Green" emits green fluorescence. "CoroNa Green" has been used to indirectly measure the cellular sodium level. The sodium level measured by "CoroNa Green" was found to correlate well with the sodium ion current measured by sodium ion patch clamp. [*Proc. Natl. Acad. Sci. USA* vol 106(38), 16145-16150 (2009)]

"ASO 7" was evaluated for its ability to down-regulate sodium ion current in rat DRG cells using "CoroNa Green" as follows.

[Extraction of DRG] In Day 0, male SD rats (6 weeks old, Harlan Laboratories, Italy) were subjected to "L5/L6 ligation" as described in "Example 5". The rats were sporadically subjected to von Frey scoring over a period of 4 weeks. In Day 31, a rat showing a low von Frey score was sacrificed to extract both the left (ligated side) and the right (non-ligated side) L5 DRG. The DRGs were immersed in 0.5 mL PBS immediately after the extraction.

[Preparation of L5 DRG Neuronal Cells] DRG cells were prepared according to the procedures disclosed in the literature [*Methods Mol Biol*. vol 846, 179-187 (2012); *PLoS One* vol 8(4); e60558 (2013)], which is briefly described in series as follows: ① DRG was transferred into an 1.5 mL e-tube containing 0.2 mL 0.125% collagenase (Collagenase Type IV, Cat. No. C5138-100MG, Sigma) in HBSS (Hank's Balanced Salt Solution, Cat. Number 14025-092, Life Technologies), chopped into pieces as small as possible with scissors, and incubated for 20 min in a $CO_2$ incubator at 37° C. under 5% $CO_2$ and 95% RH; ② 50 μL 0.25% trypsin/EDTA was added to the e-tube, which was kept in the incubator for another 10 min; ③ the e-tube was charged with 1 mL complete DMEM medium, and subjected to centrifugal sedimentation at 600 g for 5 min; ④ the resulting pellet was suspended in 4 mL Neurobasal-A medium (Neurobasal® Medium, Cat. No. 21103-049, Gibco) supplemented with 2×B-27 (B-27® Serum-Free Supplement, Cat. No. 17504-044, Gibco), 1× penicillin-streptomycin, 1×L-glutamine, and 1 mL of the cell suspension was carefully seeded onto a laminin-coated cover glass (Cat. No. GG-25-1.5-laminin, Neuvitro) placed in a 35 mm culture dish; ⑤ one day after the seeding, the dish was carefully charged with another 1 mL fresh Neurobasal-A medium; ⑥ two days after the seeding, the medium was replaced with 2 mL fresh Neurobasal-A medium supplemented with 1 μM Ara-C (cytosine β-D-arabinofuranoside, Cat. No. C1768-100MG, Sigma) in order to selectively suppress the growth of cells other than DRG neuronal cells; ⑦ four days after the seeding, the medium was replaced again with 2 mL fresh Neurobasal-A medium supplemented with 1 μM Ara-C; and ⑧ five or six days after the seeding, DRG neuronal cells were treated with ASO.

[ASO Treatment & CoroNa Assay] L5 DRG neuronal cells either with "L5/L6 ligation" or without "L5/L6 ligation" were treated with "ASO 7" at 0 (negative control), 100 or 1,000 zM. 30 hours later, the cells were washed with 2 mL HBSS, and then charged with 2 mL fresh HBSS. Then the cells were treated with 5 μM "CoroNa Green" (Cat. No. C36676, Life Technologies) at 37° C. 30 min later, the cells were washed 2 times with 2 mL HBSS, and charged with 2 mL fresh HBSS. The culture dish was mounted on an Olympus fluorescence microscope (Model BX53, Olympus) equipped with a CCD camera to continuously capture the green fluorescent images of the cells. The cells were acutely treated with 10 mM NaCl, and then the changes in the cellular fluorescent intensity were digitally recorded over a period of 300 sec. There were 4 to 5 cells per frame, i.e. per ASO concentration. The fluorescence intensities from each individual cell were traced at a resolution of second. The traces of the intracellular fluorescence intensities from individual cells were averaged using ImageJ program (version 1.50i, NIH), and the average traces are provided in FIGS. 13(A) and 13(B) for the cells with "L5/L6 ligation" and without "L5/L6 ligation", respectively. The average fluorescence intensity trace was taken as the individual intracellular sodium concentration trace for the cells treated with "ASO 7" at 0 (negative control), 100 or 1,000 zM.

Figure 17A:
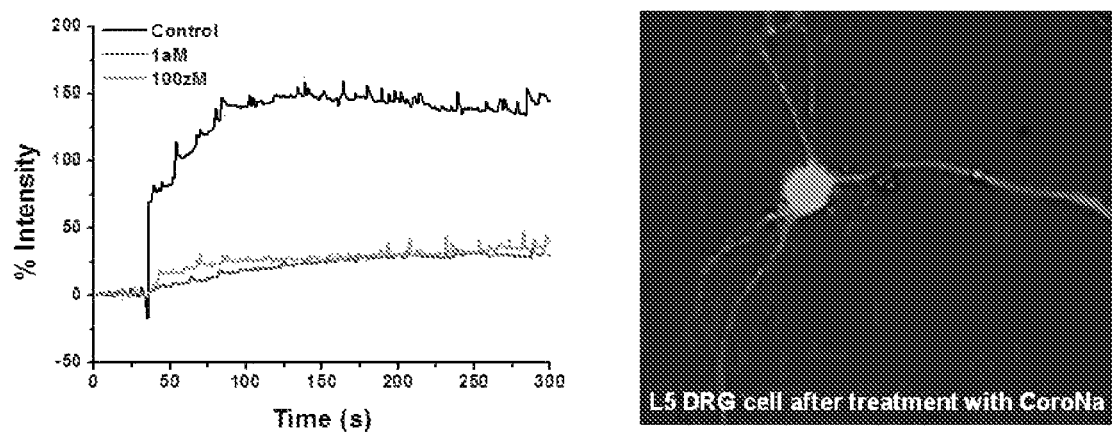
FIG. 17A. Average traces of the cellular fluorescence intensity (left) in rat L5 DRG neuronal cells with "L5/L6 ligation" following a 30 hour incubation with "ASO 7" at 0 (negative control), 100 or 1,000 zM along with a sample fluorescence image of a DRG neuronal cell treated with "CoroNa Green" (right).

[CoroNa Assay Results] In the DRG neuronal cells stimulated with "L5/L6 ligation" [cf. FIG. 17A], the treatment with "ASO 7" at 100 zM or 1 aM markedly inhibited the average cellular fluorescence intensity. At the time point of 150 sec, for example, the average cellular fluorescence intensity (i.e., the sodium current) decreased by 80~85% in the cells treated with the ASO.

Figure 17B:
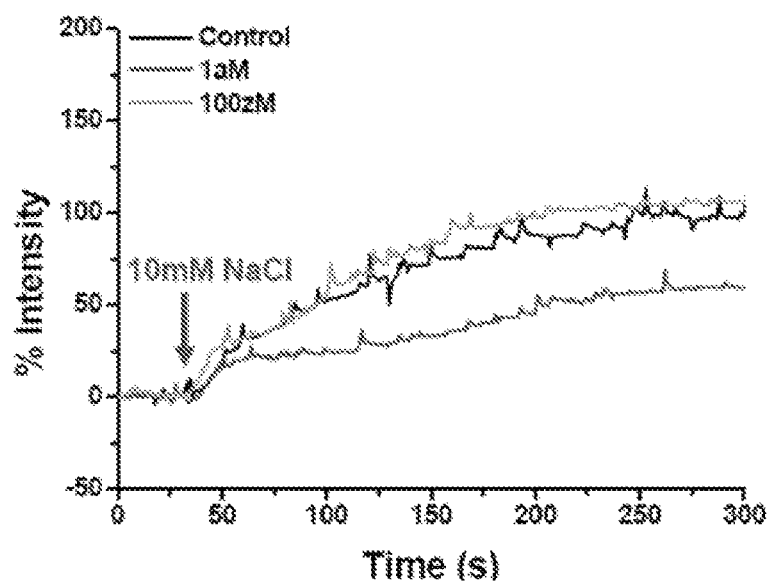
FIG. 17B. Average traces of the cellular fluorescence intensity in rat L5 DRG neuronal cells without "L5/L6 ligation" following a 30 hour incubation with "ASO 7" at 0 (negative control), 100 or 1,000 zM.

In the DRG neuronal cells without "L5/L6 ligation" [cf. FIG. 17B], the treatment with "ASO 7" at 1 aM induced a decrease in the average cellular fluorescence intensity. However, the observed decrease was about 50% at the time point of 150 sec, and not as marked as in the cells stimulated with "L5/L6 ligation". Furthermore, the treatment with "ASO 7" at 100 zM failed to inhibit the sodium current in the neuronal cells without "L5/L6 stimulation".

DRG neuronal cells without neuropathic stimulation are known to express various subtypes of VGSC including $Na_v1.7$, $Na_v1.8$, $Na_v1.2$ and so on. The $Na_v1.7$ subtype shows a limited contribution to the whole sodium current in DRG neuronal cells without stimulation. [*Nat Comm*. vol 3, Article Number 791: DOI:10.1038/ncomms1795 (2012)] The rat DRG neuronal cells without "L5/L6 ligation" may simulate such DRG neuronal cells without neuropathy. The observed inhibition of the sodium current in the DRG cells without "L5/L6 ligation" may reflect solely the contribution of the sodium current from the $Na_v1.7$ subtype.

In the meantime, neuronal cells are known to upregulate $Na_v1.7$ expression in response to persisting neuropathy. [*J Biol Chem*. vol 279(28), 29341-29350 (2004); *J Neurosci*. vol 28(26), 6652-6658 (2008)] The rat DRG neuronal cells with "L5/L6 ligation" may simulate DRG neuronal cells with neuropathy. "ASO 7" at both 100 zM and 1 aM inhibited the sodium current by 80~85% in the neuronal cells stimulated by "L5/L6 ligation". The higher inhibition of the sodium current by "ASO 7" in the DRG cells with "L5/L6 ligation" is consistent with the upregulation of $Na_v1.7$ in neuronal cells by chronic neuropathy.

Taken together the findings observed in the rat DRG neuronal cells with and without "L5/L6 ligation", "ASO 7" is concluded to selectively inhibit the expression of the $Na_v1.7$ subtype. "ASO 7" appears to inhibit the $Na_v1.7$ expression more potently in neuronal cells with neuropathy than in those cells without neuropathy.

Example 9. Reversal of Allodynia by "ASO 1" in Rats with DPNP

"ASO 1" specified in Table 1 is a 16-mer ASO fully complementary to the 3' splice site spanning the junction of intron 3 and exon 4 in the human SCN9A pre-mRNA as marked "bold" and "underlined" in the 25-mer SCN9A pre-mRNA sequence of

[(5'→ 3') uuguguuuag | GUACACUUUUACUGG (SEQ ID NO: 20)].

"ASO 1" possesses a 5-mer overlap with intron 3, and an 11-mer overlap with exon 4. "ASO 1" is fully complementary to the rat SCN9A pre-mRNA.

"ASO 1" was evaluated for its ability to reverse the allodynia elicited by diabetic peripheral neuropathic pain (DPNP) in rats.

[Induction of DPNP and Grouping] In Day 0, streptozotocin dissolved in citrate buffer (pH 6) was intra-peritoneally administered at 60 mg/Kg to male SD rats weighing ca 200 g in order to induce type I diabetes. [*J. Ethnopharmacol.* vol 72(1-2), 69-76 (2000)] In Day 10, rats with DPNP were randomly assigned into 2 groups of the negative control (vehicle only, PBS) and 100 pmole/Kg "ASO 1" and based on the von Frey scores of individual animals in Day 10 using von Frey microfilaments as described below. (N=8 per group)

[Von Frey Scoring by Up & Down Method] Allodynia was scored with a set of von Frey microfilaments (Touch Test®) according to the "Up & Down" method. [*J Neurosci. Methods* vol 53(1), 55-63 (1994)]

[ASO Administration & Allodynia Scoring] "ASO 1" was dissolved in PBS and subcutaneously administered to rats in Days 11, 13, 15, 17 and 19. Allodynia was scored 2 hours post dose in Days 11, 13, 15, 17 and 19, and additionally in Days 21 and 23 in order to assess the duration of the therapeutic activity post the final dose.

Figure 18A:
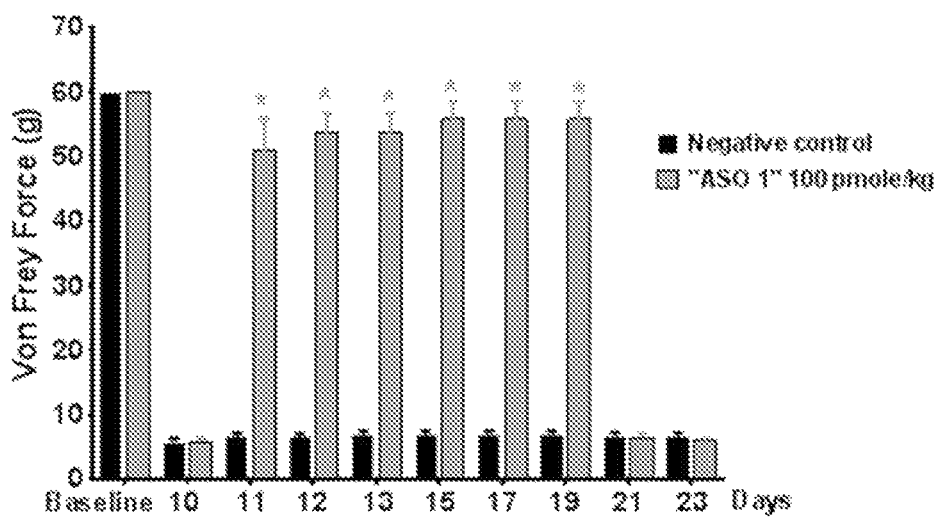
FIG. 18A. Reversal of the allodynia induced with DPNP in rats subcutaneously administered with 100 pmole/Kg "ASO 1". (error bar by standard error; * for p<0.05 by student's t-test)

[Reversal of Allodynia] FIG. 18A summarizes the observed outcomes of the von Frey scorings. The animals in the negative control group showed average von Frey thresholds stabilized between 6 and 7 g over the period of Days 10 to 23. In the animals received "ASO 1" at 100 pmole/Kg, the allodynia was significantly (student's t-test) reversed by ca 80% 2 hours post the first dose, i.e., in Day 11. The therapeutic activity slightly but gradually increased to ca 90% as the ASO was repeatedly administered till Day 19. Given the therapeutic activity completely washed out 2 days post the final dose, i.e., in Day 21, "ASO 1" may not possess a pharmacodynamic half-life long enough to support the dosing schedule of once per two days i.e., Q2D.

Nevertheless, "ASO 1" showed an onset time of a few hours in the reversal of the allodynia if judged by the von Frey scores in Day 11.

Example 10. Reversal of Allodynia by "ASO 2" and "ASO 6" in Rats with DPNP

"ASO 6" is a 13-mer ASO complementarily binding to a 13-mer sequence of the 3' splice site spanning the junction of intron 3 and exon 4 in the human SCN9A pre-mRNA as marked "bold" and "underlined" in the 25-mer SCN9A pre-mRNA sequence of

[(5'→ 3') uuguguuuag | GUACACUUUUACUGG (SEQ ID NO: 20].

"ASO 6" possesses a 5-mer overlap with intron 3, and an 8-mer overlap with exon 4. Although "ASO 2" and "ASO 6" target the same sequence in the human SCN9A pre-mRNA, "ASO 6" is considered to possess stronger affinity for complementary RNA than "ASO 2".

"ASO 2" and "ASO 6" were evaluated for their ability to reverse the allodynia elicited by DPNP in rats as described in "Example 9", unless noted otherwise.

Diabetes was induced in male SD rats (6 weeks old, Harlan Laboratories, Italy) by an intraperitoneal injection of streptozotocin at 60 mg/Kg in Day –10. In Day 0, 18 animals showing lowest von Frey scores were selected and assigned to three groups of the negative control (vehicle only, PBS), 60 pmole/Kg "ASO 2" and 30 pmole/Kg "ASO 6". (N=6 per group) Rats were subcutaneously administered with vehicle or ASO dissolved in PBS in Days 0, 2 and 4. Allodynia was scored by the electronic von Frey method as described in "Example 5".

Figure 18B:
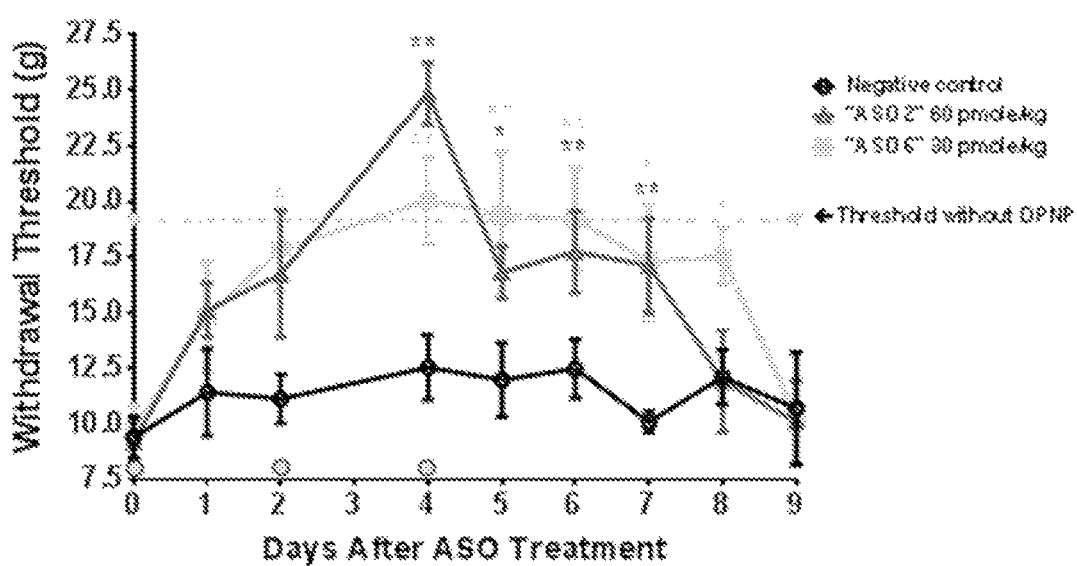
FIG. 18B. Reversal of the allodynia induced with DPNP in rats subcutaneously administered with 60 pmole/Kg "ASO 2" or 30 pmole/Kg "ASO 6" in Days 0, 2 and 4. The von Frey threshold without DPNP was added by adopting the inhouse historical background. (error bar by standard error; * and ** for p<0.05 and p<0.01 by student's t-test, respectively)

[Reversal of Allodynia] FIG. 18B summarizes the observed von Frey scores. The animals in the negative control group showed average von Frey thresholds stabilized at ca 10 to 12 g over the period of Days 0 to 9.

In the animals received 60 pmole/Kg "ASO 2", the allodynia was gradually reversed to the baseline level without diabetic neuropathy (i.e. full recovery level by in-house historical threshold) in Day 4 post the first dose in Day 0. The therapeutic activity significantly (student's t-test) persisted for another 3 days post the final dose in Day 4.

In the animals received 30 pmole/Kg "ASO 6", the therapeutic activity significantly (student's t-test) picked up in Day 2, and persisted for another 4 days post the final dose in Day 4. Thus, "ASO 6" reversed the allodynia more potently than "ASO 2". Unlike "ASO 1" in "Example 9", "ASO 6" showed a duration of therapeutic activity sufficiently long to support a dosing schedule of 2 times per week in rats.

[Miscellaneous] As the diabetes persisted, animals in the negative control group showed signs of physical collapse during von Frey scorings. Animals in the treatment groups were lively and responsive to the von Frey challenge, which would be consistent with the therapeutic activity of the ASOs.

Example 11. Analgesic Activity of "ASO 7" in Rat Formalin Test

Pain induced by an intraplantar injection of 20 µL 2% formalin markedly decreased in global SCN9A KO mice. The inhibitory extent was 73% and 86% for Phase I (0 to 10 min post the formalin injection) and Phase II (15 to 45 min post the formalin injection), respectively. [*PLoS One* vol 9(9), e105895 (September 2014)]

"ASO 7" possesses a single mismatch at the 5'-end of the rat SCN9A pre-mRNA, and was evaluated for its analgesic activity in rat formalin test as follows.

[Grouping and ASO Treatment] In Day –6, 24 male SD rats (6 weeks old, Harlan Laboratories, Italy) were randomly assigned to 4 groups of the negative control (no ASO treatment) and three "ASO 7" treatment groups of 10, 30 and 100 pmole/Kg. (N=6 per group) Each group of animals subcutaneously received "ASO 7" at 0 (negative control), 10, 30 or 100 pmole/Kg in Days –6 and –2. "ASO 7" was diluted in PBS for the injection.

[Formalin Test] In Day 0, acute pain was induced by an intraplantar injection of 50 μL 5% formalin in the left hind paw Immediately after the formalin injection, each rat was subjected to individual video recording for an hour post the formalin injection. The video was replayed to visually score the pain responses for each inflicted animal.

Figure 19A:
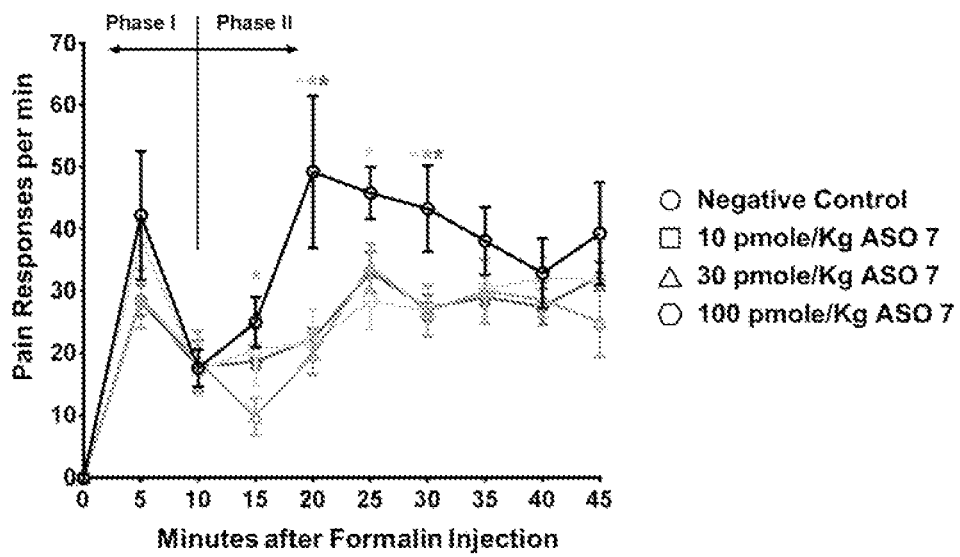
FIG. 19A. Inhibition of pain induced by an intraplantar injection of 5% formalin in rats subcutaneously administered with "ASO 7" at 0 (negative control), 10, 30 or 100 pmole/Kg. (error bar by standard error; *p<0.05 by student's t-test)

[Analgesic Activity] FIG. 19A summarizes the observed pain scores by group at various time points post the formalin injection. The pain responses in Phase II (AUC between 10 and 40 min) significantly decreased (*p<0.05 by student's t-test) by 33%, 36% and 32% in the treatment groups of 10, 30 and 100 pmole/Kg, respectively. In the meantime, the pain responses in Phase I (AUC between 0 and 10 min) decreased by 14%, 40% and 43% without statistical significance in the treatment groups of 10, 30 and 100 pmole/Kg, respectively.

Example 12. Analgesic Activity of "ASO 10" in Rat Formalin Test

"ASO 10" specified in Table 1 is a 14-mer SCN9A ASO partially complementary to the human SCN9A pre-mRNA with a single mismatch at the 5'-end of the target pre-mRNA sequence as marked "bold" and "underlined" in the 25-mer SCN9A pre-mRNA sequence of

[(5'→ 3') uugu"g"uuuag | GUACACUUUUACUGG (SEQ ID NO: 20)], wherein the single mismatch in intron 3 is marked with quote sign (" "). In the meantime, "ASO 10" is fully complementary to the 3' splice site spanning the junction of intron 3 and exon 4 within the rat SCN9A pre-mRNA as marked "bold" and "underlined" in the 20-mer rat SCN9A pre-mRNA sequence of

[(5'→ 3') uuuccuuuag | GUACACUUUU (SEQ ID NO: 19)].

"ASO 10" possesses a 6-mer overlap with intron 3 and an 8-mer overlap with exon 4.

"ASO 10" was evaluated for its analgesic activity in rat formalin test as described in "Example 11", unless noted otherwise.

[Grouping and ASO Treatment] 36 male SD rats (7 weeks old, Harlan Laboratories, Italy) were randomly assigned to four groups of the negative control (no ASO treatment) and three "ASO 10" treatment groups of 15, 50 and 150 pmole/Kg. (N=9 per group) Each group of animals were subcutaneously administered with "ASO 10" at 0 (negative control), 15, 50 or 150 pmole/Kg in Days −6 and −2. The ASO was administered as dissolved in PBS.

Figure 19B:
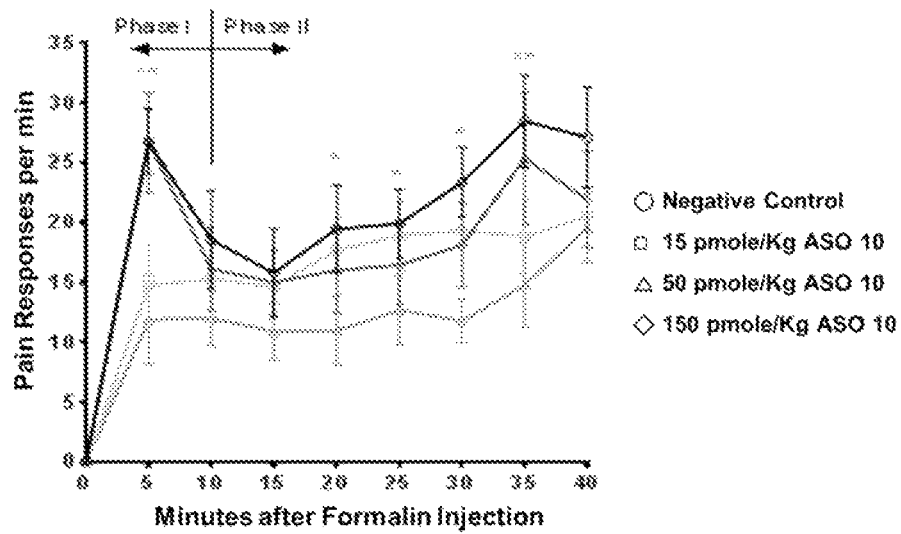
FIG. 19B. Inhibition of pain induced by an intraplantar injection of 5% formalin in rats subcutaneously administered with "ASO 10" at 0 (negative control), 15, 50 or 150 pmole/Kg. (error bar by standard error; *p<0.05 by student's t-test)

[Analgesic Activity] FIG. 19B summarizes the observed pain scores by group at various time points. The pain responses in Phase II (AUC between 10 and 40 min) significantly decreased (student's t-test) by 17% and 41% in the treatment groups of 15 and 50 pmole/Kg, respectively. In the meantime, the pain responses in Phase I (AUC between 0 and 10 min) significantly decreased by 38% and 50% in the treatment groups of 15 and 50 pmole/Kg, respectively.

Interestingly, the 150 pmole/Kg group failed to show therapeutic activity both in Phase I and Phase II. "ASO 10" at 150 pmole/Kg would be an overdose inducing an transcription upregulation by the "exon intron circular RNA (EIciRNA)" accumulated during the exon skipping with "ASO 10". [*Nature Struc. Mol. Biol.* vol 22(3), 256-264 (2015)].

Example 13. Inhibition of $Na_v1.7$ Expression in L5 DRG by "ASO 7" in Rats Inflicted with an Intraplantar Formalin Injection "ASO 7" was evaluated by IHC (immunohistochemistry) for its ability to inhibit the expression of $Na_v1.7$ in the L5 DRG of male SD rats inflicted with an intraplantar injection of formalin as follows.

[ASO Treatment and Formalin Injection] In Day −5, male SD rats (6 weeks old, Harlan Laboratories, Italy) were randomly assigned to 4 groups of the negative control (no ASO treatment) and three "ASO 7" treatment groups of 1, 6 and 30 pmole/Kg. Each group of animals subcutaneously received "ASO 7" at 0 (negative control), 1, 6 or 30 pmole/Kg in Days −5 and −1. "ASO 7" was diluted in PBS and used for the injection. In Day 0, all the animals received a single intraplantar injection of 50 μL 5% formalin.

[Extraction of L5 DRG and $Na_v1.7$ IHC] In Day 8, the rats were anesthetized with zoletil/rompun and subjected to sampling of the L5 DRG of the formalin injected side. (N=2 per group) The DRG samples were subjected to $Na_v1.7$ IHC as briefly described below.

The DRG samples were cryo-sectioned and subjected to immunostaining in series with a primary anti-$Na_v1.7$ antibody (Cat. No. ASC-008, Alomone) at 1:500 dilution, with a secondary anti-IgG (Cat No. BA-1100, Vector) at 1:200 dilution, and then with Dylight 594-steptavidin (Cat No. SA-5594, Vector, Calif., USA) at 1:200 dilution for red fluorescence tagging. IHC images were captured on a Zeiss slide scanner for the $Na_v1.7$ expression in DRG.

Figure 20A:
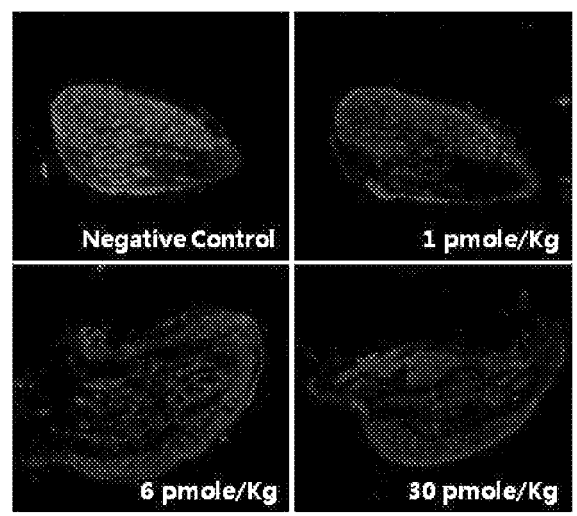
FIG. 20A. Representative IHC images by group for $Na_v1.7$ expression in L5 DRG in rats subcutaneously administered with "ASO 7" at 0 (negative control), 1, 6 or 30 pmole/Kg.

[Inhibition of $Na_v1.7$ Expression in L5 DRG] FIG. 20A provides a representative set of $Na_v1.7$ IHC images by group. $Na_v1.7$ expression in DRG was notably high in the negative control group compared to the expression in the ASO treatment groups.

Figure 20B:
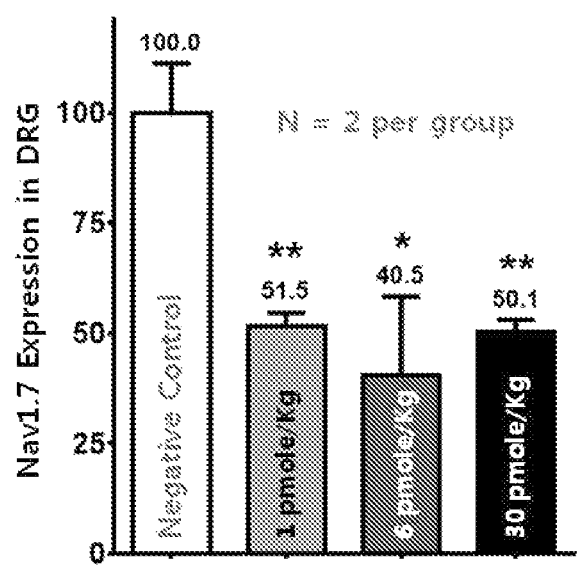
FIG. 20B. Relative $Na_v1.7$ expression level in L5 DRG in rats subcutaneously administered with "ASO 7" at 0 (negative control), 1, 6 or 30 pmole/Kg. (error bar by standard error; * for p<0.05 and ** for p<0.01 by student's t-test)

The level of red color in each individual IHC image was digitally scored by using NIH ImageJ program, and the individual levels were subjected to statistical analysis by group. (N=2 per group) FIG. 20B summarizes the $Na_v1.7$ expression level digitally quantified by group. The $Na_v1.7$ expression level significantly decreased (student's t-test) by ca 50~60% in all the ASO treatment groups.

Example 14. Reversal of Allodynia in Rats with Spinal Neuropathy by "ASO 10" (1)

"ASO 10" was evaluated for its ability to reverse the allodynia in rats with spinal neuropathy induced by "L5/L6 ligation" as described in "Example 6" unless noted otherwise.

[Grouping] In Day −14, male SD rats (5 weeks old, Harlan Laboratories, Italy) were subjected to "L5/L6 ligation". In Day 0, 36 animals were selected based on their individual von Frey scores in Day 0, and assigned to 4 groups of the negative control group (i.e., no ASO treatment), three ASO treatment groups of 1, 3 and 10 pmole/Kg. (N=9 per group)

[ASO Treatment and Von Frey Scoring] Rats subcutaneously received in the afternoon "ASO 10" at 0 (negative control), 3 and 10 pmole/Kg in Days 0, 3 and 7. In the 1 pmole/Kg treatment group, the dose was initially 1 pmole/

Kg in Day 0, and then raised to 30 pmole/Kg in Days 3 and 7 due to lack of the therapeutic activity at 1 pmole/Kg in Days 2 and 3.

Figure 21A:
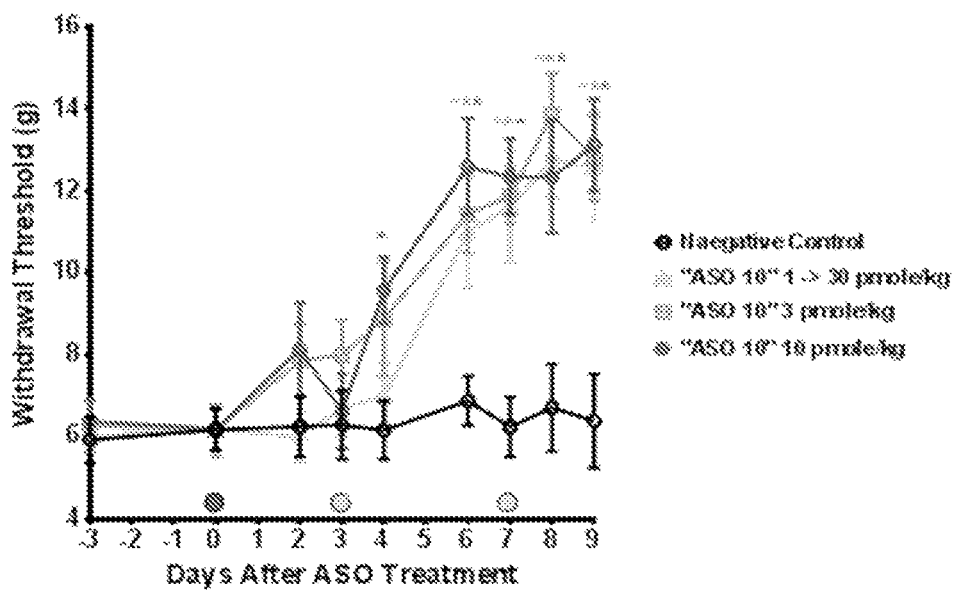
FIG. 21A. Reversal of allodynia in rats with L5/L6 ligation by subcutaneous administration of "ASO 10" at 1 (escalated to 30 pmole/Kg in Days 3 and 7), 3 and 10 pmole/Kg. (error bar by standard error; * for p<0.05 by student's t-test).

[Reversal of Allodynia] FIG. 21A summarizes the observed von Frey scores. The animals in the negative control group showed average von Frey scores (withdrawal threshold) stabilized between ca 6 and 7 g over the period of the 9 days post the grouping.

The allodynia was reversed gradually and significantly over a period of a week by administrations with "ASO 10" at 3 to 30 pmole/Kg. The therapeutic activity plateaued out to the von Frey score of ca 13 g for all the treatment groups.

In the 1 pmole/Kg group, however, the therapeutic activity started picking up after the dose was elevated from 1 pmole/Kg to 30 pmole/Kg in Day 3. The allodynia was significantly reversed by ca 40% in Day 6 after the dose was increased to 30 pmole/Kg, if a historic background threshold of ca 18 g was taken as the von Frey score without "L5/L6" ligation. The analgesic efficacy increased to ca 60% in Day 8.

In the 3 pmole/Kg group, the allodynia was significantly reversed (student's t-test) in Day 6 with a modest (ca 40~50%) efficacy. The therapeutic efficacy increased to 65+% in Day 8.

In the 10 pmole/Kg group, the allodynia was significantly reversed in Day 4 with an efficacy of ca 25~30%. The therapeutic efficacy increased to ca 60% in Day 9. However, the efficacy remained stagnant from Day 6.

Example 15. Reversal of Allodynia in Rats with Spinal Neuropathy by "ASO 10" (2)

"ASO 10" was evaluated for its ability to reverse the allodynia in rats with spinal neuropathy induced by "L5/L6 ligation" as described in "Example 6" unless noted otherwise.

[Grouping] In Day −10, male SD rats (6 weeks old, Harlan Laboratories, Italy) were subjected to "L5/L6 ligation". In Day 0, 36 animals were selected based on their individual von Frey scores in Day 0, and randomly assigned to 4 groups of the negative control group (i.e., no ASO treatment), two ASO treatment groups of 100 pmole/Kg once per every 4 or 5 days, and the positive control group of pregabalin 30 mg/Kg. (N=9 per group)

[ASO Treatment and Von Frey Scoring] Rats subcutaneously received in the afternoon "ASO 10" at 0 (negative control), 100 pmole/Kg in Days 0 and 4, 100 pmole/Kg in Days 0 and 5. Allodynia was scored in the morning on a daily basis. The rats of the positive control group were orally administered with pregabalin 30 mg/Kg one hour prior to the von Frey scoring. The ASO was administered as dissolved in PBS.

Figure 21B:
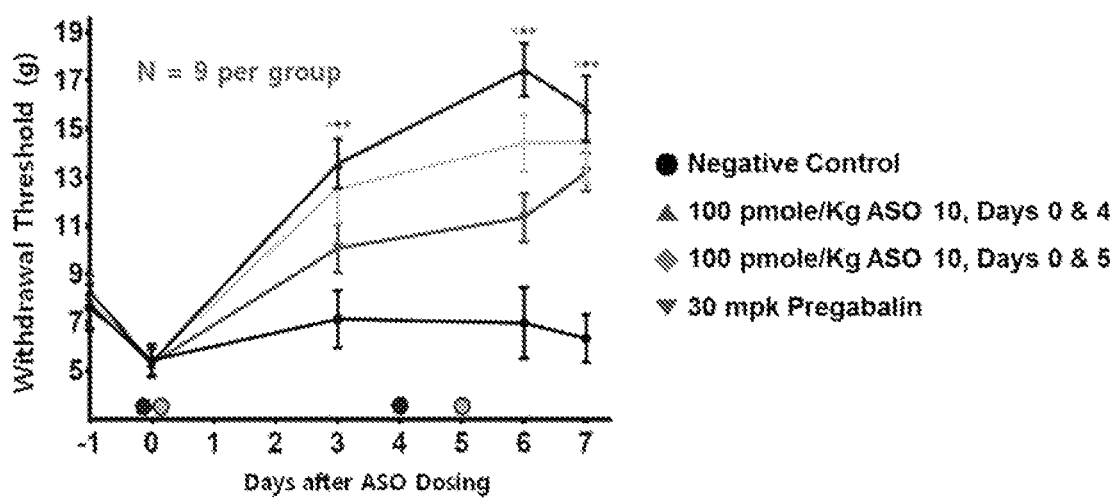
FIG. 21B. Reversal of allodynia in rats with L5/L6 ligation by subcutaneous administration of "ASO 10" at 100 pmole/Kg, once per every 4 or 5 days, or by oral administration of pregabalin 30 mpk.

[Reversal of Allodynia] FIG. 21B summarizes the observed von Frey scores. The animals in the negative control group showed average von Frey scores (withdrawal threshold) stabilized between ca 6 and 7 g over the period of the 7 days post the first ASO treatment. The rats in the pregabalin 30 mg/Kg group showed average von Frey scores of ca 10~11 g, although the observed score in Day 7 was ca 13 g due to sedation.

In the ASO treatment group of once per every 4 days, the allodynia was significantly reversed (student's t-test) in all the tested occasions in Days 3, 6 and 7, and significantly superior to pregabalin 30 mg/Kg in Days 3 and 6. Thus the dosing frequency of once per every 4 days in rats appears to be appropriate to maintain the therapeutic activity superior to pregabalin 30 mpk. It is noted that the allodynia was reversed in Day 8 to ca 90% of the basal level without spinal neuropathy against the in-house historical background.

In the ASO treatment group of once per every 5 days, the allodynia was significantly reversed (student's t-test) in all the tested occasions in Days 3, 6 and 7, and significantly superior to pregabalin 30 mg/Kg only in Days 3. Thus the dosing frequency of once per every 5 days appears to be too long to secure the therapeutic activity significantly superior to pregabalin 30 mg/Kg.

[$Na_v1.7$ Expression in Spinal Cord] In Day 7, animals were anesthetized with zoletil/rompun, perfused with PBS supplemented with formalin in order to preserve the structural integrity of the spinal cord, and subjected to sampling of spinal cord. (N=3 per group) Spinal cord samples were processed into paraffin block, and were subjected to IHC in series for $Na_v1.7$ expression (red staining) with a $Na_v1.7$ antibody (Cat. No. ASC-008, Alomone) and for neuronal cell body (green staining) with a Neu antibody (Cat. No. Ab104224, Abcam). The nucleus was stained with DAPI (blue).

Figure 22:
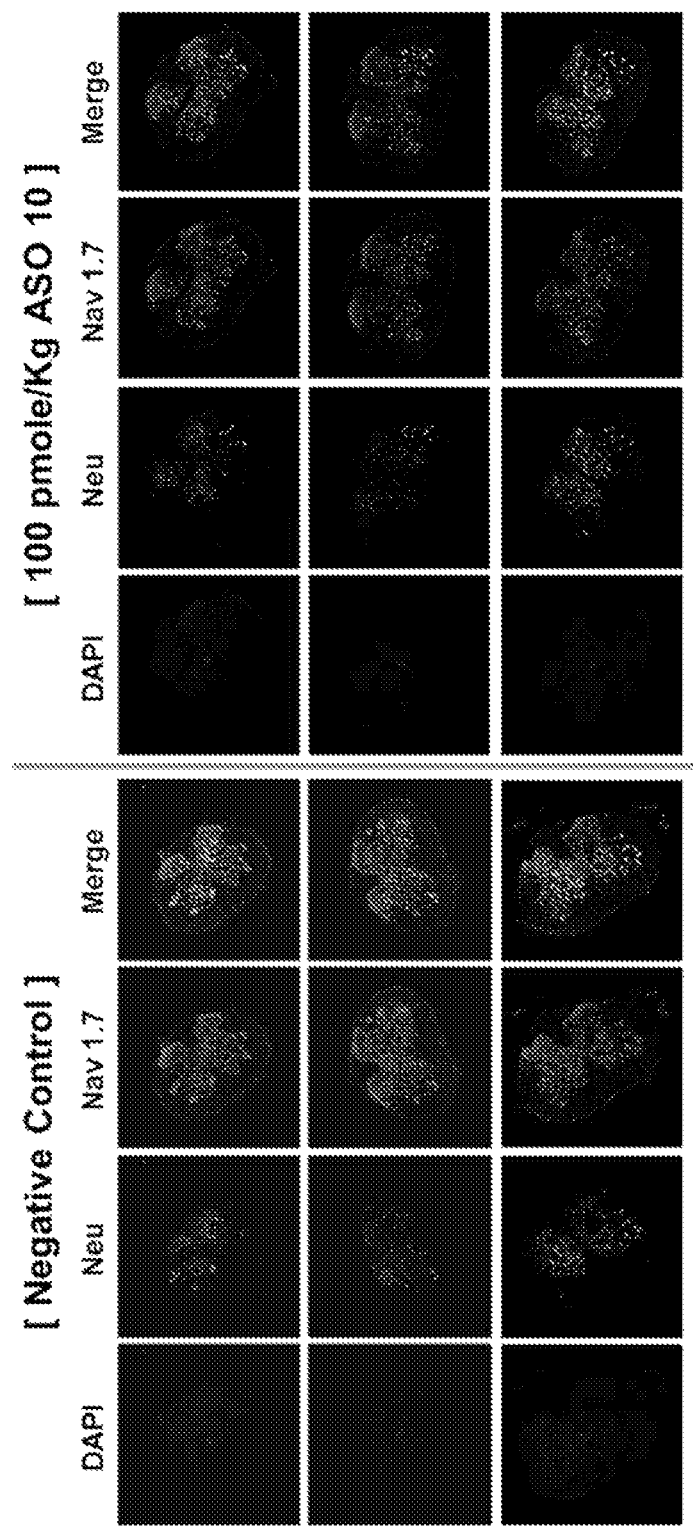
FIG. 22. IHC images of $Na_v1.7$ expression (red), neuronal cell body (green), and the nucleus (blue) with the spinal cord samples obtained from the treatment group of "ASO 10" dosed in Days 0 and 4 (top panel images) and from the negative control group (bottom panel images). (N=3 per group)

FIG. 22 provides IHC images captured on a Zeiss slide scanner. The $Na_v1.7$ expression level markedly decreased in the spinal cord samples of the ASO treatment group with dosing in Days 0 and 4 compared to the expression level in the spinal cord samples of the negative control group. Thus the ASO appears to have readily distributed to the spinal cord and inhibited the expression of $Na_v1.7$ in the spinal cord upon subcutaneous administration.

Example 16. Inhibition of $Na_v1.7$ Expression in Rat DRG Neuronal Cells by "ASO 10"

"ASO 10" was evaluated for its ability to inhibit the expression of $Na_v1.7$ in rat L5 DRG neuronal cells as described below.

[Preparation of L5 DRG Neuronal Cells] Male SD rats (7 weeks old, Harlan Laboratories, Italy) were subjected to tight "L5/L6 ligation" as described in "Example 5". 7 days later, 4 rats were anesthetized with zoletil/rompun for the extraction of L5 DRG of the ligated side. The DRGs were pooled and processed in order to prepare DRG neuronal cells as described in "Example 8".

[ASO Treatment] DRG neuronal cells were treated with "ASO 10" at 0 (negative control), 10, 100 or 1,000 zM for 24 hours, and then subjected to lysis for western blot against a $Na_v1.7$ antibody (Cat. No. ab85015, Abcam) probing the C-terminal of the $Na_v1.7$ protein. β-actin was probed for reference. "ASO 10" stock solutions were dissolved in DDW and aliquoted to the culture medium.

Figure 23A:
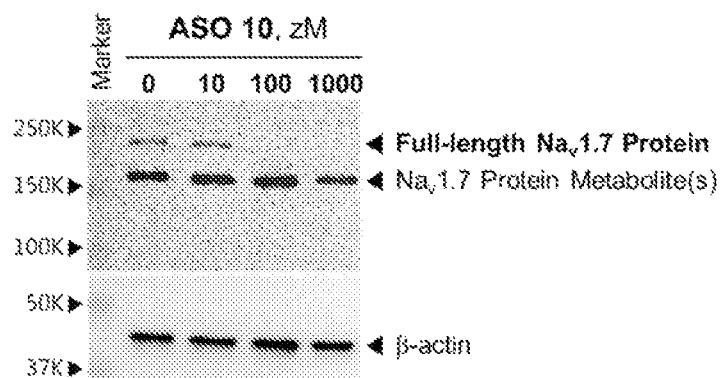
FIG. 23A. Western blot data for the Nav1.7 expression in L5 DRG neuronal cells treated with "ASO 10" for 24 hours at 0 (negative control), 10, 100 or 1,000 zM.

[Inhibition of $Na_v1.7$ Expression] FIG. 23A provides the western blot data obtained with the DRG neuronal cells treated with "ASO 10" at 0 (negative control), 10, 100 or 1,000 zM. All the lysates yielded a strong band at 170~200K, which would be metabolites of the $Na_v1.7$ protein. The full-length $Na_v1.7$ protein band was detected at 220~240K only with the lysates of the negative control and 10 zM "ASO 10". Thus $Na_v1.7$ expression was fully inhibited in rat DRG neuronal cells following a 24 hour incubation with "ASO 10" at 100 to 1,000 zM.

"ASO 10" is a 14-mer ASO fully complementary to the rat SCN9A pre-mRNA, whilst "ASO 7" is a 14-mer ASO fully complementary to the human SCN9A pre-mRNA. The SCN9A inhibitory profiles obtained with "ASO 10" in rat neuronal cells can be predictably extrapolated to the SCN9A inhibitory profiles of "ASO 7" in human neuronal cells.

Example 17. qPCR for SCN9A mRNA in Rat DRG Neuronal Cells Treated with "ASO 10" with cDNA Synthesized by One-Step PCR "ASO 10" was evaluated by SCN9A nested qPCR for its ability to induce changes in the rat SCN9A mRNA level in rat DRG cells as described below.

[Preparation of L5 DRG Neuronal Cells] A male SD rat (6 weeks old, Harlan

Laboratories, Italy) was anesthetized with zoletil/rompun to extract the L5 DRGs. The L5 DRG samples were processed as described in "Example 8" in order to prepare L5 DRG neuronal cells.

[ASO Treatment] Rat L5 DRG neuronal cells were treated with "ASO 10" at 0 (negative control), 10, 30, 100 or 300 zM. (1 culture dish per each ASO concentration) "ASO 10" stock solutions were dissolved in DDW and aliquoted to the culture medium.

[RNA Extraction & cDNA Synthesis by One-step PCR] Following an incubation with "ASO 10" for 24 hours, total RNA was extracted from cells using "Universal RNA Extraction Kit" (Cat. Number 9767, Takara) according to the manufacturer's instructions. 200 ng of RNA template was subjected to a 25 μL reverse transcription reaction using One Step RT-PCR kit (Invitrogen, USA) against a set of exon specific primers of [exon 2_forward: (5'→3') CAATCTTCCG-TTTCAACGCC (SEQ ID NO: 21), and exon 10_reverse: (5'→3') ACCACAGCCAGGATCAAGTT (SEQ ID NO: 22)] according to the following cycle conditions: 50° C. for 30 min and 94° C. for 2 min, which was followed by 15 cycles of 30 sec at 94° C., 30 sec at 55° C., and 2 min at 72° C.

[Nested qPCR Amplification] The cDNA solutions (duplicate per ASO concentration) were diluted by 100 times, and 1 μL of each diluted cDNA solution was subjected to a 20 μL Real-Time PCR reaction with a TaqMan probe (Cat. No. Rn01514993_mH, ThermoFisher) targeting the junction of exon 3 and exon 4 in the SCN9A pre-mRNA according to the following cycle conditions: 95° C. for 30 sec followed by 40 cycles 5 sec at 95° C., and 30 sec at 60° C.

Figure 23B:
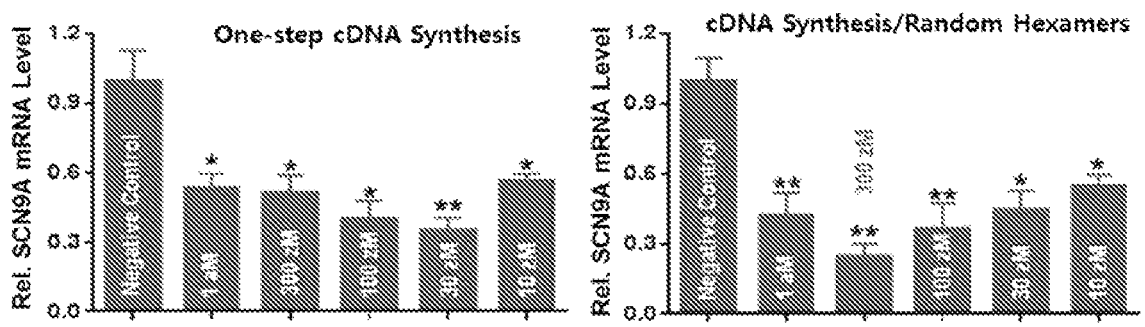
FIG. 23B. qPCR data for the full-length SCN9A mRNA with cDNA synthesis by one-step PCR (left figure) and cDNA synthesis using random hexamers (right figure) in L5 DRG neuronal cells treated with "ASO 10" at 0 (negative control), 10, 30, 100 or 300 zM for 24 hours. (error bar by standard error; * for p<0.05 and ** for p<0.01 by student's t-test)

The left side figure in FIG. 23B summarizes the observed qPCR data, in which the full-length SCN9A mRNA level significantly decreased (student's t-test) in the cells treated with "ASO 10" by ca 50~60%.

Example 18. qPCR for SCN9A mRNA in Rat DRG Neuronal Cells Treated with "ASO 10" with cDNA Synthesis with Random Hexamers "ASO 10" was evaluated by SCN9A qPCR for its ability to inhibit the expression of the SCN9A mRNA in rat L5 DRG neuronal cells. Total RNA was prepared as described in "Example 17", and subjected to cDNA synthesis using random hexamers. The cDNA solutions (duplicate per ASO concentration) were diluted by 100 times, and 1 μL, of each diluted PCR product was subjected to a 20 μL Real-Time PCR reaction with the TaqMan probe targeting the junction of SCN9A exon 3 and exon 4 according to the following cycle conditions: 95° C. for 30 sec followed by 40 cycles 5 sec at 95° C., and 30 sec at 60° C.

The cDNA solutions were also subjected to qPCR amplification for the GAPDH mRNA. The Ct values of the SCN9A mRNA were normalized against the Ct values of the GAPDH mRNA.

The right side figure in FIG. 23B provides the SCN9A qPCR data normalized against GAPDH. The full-length SCN9A mRNA expression level significantly decreased (student's t-test) in the cells treated with "ASO 10" by ca 45~75%.

Example 19. Inhibition of Sodium Current in L5 DRG Neuronal Cells by "ASO 10" (1)

"ASO 10" was evaluated for its ability to inhibit the sodium current in rat L5 DRG neuronal cells as follows.

[Preparation of DRG Neuronal Cells] Male SD rats (5 weeks old, Daehan Biolink, South Korea, www.dbl.co.kr) were subjected to tight "L5/L6 ligation" as described in "Example 5". 10 to 14 days after the ligation, rats were anesthetized with zoletil/rompun for the extraction of L5 DRG of the ligated side. L5 DRG neuronal cells were prepared as described below.

① L5 DRG acutely extracted from rat was transferred into a 1.5 mL e-tube containing 0.2 mL 0.125% collagenase (Collagenase Type IV, Cat. No. C5138-100MG, Sigma) in HBSS (Hank's Balanced Salt Solution, Cat. Number 14025-092, Life Technologies), chopped into pieces as small as possible with scissors, and then incubated for 20 min in a $CO_2$ incubator at 37° C. under 5% $CO_2$ and 95% RH; ② then 50 μL 0.25% trypsin/EDTA was added to the e-tube, which was kept in the incubator for another 10 min; ③ the e-tube was charged with 1 mL complete DMEM medium, and subjected to centrifugal sedimentation at 600 g for 5 min; ④ then the resulting pellet was suspended and transported as sealed in a 15 mL falcon tube containing ca 15 mL Neurobasal-A medium; ⑤ following a transportation of ca an hour, 0.5 mL of the cell suspension was carefully seeded onto a laminin-coated cover glass placed in a well of 24-well plate culture dish; ⑥ the culture plate was incubated in a $CO_2$ incubator at 37° C. for 2 hours to attach cells onto the cover glass.

[ASO Treatment] The L5 DRG neuronal cells prepared as above were treated with "ASO 10" at 0 (negative control), 10, 30, or 100 zM, and kept in the incubator for 4 hours. The ASO stock solutions were prepared in DDW supplemented with 0.1% (v/v) Tween80. Each stock solution (including vehicle only for the negative control) was aliquoted to the culture medium so as to contain 0.0001% (v/v) Tween80 for patch clamp assays.

[Manual Patch Clamp Assay] Then the DRG neuronal cells were subjected to sodium current manual patch clamp assays on a sodium patch clamp apparatus (Axopatch 200B Amplifier, Axon Instruments). Patch clamp assays usually took 4 hours. Thus the cells are considered to have been treated with ASO for 4 to 8 hours (i.e., ca 6 hours on average).

[Data Pooling & Analysis] The above experiment was repeated over several independent occasions in order to increase the statistical power per ASO dose. Only the sodium current data from TTX-sensitive cells was included in the pooling for statistical analysis.

Figure 23C:
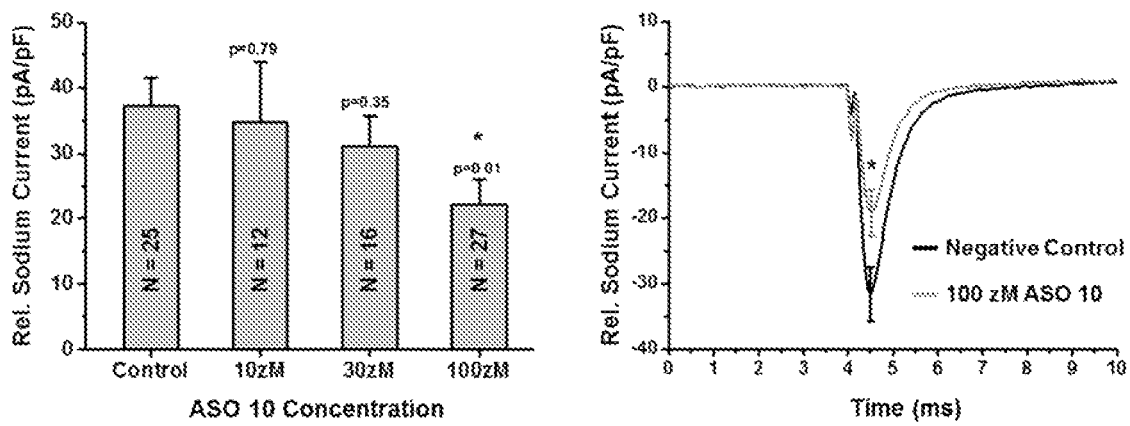
FIG. 23C. Pooled average of the sodium current data in L5 DRG neuronal cells treated with "ASO 10" for ca 6 hours at 0 (negative control), 10, 30, or 100 zM (left side figure); and the average traces of the pooled sodium current data for the negative control cells and the cells treated with 100 zM "ASO 10" for ca 6 hours (right side figure). The sodium current data was pooled as normalized against the cell size. (N refers to the number of the cells pooled for data analysis per group; error bar by standard error; and * for p<0.05 by student's t-test)

FIG. 23C summarizes the pooled sodium current data normalized against the cell size of DRG neuronal cells. The sodium current gradually decreased as the ASO concentration was increased from 10 zM to 100 zM. The sodium current significantly decreased by ca 40% in the cells treated with 100 zM "ASO 10" for ca 6 hours on average. Given that DRG neuronal cells express not only $Na_v1.7$ but also other subtypes of voltage-gated sodium channel, the observed decrease of ca 40% in the sodium current at 100 zM "ASO 10" should be taken as marked for the $Na_v1.7$ knockdown by "ASO 10".

Example 20. Inhibition of Sodium Current in L5 DRG Neuronal Cells by "ASO 10" (2)

In-house evaluations of rats from a number of suppliers indicate that the $Na_v1.7$ expression level in L5 DRG would vary much with age and supplier. "ASO 10" was evaluated for its ability to inhibit the sodium current in rat L5 DRG neuronal cells of a different source as described in "Example 19", unless noted otherwise.

[Preparation of DRG Neuronal Cells] Male SD rats (5 weeks old, Harlan Laboratories/Envigo, Denmark) were subjected to tight "L5/L6 ligation" as described in "Example 5". 10 to 14 days after the ligation, rats were anesthetized with zoletil/rompun for the extraction of L5 DRG of the ligated side. L5 DRG neuronal cells were prepared as described below.

[ASO Treatment] The L5 DRG neuronal cells prepared as above were treated with "ASO 10" at 0 (negative control) or 100 zM, and kept in the incubator for 4 hours. The ASO stock solutions were prepared in DDW.

The sodium current normalized against the cell size significantly ($p<0.05$) decreased by ca 55% in the cells treated with 100 zM "ASO 10" for ca 6 hours on average. (N=14 for the negative control; and N=15 for 100 zM "ASO 10") The normalized sodium current for the negative control was higher by 37% in this example than in "Example 19". Thus the contribution of $Na_v1.7$ to the sodium current in DRG neuronal cells should be considerably higher in the rats from the Harlan Laboratories of this example than in the rats from the Daehan Biolink of "Example 19".

Example 21. Reversal of Allodynia by "ASO 7" in Rats with Spinal Neuropathy. (2)

"ASO 7" was evaluated for its ability to reverse the allodynia in rats with spinal neuropathy induced by "L5/L6 ligation" as described in "Example 6", unless noted otherwise.

[SNL Surgery and Grouping] In Day −10, male SD rats (5 weeks old, Daehan Biolink, South Korea, www.dbl.co.kr) were subjected to "L5/L6 ligation". In Day 0, 48 animals were selected based on the lowest individual von Frey scores in Day 0, and randomly assigned into 6 groups of the negative control group (i.e., no ASO treatment), pregabalin 30 mg/Kg, and the four treatment groups of 5, 25, 125 and 625 fmole/Kg "ASO 7". (8 animals per group)

[ASO Treatment and Von Frey Scoring] Rats subcutaneously received "ASO 7" at 0 (negative control), 1, 3 or 6 pmole/Kg in the afternoon in Days 0, 3, 6 and 9. Allodynia was scored by the electronic von Frey scoring method described in "Example 5" in the morning. Pregabalin was orally administered one hour prior to each von Fret scoring occasion. The ASO was administered as dissolved in PBS supplemented with 0.1% Tween80.

Figure 24A:
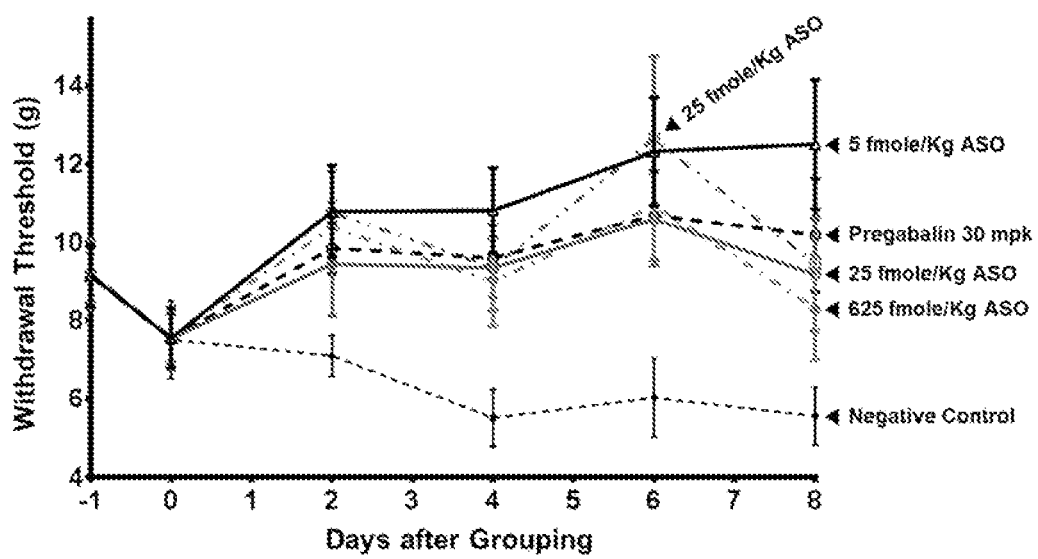
FIG. 24A. Reversal of the allodynia induced by L5/L6 ligation in SD rats subcutaneously administered with "ASO 7" at 0 (negative control), 5, 25, 125 or 625 fmole/Kg in Days 0, 3, and 6. The treatment group of pregabalin 30 mg/Kg po was included as the positive control. (N=8 per group; and error bar by standard error)

[Reversal of Allodynia] FIG. 24A summarizes the observed outcomes of the von Frey scorings. The animals in the negative control group showed average von Frey scores (withdrawal threshold) stabilized at ca 6 g over Days 4 to 8. In the meantime, the pregabalin 30 mg/Kg group (i.e., positive control group) showed average von Frey scores stabilized at ca 10 g. Given that average von Frey scores of ca 21 g were observed with naive animals (i.e. without ligation and treatment), the allodynia was significantly reversed in Days 2, 4, and 6 by 20 to 30% in the pregabalin treatment group.

"ASO 7" significantly reversed (student's t-test) the allodynia in Days 2 to 8 at 5 fmole/Kg, in Days 2, 4 and 6 at 25 and 125 fmole/Kg, and in Days 4 and 6 at 625 fmole/Kg. The most active group was the 5 fmole/Kg group, even though there were no significant differences between ASO treatment groups. Pregabalin also significantly reversed the allodynia by 20 to 30% during Days 2 to 8. The most active group was the 5 fmole/Kg group showing a ca 40% reversal of the allodynia, even though there were no significant differences between ASO treatment groups. However, the efficacies of the treatment groups were not significantly different from the efficacy of the pregabalin group.

Example 22. Analgesic Activity of "ASO 2" Against Sub-Chronic Inflammatory Pain in Rats "ASO 2" was evaluated for its ability to inhibit sub-chronic inflammatory pain in rats inflicted with an intra-plantar injection of Freund's complete adjuvant (FCA) as described below.

[Induction of Sub-chronic Inflammation] In Day −17, male SD rats (7 weeks old) received an intra-plantar injection of 100 μL FCA (Cat. No. F5881-6X10ML, Sigma) in the left hind paw.

[Scoring of Inflammatory Pain & Grouping] Inflammatory pain in the left hind paw was scored by Randall-Selitto test using an electronic Randall-Selitto apparatus [Model 2390, IITC Life sciences]. Rats were acclimated on a hammock for 10 min prior to pain scoring. (N=5 per group)

In Day 0, 10 animals stably showing the lowest pain threshold scores over several days were selected for grouping. The 10 animals were assigned to two groups of the negative control group (no ASO treatment) and the treatment group ("ASO 2" 100 pmole/Kg).

[ASO Treatment & Pain Assessment] The treatment group animals received "ASO 2" at 100 pmole/Kg in the afternoon of Day 0 and in the morning of Day 1. The ASO was dissolved in PBS and subcutaneously administered. Pain was assessed 2 hours post dose in Day 1, and in the morning in Day 4.

Figure 24B:
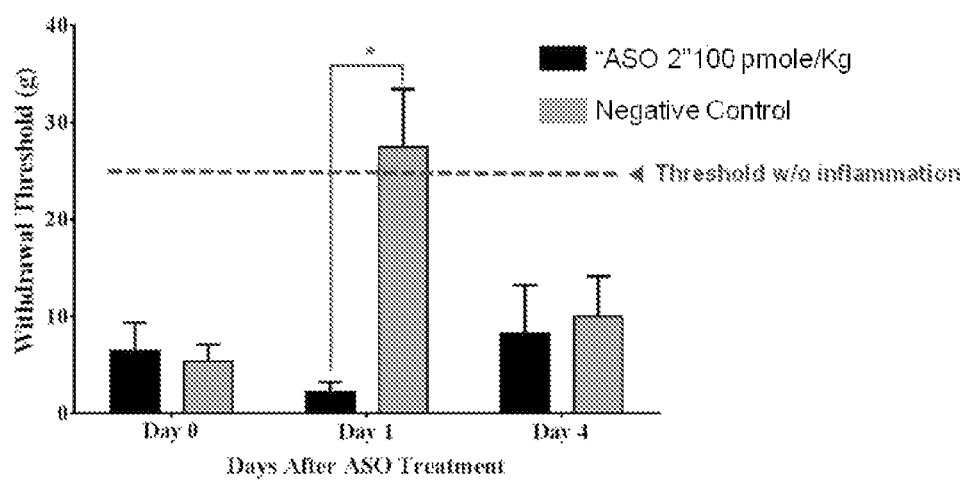
FIG. 24B. Changes in the pain threshold by Randall-Selitto test in rats subcutaneously administered with "ASO 2" at 0 (negative control) or 100 pmole/Kg in Days 0 and 1. (error bar by standard error; * for p<0.05 by student's t-test)

[Analgesic Activity] FIG. 24B summarizes the observed pain scores. The pain threshold of the ASO treatment group in Day 1 increased to ca 27 g compared to the value in Day 0, whilst the threshold of the negative control group decreased to ca 3 g. The pain threshold prior to the induction of the paw edema was ca 23 g. Thus the ASO administration completely reversed the inflammatory pain to the level without paw edema. However, the analgesic activity of "ASO 2" washed out completely in Day 4.

What is claimed is:

1. A peptide nucleic acid derivative represented by Formula I, or a pharmaceutically acceptable salt thereof:

Formula I

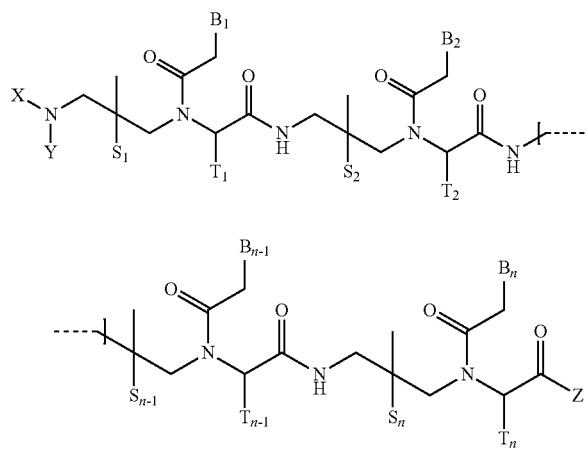

wherein, n is an integer between 10 and 25;

the compound of Formula I possesses at least a 10-mer complementary overlap with a 14-mer pre-mRNA sequence of [(5'→3') UGUUUAGGUACACU (SEQ ID NO: 2)] within the human SCN9A pre-mRNA;

the compound of Formula I is fully complementary to the human SCN9A pre-mRNA, or partially complementary to the human SCN9A pre-mRNA with one or two mismatches;

$S_1, S_2, \ldots, S_{n-1}, S_n, T_1, T_2, \ldots, T_{n-1}$, and $T_n$ independently represent deuterido [D], hydrido [H], substituted or non-substituted alkyl, or substituted or non-substituted aryl radical;

X and Y independently represent hydrido, formyl [H—C(=O)—], aminocarbonyl [NH$_2$—C(=O)—], aminothiocarbonyl [NH$_2$—C(=S)—], substituted or non-substituted alkyl, substituted or non-substituted aryl, substituted or non-substituted alkylacyl, substituted or non-substituted arylacyl, substituted or non-substituted alkyloxycarbonyl, substituted or non-substituted aryloxycarbonyl, substituted or non-substituted alkylaminocarbonyl, substituted or non-substituted arylaminocarbonyl, substituted or non-substituted alkylaminothiocarbonyl, substituted or non-substituted arylaminothiocarbonyl, substituted or non-substituted alkyloxythiocarbonyl, substituted or non-substituted aryloxythiocarbonyl, substituted or non-substituted alkylsulfonyl, substituted or non-substituted arylsulfonyl, substituted or non-substituted alkylphosphonyl radical, or substituted or non-substituted arylphosphonyl radical;

Z represents hydrido, hydroxy, substituted or non-substituted alkyloxy, substituted or non-substituted aryloxy, substituted or non-substituted amino, substituted or non-substituted alkyl, or substituted or non-substituted aryl radical;

$B_1, B_2, \ldots, B_{n-1}$, and $B_n$ are independently selected from natural nucleobases including adenine, thymine, guanine, cytosine and uracil, and unnatural nucleobases; and, at least four of $B_1, B_2, \ldots, B_{n-1}$, and $B_n$ are independently selected from unnatural nucleobases with a substituted or non-substituted amino radical covalently linked to the nucleobase moiety.

2. The peptide nucleic acid derivative according to claim 1, or a pharmaceutical salt thereof:

wherein, n is an integer between 10 and 25;

the compound of Formula I possesses at least a 10-mer complementary overlap with the 14-mer pre-mRNA sequence of [(5'→3') UGUUUAGGUACACU (SEQ ID NO: 2)] within the human SCN9A pre-mRNA;

the compound of Formula I is fully complementary to the human SCN9A pre-mRNA, or partially complementary to the human SCN9A pre-mRNA with one or two mismatches;

$S_1, S_2, \ldots, S_{n-1}, S_n, T_1, T_2, \ldots, T_{n-1}$, and $T_n$ independently represent deuterido, hydrido, substituted or non-substituted alkyl, or substituted or non-substituted aryl radical;

X and Y independently represent hydrido, formyl, aminocarbonyl, aminothiocarbonyl, substituted or non-substituted alkyl, substituted or non-substituted aryl, substituted or non-substituted alkylacyl, substituted or non-substituted arylacyl, substituted or non-substituted alkyloxycarbonyl, substituted or non-substituted aryloxycarbonyl, substituted or non-substituted alkylaminocarbonyl, substituted or non-substituted arylaminocarbonyl, substituted or non-substituted alkylaminothiocarbonyl, substituted or non-substituted arylaminothiocarbonyl, substituted or non-substituted alkyloxythiocarbonyl, substituted or non-substituted aryloxythiocarbonyl, substituted or non-substituted alkyl sulfonyl, substituted or non-substituted aryl sulfonyl, substituted or non-substituted alkylphosphonyl radical, or substituted or non-substituted arylphosphonyl radical;

Z represents hydrido, hydroxy, substituted or non-substituted alkyloxy, substituted or non-substituted aryloxy, substituted or non-substituted amino, substituted or non-substituted alkyl, or substituted or non-substituted aryl radical;

$B_1, B_2, \ldots, B_{n-1}$, and $B_n$ are independently selected from natural nucleobases including adenine, thymine, guanine, cytosine and uracil, and unnatural nucleobases; and, at least four of $B_1, B_2, \ldots, B_{n-1}$, and $B_n$ are independently selected from unnatural nucleobases represented by Formula II, Formula III, or Formula IV:

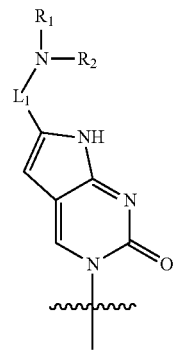

Formula II

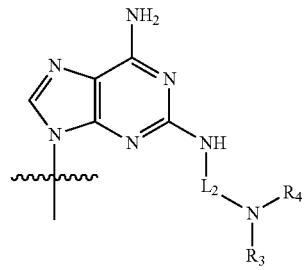

Formula III

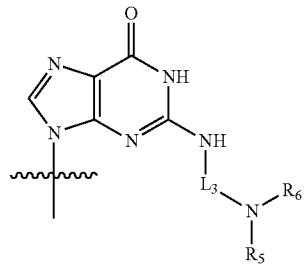

Formula IV wherein, $R_1, R_2, R_3, R_4, R_5$ and $R_6$ are independently selected from hydrido, and substituted or non-substituted alkyl radical;

$L_1, L_2$ and $L_3$ are a covalent linker represented by Formula V covalently linking the basic amino group to the nucleobase moiety:

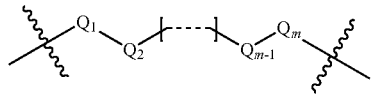

Formula V wherein, $Q_1$ and $Q_m$ are substituted or non-substituted methylene ($-CH_2-$) radical, and $Q_m$ is directly linked to the basic amino group;

$Q_2, Q_3, \ldots$, and $Q_{m-1}$ are independently selected from substituted or non-substituted methylene, oxygen ($-O-$), sulfur ($-S-$), and substituted or non-substituted amino radical [$-N(H)-$, or $-N$(substituent)-]; and, m is an integer between 1 and 15.

3. The peptide nucleic acid derivative of claim 2, wherein $S_1, S_2, \ldots, S_{n-1}, S_n, T_1, T_2, \ldots, T_{n-1}$, and $T_n$ independently represent deuterido or hydrido radical and Z represents hydrido, hydroxy, substituted or non-substituted alkyloxy, substituted or non-substituted aryloxy, or substituted or non-substituted amino radical.

4. The peptide nucleic acid derivative of claim 2, wherein at least one of $S_1, S_2, \ldots, S_{n-1}, S_n, T_1, T_2, \ldots, T_{n-1}$, and $T_n$ independently represents substituted or non-substituted alkyl, or substituted or non-substituted aryl radical, and/or Z represents substituted or non-substituted alkyl or substituted or non-substituted aryl radical.

5. The peptide nucleic acid derivative according to claim 1, or a pharmaceutical salt thereof:
wherein,
n is an integer between 11 and 21;
the compound of Formula I possesses at least a 10-mer complementary overlap with the 14-mer pre-mRNA sequence of [(5'→3') UGUUUAGGUACACU (SEQ ID NO: 2)] within the human SCN9A pre-mRNA;
the compound of Formula I is fully complementary to the human SCN9A pre-mRNA, or partially complementary to the human SCN9A pre-mRNA with one or two mismatches;
$S_1, S_2, \ldots, S_{n-1}, S_n, T_1, T_2, \ldots, T_{n-1}$, and $T_n$ are hydrido radical;
X and Y independently represent hydrido, substituted or non-substituted alkyl, substituted or non-substituted aryl, substituted or non-substituted alkylacyl, substituted or non-substituted arylacyl, substituted or non-substituted alkyloxycarbonyl, substituted or non-substituted aryloxycarbonyl, substituted or non-substituted alkylaminocarbonyl, substituted or non-substituted arylaminocarbonyl, substituted or non-substituted alkylsulfonyl, or substituted or non-substituted arylsulfonyl radical;
Z represents substituted or non-substituted amino radical;
$B_1, B_2, \ldots, B_{n-1}$, and $B_n$ are independently selected from natural nucleobases including adenine, thymine, guanine, cytosine and uracil, and unnatural nucleobases;
at least four of $B_1, B_2, \ldots, B_{n-1}$, and $B_n$ are independently selected from unnatural nucleobases represented by Formula II, Formula III, or Formula IV;
$R_1, R_2, R_3, R_4, R_5$ and $R_6$ are independently selected from hydrido, and substituted or non-substituted alkyl radical;
$Q_1$ and $Q_m$ are substituted or non-substituted methylene radical, and $Q_m$ is directly linked to the basic amino group;
$Q_2, Q_3, \ldots,$ and $Q_{m-1}$ are independently selected from substituted or non-substituted methylene, oxygen, and amino radical; and,
m is an integer between 1 and 11.

6. The peptide nucleic acid derivative of claim 5, wherein X and Y independently represent hydrido, substituted or non-substituted alkyl, substituted or non-substituted aryl, substituted or non-substituted alkylacyl, substituted or non-substituted arylacyl, substituted or non-substituted alkyloxycarbonyl, or substituted or non-substituted aryloxycarbonyl radical.

7. The peptide nucleic acid derivative of claim 5, wherein at least one of X and Y independently represents substituted or non-substituted alkylaminocarbonyl, substituted or non-substituted arylaminocarbonyl, substituted or non-substituted alkylsulfonyl, or substituted or non-substituted arylsulfonyl radical.

8. The peptide nucleic acid derivative according to claim 1, or a pharmaceutical salt thereof:
wherein,
n is an integer between 11 and 19;
the compound of Formula I possesses at least a 10-mer complementary overlap with the 14-mer pre-mRNA sequence of [(5'→3') UGUUUAGGUACACU (SEQ ID NO: 2)] within the human SCN9A pre-mRNA;
the compound of Formula I is fully complementary to the human SCN9A pre-mRNA;
$S_1, S_2, \ldots, S_{n-1}, S_n, T_1, T_2, \ldots, T_{n-1}$, and $T_n$ are hydrido radical;
X and Y independently represent hydrido, substituted or non-substituted alkyl, substituted or non-substituted aryl, substituted or non-substituted alkylacyl, substituted or non-substituted arylacyl, substituted or non-substituted alkyloxycarbonyl, substituted or non-substituted alkylaminocarbonyl, substituted or non-substituted alkylsulfonyl, or substituted or non-substituted arylsulfonyl radical;
Z represents substituted or non-substituted amino radical;
$B_1, B_2, \ldots, B_{n-1}$, and $B_n$ are independently selected from natural nucleobases including adenine, thymine, guanine, cytosine and uracil, and unnatural nucleobases;
at least four of $B_1, B_2, \ldots, B_{n-1}$, and $B_n$ are independently selected from unnatural nucleobases represented by Formula II, Formula III, or Formula IV;
$R_1, R_2, R_3, R_4, R_5$ and $R_6$ are independently selected from hydrido, and substituted or non-substituted alkyl radical;
$Q_1$ and $Q_m$ are methylene radical, and $Q_m$ is directly linked to the basic amino group;
$Q_2, Q_3, \ldots,$ and $Q_{m-1}$ are independently selected from methylene, oxygen, and amino radical; and,
m is an integer between 1 and 9.

9. The peptide nucleic acid derivative of claim 8, wherein X and Y independently represent hydrido, substituted or non-substituted alkylacyl, or substituted or non-substituted alkyloxycarbonyl radical.

10. The peptide nucleic acid derivative of claim 8, wherein at least one of X and Y independently represents substituted or non-substituted alkyl, substituted or non-substituted aryl, substituted or non-substituted arylacyl, substituted or non-substituted alkylaminocarbonyl, substituted or non-substituted alkyl sulfonyl, or substituted or non-substituted aryl sulfonyl radical.

11. The peptide nucleic acid derivative according to claim 1, or a pharmaceutical salt thereof:
wherein,
n is an integer between 11 and 19;
the compound of Formula I possesses at least a 10-mer complementary overlap with the 14-mer pre-mRNA sequence of [(5'→3') UGUUUAGGUACACU (SEQ ID NO: 2)] within the human SCN9A pre-mRNA;
the compound of Formula I is fully complementary to the human SCN9A pre-mRNA;
$S_1, S_2, \ldots, S_{n-1}, S_n, T_1, T_2, \ldots, T_{n-1}$, and $T_n$ are hydrido radical;
X and Y independently represent hydrido, substituted or non-substituted alkyl, substituted or non-substituted aryl, substituted or non-substituted alkylacyl, substituted or non-substituted arylacyl, or substituted or non-substituted alkyloxycarbonyl radical;
Z represents substituted or non-substituted amino radical;
$B_1, B_2, \ldots, B_{n-1}$, and $B_n$ are independently selected from natural nucleobases including adenine, thymine, guanine, cytosine and uracil, and unnatural nucleobases;
at least four of $B_1, B_2, \ldots, B_{n-1}$, and $B_n$ are independently selected from unnatural nucleobases represented by Formula II, Formula III, or Formula IV;

$R_1$, $R_3$, and $R_5$ are hydrido radical, and $R_2$, $R_4$, and $R_6$ independently represent hydrido, or substituted or non-substituted alkyl radical;

$Q_1$ and $Q_m$ are methylene radical, and $Q_m$ is directly linked to the basic amino group;

$Q_2$, $Q_3$, ..., and $Q_{m-1}$ are independently selected from methylene, oxygen radical; and, m is an integer between 1 and 8.

12. The peptide nucleic acid derivative of claim 11, wherein X and Y independently represent hydrido, substituted or non-substituted alkylacyl, or substituted or non-substituted alkyloxycarbonyl radical.

13. The peptide nucleic acid derivative of claim 11, wherein at least one of X and Y independently represents substituted or non-substituted alkyl, substituted or non-substituted aryl, or substituted or non-substituted arylacyl radical.

14. The peptide nucleic acid derivative according to claim 1, or a pharmaceutical salt thereof:
thereof:
wherein,
n is an integer between 11 and 19;
the compound of Formula I possesses at least a 10-mer complementary overlap with the 14-mer pre-mRNA sequence of [(5'→3') UGUUUAGGUACACU (SEQ ID NO: 2)] within the human SCN9A pre-mRNA;
the compound of Formula I is fully complementary to the human SCN9A pre-mRNA;
$S_1$, $S_2$, ..., $S_{n-1}$, $S_n$, $T_1$, $T_2$, ..., $T_{n-1}$, and $T_n$ are hydrido radical;
X and Y independently represent hydrido, substituted or non-substituted alkylacyl, substituted or non-substituted arylacyl, or substituted or non-substituted alkyloxycarbonyl radical;
Z represents substituted or non-substituted amino radical;
$B_1$, $B_2$, ..., $B_{n-1}$, and $B_n$ are independently selected from adenine, thymine, guanine, cytosine, and unnatural nucleobases;
at least five of $B_1$, $B_2$, ..., $B_{n-1}$, and $B_n$ are independently selected from unnatural nucleobases represented by Formula II, Formula III, or Formula IV;
$R_1$, $R_2$, $R_3$, $R_4$, $R_5$, and $R_6$ are hydrido radical;
$Q_1$ and $Q_m$ are methylene radical, and $Q_m$ is directly linked to the basic amino group;
$Q_2$, $Q_3$, ..., and $Q_{m-1}$ are independently selected from methylene, and oxygen radical; and,
m is an integer between 1 and 8.

15. The peptide nucleic acid derivative of claim 14, wherein X and Y independently represent hydrido, substituted or non-substituted alkylacyl, or substituted or non-substituted alkyloxycarbonyl radical.

16. The peptide nucleic acid derivative of claim 14, wherein at least one of X and Y independently represents substituted or non-substituted arylacyl.

17. The peptide nucleic acid derivative according to claim 1, or a pharmaceutical salt thereof:
wherein,
n is an integer between 11 and 19;
the compound of Formula I possesses at least a 10-mer complementary overlap with the 14-mer pre-mRNA sequence of [(5'→3') UGUUUAGGUACACU (SEQ ID NO: 2)] within the human SCN9A pre-mRNA;
the compound of Formula I is fully complementary to the human SCN9A pre-mRNA;
$S_1$, $S_2$, ..., $S_{n-1}$, $S_n$, $T_1$, $T_2$, ..., $T_{n-1}$, and $T_n$ are hydrido radical;
X is hydrido radical;
Y represents substituted or non-substituted alkylacyl, substituted or non-substituted arylacyl, or substituted or non-substituted alkyloxycarbonyl radical;
Z represents substituted or non-substituted amino radical;
$B_1$, $B_2$, ..., $B_{n-1}$, and $B_n$ are independently selected from adenine, thymine, guanine, cytosine, and unnatural nucleobases;
at least five of $B_1$, $B_2$, ..., $B_{n-1}$, and $B_n$ are independently selected from unnatural nucleobases represented by Formula II, Formula III, or Formula IV;
$R_1$, $R_2$, $R_3$, $R_4$, $R_5$, and $R_6$ are hydrido radical;
$L_1$ represents —(CH$_2$)$_2$—O—(CH$_2$)$_2$—, —CH$_2$—O—(CH$_2$)$_2$—, —CH$_2$—O—(CH$_2$)$_3$—, —CH$_2$—O—(CH$_2$)$_4$—, or —CH$_2$—O—(CH$_2$)$_5$— with the right end is directly linked to the basic amino group; and,
$L_2$ and $L_3$ are independently selected from —(CH$_2$)$_2$—, —(CH$_2$)$_3$—, —(CH$_2$)$_4$—, —(CH$_2$)$_5$—, —(CH$_2$)$_6$—, —(CH$_2$)$_7$—, —(CH$_2$)$_8$—, —(CH$_2$)$_2$—O—(CH$_2$)$_2$—, —(CH$_2$)$_3$—O—(CH$_2$)$_2$—, and —(CH$_2$)$_2$—O—(CH$_2$)$_3$— with the right end is directly linked to the basic amino group.

18. The peptide nucleic acid derivative of claim 17, wherein Y represents substituted or non-substituted alkylacyl, substituted or non-substituted alkyloxycarbonyl radical, or substituted or non-substituted arylacyl.

19. The peptide nucleic acid derivative according to claim 1, which is selected from the group of peptide nucleic acid derivatives provided below, or a pharmaceutically acceptable salt thereof:

(N → C) Fethoc-TA(5)A-A(5)AG(6)-TG(6)T-A(5)CC(102)-TA(5)A-A(5)-NH$_2$;

(N → C) Fethoc-TA(5)A-A(4)AG(6)-TG(6)T-A(5)CC(103)-TA(5)A-A-NH$_2$;

(N → C) Fmoc-TA(5)A-A(4)AG(6)-TG(6)T-A(5)CC(103)-TA(5)A-A-NH$_2$;

(N → C) Piv-Leu-TA(5)A-A(5)AG(302)-TG(6)T-A(5)CC(102)-TA(5)A-A(5)-NH$_2$;

(N → C) Fethoc-TA(5)T-A(5)AG(6)-TG(6)T-A(5)CC(102)-TA(5)A-A(5)-NH$_2$;

(N → C) Benzoyl-Gly-TA(202)A-A(5)AG(6)-TG(6)T-A(5)CT-TA(5)A-Lys-NH$_2$;

(N → C) Fethoc-AA(5)G-TG(6)T-A(5)CC(102)-TAA(5)-A-NH$_2$;

(N → C) Fethoc-AA(5)G-CG(6)T-A(5)CC(102)-TAA(5)-A-NH$_2$;

(N → C) Fmoc-AA(5)G-TG(6)T-A(5)CC(102)-TAA(5)-A-NH$_2$;

(N → C) Benzenesulfonyl-AA(5)G-TG(6)T-A(5)CC(102)-TAA(5)-A-NH$_2$;

(N → C) Ac-AA(5)G-TG(6)T-A(5)CC(102)-TAA(5)-A-NH$_2$;

-continued (N → C) Fethoc-AA(5)G-TG(5)T-A(5)CC(102)-TA(3)A-A(5)-NH$_2$;

(N → C) Fmoc-AA(5)G-TG(6)T-AC(102)C-TAA(5)-A-NH$_2$;

(N → C) Methyl-AA(5)G-TG(5)T-A(5)CC(102)-TA(3)A-A(5)-Gly-Arg-NH$_2$;

(N → C) Fethoc-A(5)AG-TG(6)T-A(5)CC(102)-TAA-A(5)-NH$_2$;

(N → C) Ac-Val-A(5)AG-TG(6)T-A(5)CC(102)-TAA-A(5)-NH$_2$;

(N → C) Fethoc-AAG(6)-TG(6)T-A(5)CC(102)-TA(5)A-A-NH$_2$;

(N → C) Fethoc-AA(5)G-TG(5)T-A(5)CC(102)-TA(5)A-A(5)-NH$_2$, (N → C) Fethoc-AA(5)G-TG(5)T-A(5)CC(102)-TA(5)A-A(5)C-NH$_2$;

(N → C) Fethoc-AA(5)G-TG(5)T-A(5)AC(102)-TA(5)T-A(5)C-NH$_2$;

(N → C) H-AA(5)G-TG(202)T-A(5)CC(102)-TA(5)A-A(5)C-NH$_2$;

(N → C) Fethoc-Lys-Leu-AA(5)G-TG(5)T-A(5)CC(102)-TA(202)A-A(5)C-Lys-NH$_2$;

(N → C) [N-(2-Phenylethyl)amino]carbonyl-AA(3)G-TG(5)T-A(5)CC(105)-TA(5)A-A(5)C-NH$_2$;

(N → C) N,N-Phenyl-Me-AA(5)G-TG(5)T-A(5)CC(102)-TA(5)A-A(4)C-NH$_2$;

(N → C) Fethoc-AA(5)G-TA(5)T-A(5)CC(102)-TG(5)A-A(5)C-NH$_2$;

(N → C) p-Toluenesulfonyl-AA(5)G-TG(5)T-A(5)CC(102)-TA(5)A-A(5)C-NH$_2$;

(N → C) p-Toluenesulfonyl-AA(5)G-TG(203)T-A(5)CC(102)-TA(5)A-A(5)C-Lys-NH$_2$;

(N → C) Fethoc-AA(5)G-TG(203)T-A(5)CC(103)-TA(7)A-A(5)-NH$_2$;

(N → C) n-Propyl-AA(5)G-TG(5)T-A(5)CC(103)-TA(5)A-A(5)C-NH$_2$;

(N → C) Benzoyl-AA(5)G-TG(5)T-A(5)CC(102)-TA(5)A-A(5)C-NH$_2$;

(N → C) Benzyl-AA(5)G-TG(5)T-A(5)CC(103)-TA(5)A-A(5)C-NH$_2$;

(N → C) Benzoyl-AA(5)G-TG(3)T-A(5)CC(202)-TA(5)A-A(5)C-NH$_2$;

(N → C) Fethoc-AA(5)G-TG(5)T-A(5)CC(102)-TA(5)A-A(5)C-Leu-Lys-NH$_2$;

(N → C) Piv-AA(5)G-TG(5)T-A(5)CC(102)-TA(5)A-A(5)C-NH$_2$;

(N → C) Fethoc-TA(5)G-TG(5)T-A(5)CC(102)-TA(5)A-A(5)C-NH$_2$;

(N → C) Fethoc-AA(5)C-TG(5)T-A(5)CC(102)-TA(5)A-A(5)C-NH$_2$;

(N → C) Methylsulfonyl-AA(5)G-TG(5)T-A(5)CC(102)-TA(5)A-A(5)C-NH$_2$;

(N → C) n-Hexyl-AA(5)G-TG(5)T-A(5)CC(102)-TA(5)A-A(5)C-NH$_2$;

(N → C) n-Hexanoyl-AA(5)G-TG(5)T-A(5)CC(102)-TA(5)A-A(5)C-NH$_2$;

(N → C) n-Hexanoyl-AA(5)G-TG(5)T-A(5)CC(102)-TA(8)A-A(5)C-NH$_2$;

(N → C) Fethoc-AA(3)G-TG(202)T-A(5)CC(102)-TA(5)A-A(5)C-NH$_2$;

(N → C) Fethoc-AA(3)G-TG(202)T-A(5)CC(103)-TA(5)A-A(5)C-NH$_2$;

(N → C) Fethoc-AA(3)G-TG(202)T-A(5)CC(202)-TA(5)A-A(5)C-NH$_2$;

(N → C) FAM-HEX-HEX-AA(3)G-TG(202)T-A(5)CC(202)-TA(5)A-A(5)C-NH$_2$;

(N → C) Fethoc-A(5)GT-G(5)TA(5)-CC(102)T-A(5)AA(5)-C-NH$_2$;

(N → C) Fethoc-AG(5)T-G(7)TA-CC(102)T-AA(6)A-C-NH$_2$;

(N → C) Fethoc-AA(6)G-TG(5)T-A(6)CC(102)-TA(6)A-A(6)C-NH$_2$;

(N → C) Fethoc-AA(5)G-TG(5)T-A(5)CC(102)-TA(5)A-A(3)CA-C(105)AA-NH$_2$;

(N → C) Fethoc-AA(5)G-TCT-A(5)CC(102)-TA(5)A-A(3)CA-C(105)AA-NH$_2$;

(N → C) Fethoc-AA(5)G-TCT-A(5)CC(102)-TA(5)A-A(3)CA(3)-CTA-NH$_2$;

(N → C) Fethoc-TG(5)T-A(5)CC(102)-TA(5)A-A(3)CA-CA(7)A-NH$_2$;

-continued (N → C) Fethoc-AA(5)G-TG(5)T-A(5)CC(102)-TA(5)A-A(3)CA(5)-C-NH₂;

(N → C) Fethoc-TG(5)T-A(5)CC(102)-TA(5)A-A(3)CA(5)-C-NH₂;

(N → C) p-Toluenesulfonyl-TG(203)T-A(5)CC(102)-TA(5)A-A(3)CA-C-Lys-NH₂;

(N → C) Fethoc-TG(5)T-A(5)CC(202)-TA(5)A-A(3)CA-CA(5)A-NH₂;

(N → C) Piv-TG(5)T-A(5)CC(202)-TA(5)A-A(3)CA-CA(5)A-NH₂;

(N → C) Benzoyl-TG(5)T-A(5)CC(202)-TA(5)A-A(3)CA-CA(5)A-NH₂;

(N → C) Propionyl-TG(5)T-A(5)CC(202)-TA(5)A-A(3)CA-CA(5)A-NH₂;

(N → C) Fethoc-TG(5)T-A(5)CC(202)-TA(5)A-A(3)CA-CA(5)A-Arg-Val-NH₂;

(N → C) Fethoc-AA(5)G-TG(5)T-A(5)CC(102)-TA(5)A-A(5)G-NH₂;

(N → C) Fethoc-AG(5)G-TG(5)T-A(5)CC(102)-TA(5)A-A(5)G-NH₂;

(N → C) Fethoc-AA(5)G-TG(5)T-A(5)CC(102)-TA(5)A-A(5)CA-NH₂;

(N → C) Fethoc-AA(5)G-TG(5)T-A(5)CC(102)-TA(5)A-A(5)GG-NH₂;
and, (N → C) Fethoc-AA(5)G-TG(5)T-ACC(102)-TA(5)A-A(5)CA(5)-C-NH₂:

wherein,
A, G, T, and C are PNA monomers with a natural nucleobase of adenine, guanine, thymine, and cytosine, respectively;
C(pOq), A(p), A(pOq), G(p), and G(pOq) are PNA monomers with an unnatural nucleobase represented by Formula VI, Formula VII, Formula VIII, Formula IX, and Formula X, respectively;

Formula VI

Formula VII

Formula VIII

Formula IX

Formula X wherein,
p and q are integers; and,
the abbreviations for the N- and C-terminus substituents are specifically defined as follows: "Fmoc-" is the abbreviation for "[(9-fluorenyl)methyloxy]carbonyl-"; "Fethoc-" for "[2-(9-fluorenyl)ethyl-1-oxy]carbonyl"; "Ac-" for "acetyl-"; "n-Hexanoyl-" for "1-(n-hexanoyl)-"; "Benzoyl-" for "benzenecabonyl-"; "Piv-" for "pivalyl-"; "n-Propyl-" for "1-(n-propyl)-"; "n-Hexyl-" for "1-(n-hexyl)-"; "H-" for "hydrido-"; "p-Toluenesulfonyl" for "(4-methylbenzene)-1-sulfonyl-"; "Benzenesulfonyl" for "benzene-1-sulfonyl-"; "Methylsulfonyl" for "methyl-1-sulfonyl-"; "-Lys-" for amino acid residue "lysine"; "—Val-" for amino acid residue "valine"; "-Leu-" for amino acid residue "leucine"; "-Arg-" for amino acid residue "arginine"; "-Gly-" for amino acid residue "glycine"; "[N-(2-Phenylethyl)amino] carbonyl-" for "[N-1-(2-phenylethyl)-amino]carbonyl-"; "Benzyl-" for "1-(phenyl)methyl-"; "Phenyl-" for "phenyl-"; "Me-" for "methyl-"; "—HEX-" for "6-amino-1-hexanoyl-", "FAM-" for "5, or 6-fluorescein-carbonyl-" (isomeric mixture), and "—NH₂" for non-substituted "-amino" group.

20. A method to treat pain involving unwanted expression of Nav1.7 in a subject, comprising administering to the subject the peptide nucleic acid derivative of claim 1, wherein the peptide nucleic acid derivative down-regulates Nav1.7 expression.

21. The method of claim 20, wherein the pain is chronic pain.

22. The method of claim 20, wherein the pain is neuropathic pain.

23. A method of inducing skipping of exon 4 in the SCN9A pre-mRNA to yield a SCN9A mRNA splice variant lacking SCN9A exon 4 in cells comprising contacting the cells with the peptide nucleic acid derivative of claim 1.

24. The method of claim 23, wherein the cells express a lower level of the full length SCN9A mRNA and show a lower Nav1.7 functional activity than cells without contacting with the peptide nucleic acid derivative.

* * * * *

UNITED STATES PATENT AND TRADEMARK OFFICE
CERTIFICATE OF CORRECTION

PATENT NO. : 11,162,104 B2
APPLICATION NO. : 16/480147
DATED : November 2, 2021
INVENTOR(S) : Shin Chung et al.

It is certified that error appears in the above-identified patent and that said Letters Patent is hereby corrected as shown below:

In the Claims

Column 59, Line 20, Claim 14, delete "thereof:"

Column 64, Lines 11-19, Claim 19, delete:
Formula VII

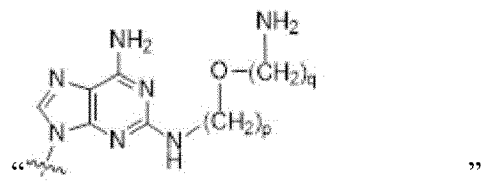

"

And replace with:
Formula VIII

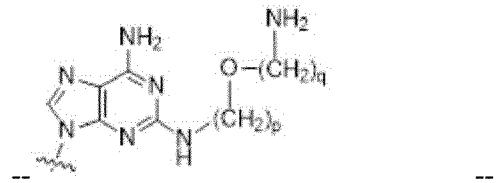

--

Signed and Sealed this
Thirtieth Day of August, 2022

Katherine Kelly Vidal
*Director of the United States Patent and Trademark Office*